United States Patent
LeCursi et al.

(10) Patent No.: US 10,814,571 B2
(45) Date of Patent: Oct. 27, 2020

(54) CURABLE, CONFORMABLE COMPOSITE PRECURSORS, CONFORMABLE CORE STRUCTURES, RESULTING PRODUCTS AND METHODS

(71) Applicant: Becker Orthopedic Appliance Company, Troy, MI (US)

(72) Inventors: Nicholas LeCursi, Saline, MI (US); Alec Bashore, Sterling Heights, MI (US); Nicholas Zalinski, Macomb Twp., MI (US); Rodger Broick, Romeo, MI (US); James Campbell, Clarkston, MI (US)

(73) Assignee: Becker Orthopedic Appliance Company, Troy, MI (US)

( * ) Notice: Subject to any disclaimer, the term of this patent is extended or adjusted under 35 U.S.C. 154(b) by 1083 days.

(21) Appl. No.: 15/098,489

(22) Filed: Apr. 14, 2016

(65) Prior Publication Data

US 2017/0297278 A1 Oct. 19, 2017

(51) Int. Cl.
*A61F 13/04* (2006.01)
*A61F 5/01* (2006.01)
(Continued)

(52) U.S. Cl.
CPC ............ *B29C 70/44* (2013.01); *A61F 5/0113* (2013.01); *A61F 5/0127* (2013.01); *A61F 5/028* (2013.01);
(Continued)

(58) Field of Classification Search
CPC ...... A61F 13/04; A61F 5/0113; A61F 5/0127; A61F 5/028; B29C 70/22; B29C 70/28;
(Continued)

(56) References Cited

U.S. PATENT DOCUMENTS 4,672,955 A   6/1987 Cooper
4,893,617 A   1/1990 Bartial et al.
(Continued)

FOREIGN PATENT DOCUMENTS

WO   WO2012174623 A1   12/2012
WO   WO2015054128 A1   4/2015

OTHER PUBLICATIONS

International Searching Authority (ISA/US), International Search Report and Written Opinion, International Application No. PCT/US2017/027161, dated Aug. 29, 2017.

*Primary Examiner* — Keri J Nelson
(74) *Attorney, Agent, or Firm* — Hinshaw & Culbertson LLP

(57) ABSTRACT

The application discloses a conformable support structure for use in fiber composite precursor; a resin impregnated conformable fiber composite precursor, which may surround the support structure, for being manually manipulated and plastically deformed into a desired shape before being cured into a final product having the desired shape; the corresponding final product, which may be an orthosis or other product; and methods of making the final product or orthosis. The support structure is typically plastically deformable by hand to form the desired shape, may be substantially planar and may have various voids to promote controlled plastic deformation of the frame in one or more desired directions. The core may comprise a wire or tube and may include packing or filler material. The precursor includes a fiber layer impregnated with a thermoset resin and includes a compressor around the fiber layer. The fiber layer is supported internally or externally by the conformable support member. The precursor may be custom fitted to match the shape of an object and then thermally cured into a strong (Continued)

rigid product. The cured precursor can then be used to make a custom finished product.

61 Claims, 32 Drawing Sheets

(51) Int. Cl.
  *B29C 70/44* (2006.01)
  *B29C 70/88* (2006.01)
  *B29C 70/28* (2006.01)
  *A61F 5/02* (2006.01)
  *B29C 70/22* (2006.01)
  *B29L 31/00* (2006.01)

(52) U.S. Cl.
  CPC .............. *A61F 13/04* (2013.01); *B29C 70/22* (2013.01); *B29C 70/28* (2013.01); *B29C 70/885* (2013.01); *B29L 2031/753* (2013.01)

(58) Field of Classification Search
  CPC .. B29C 70/44; B29C 70/885; B29L 2031/753
  USPC ........................................................ 602/5–7
  See application file for complete search history.

(56) References Cited

U.S. PATENT DOCUMENTS

| | | |
|---|---|---|
| 5,076,871 A | 12/1991 | Frye et al. |
| 5,470,622 A | 11/1995 | Rinde et al. |
| 5,651,743 A | 7/1997 | Stephan et al. |
| 5,698,055 A | 12/1997 | Benkoczy |
| 6,146,344 A | 11/2000 | Bader |
| 6,821,638 B2 | 11/2004 | Obeshaw |
| 6,824,522 B2* | 11/2004 | Henderson .............. A61F 13/04 602/5 |
| 8,241,739 B2 | 8/2012 | Schonfeld et al. |
| 8,343,082 B2* | 1/2013 | Evans .................... A61F 13/04 602/5 |
| 8,465,445 B2 | 6/2013 | George |
| 2002/0193718 A1 | 12/2002 | Henderson et al. |
| 2003/0219578 A1 | 11/2003 | Jones et al. |
| 2004/0134500 A1 | 7/2004 | Ingimundarson et al. |
| 2010/0063431 A1 | 3/2010 | Bae |
| 2013/0220645 A1 | 8/2013 | Kirkpatrick et al. |
| 2016/0095734 A1* | 4/2016 | Sigurdsson ........... A61F 5/0109 602/26 |
| 2016/0270945 A1 | 9/2016 | Tomblin et al. |

* cited by examiner

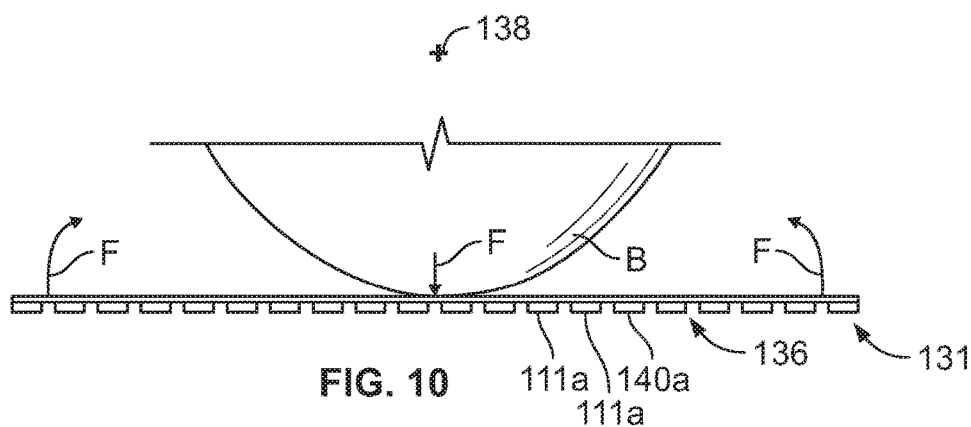
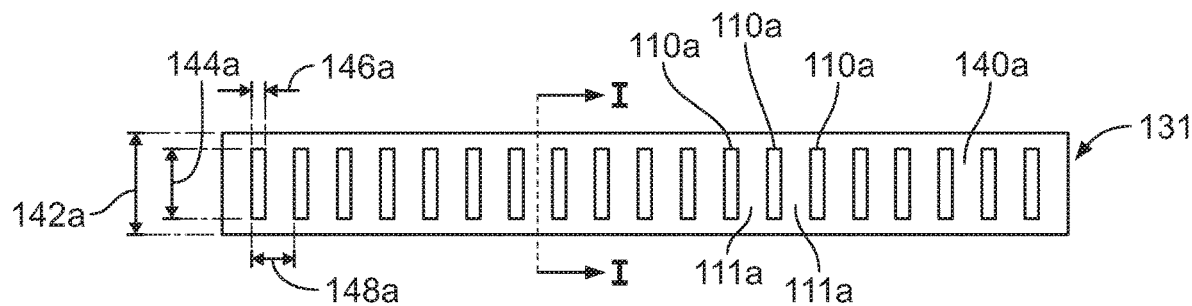
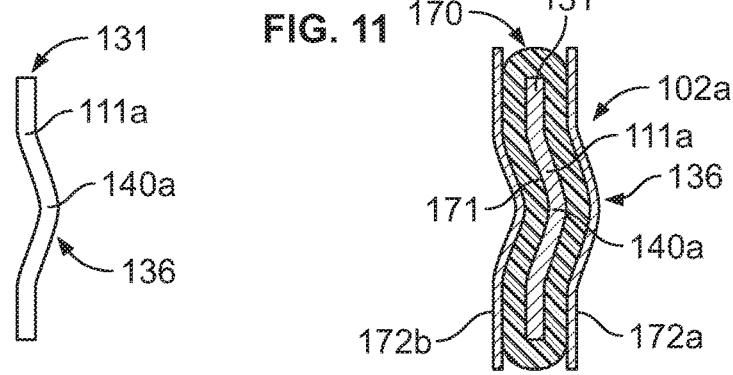
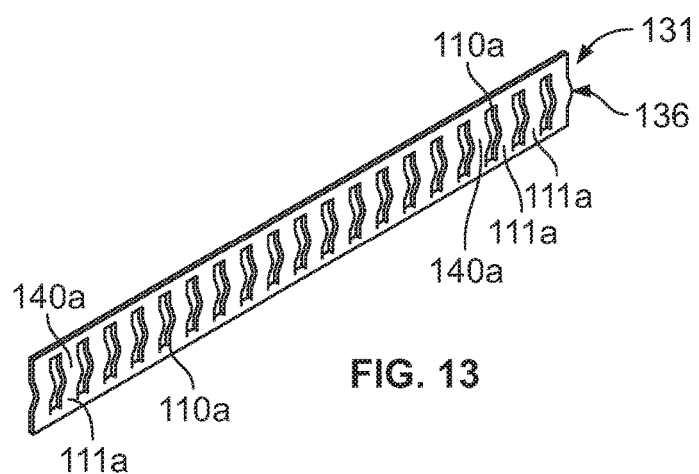

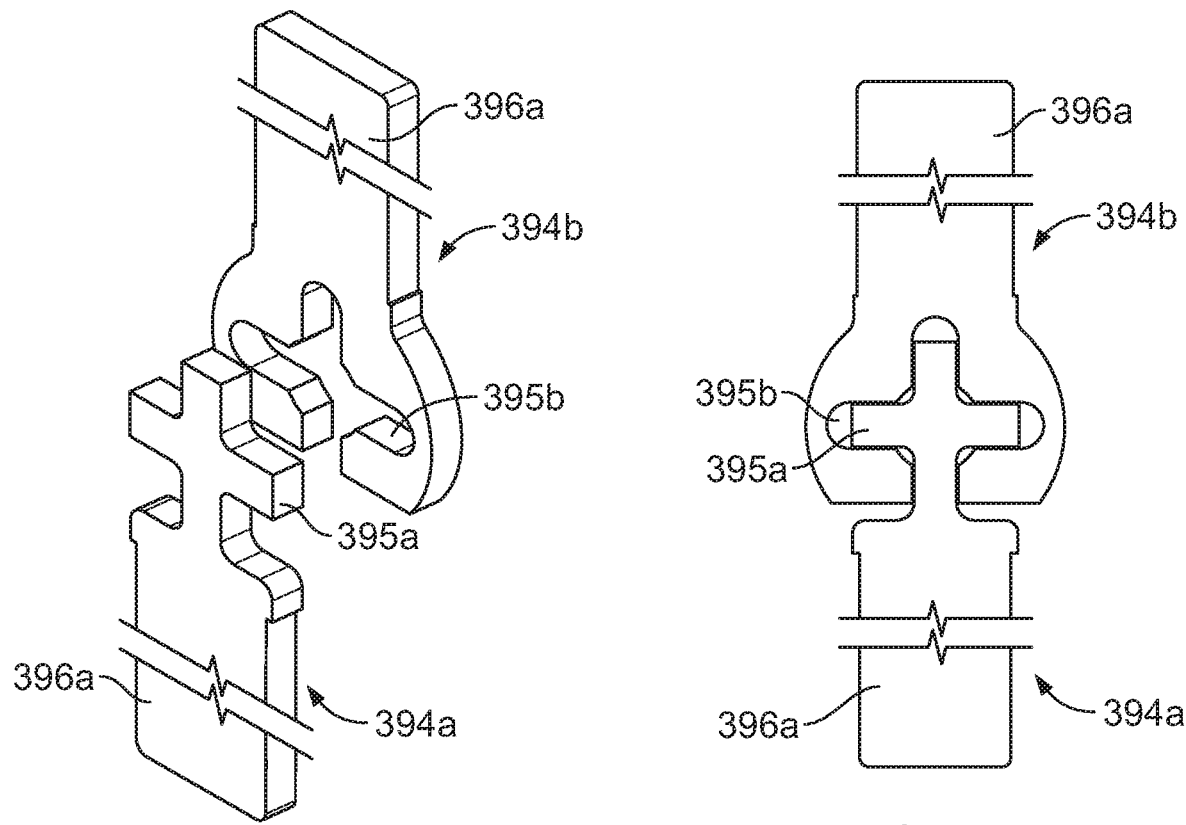
FIG. 22C
FIG. 22D
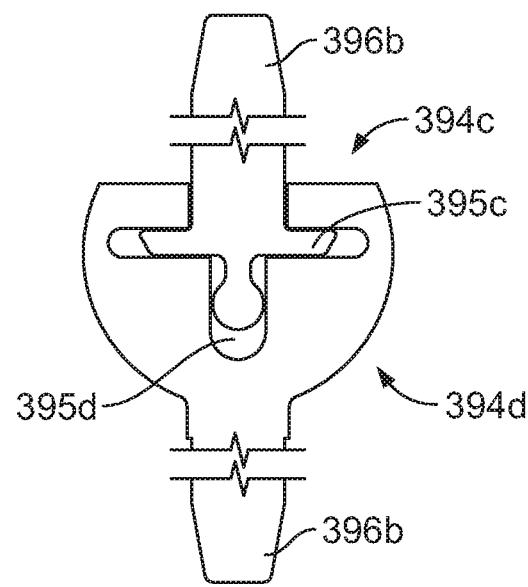
FIG. 22E

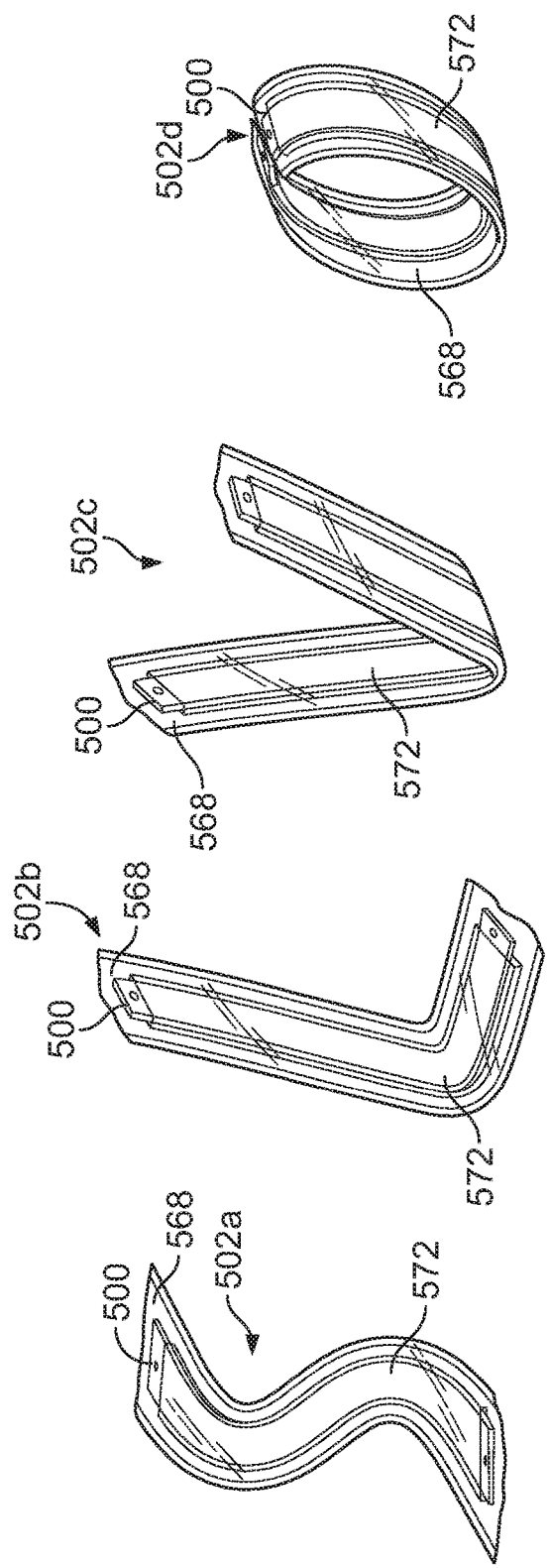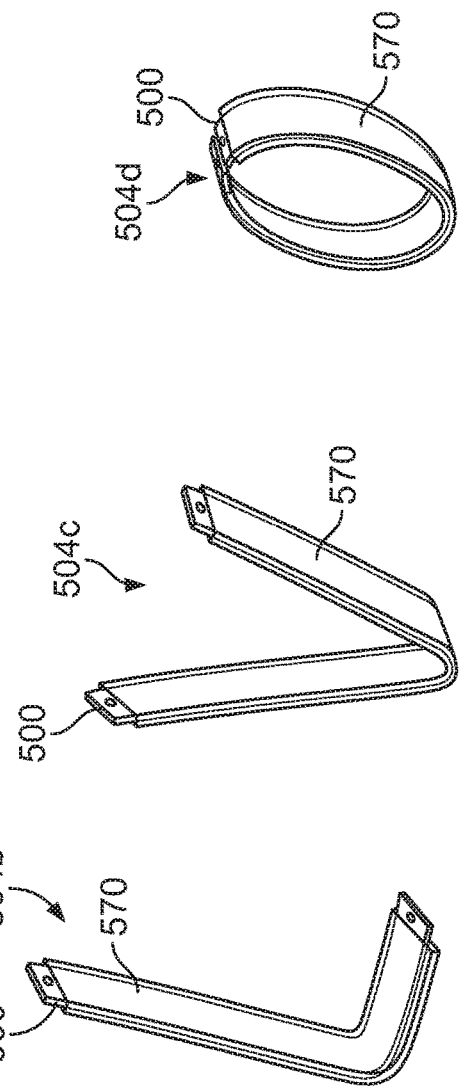

CURABLE, CONFORMABLE COMPOSITE PRECURSORS, CONFORMABLE CORE STRUCTURES, RESULTING PRODUCTS AND METHODS

FIELD OF THE INVENTION

The present invention in one aspect relates to a curable, conformable composite precursor having a conformable core structure. The curable composite is particularly suited to being conformed by hand to a desired shape or fit, maintaining its conformed shape and thereafter being cured in its conformed shape to a rigid form. The resulting cured structure can be used in a wide variety of applications and is particularly suited for orthotic and prosthetic devices. In another aspect, a conformable core structure is provided that can be conformed to and retain a desired shape and which core supports the curable composite material, which composite material may be a curable carbon fiber composite. The curable conformable composite can be manipulated manually or mechanically manipulated to a desired shape, cured to a final product or otherwise be incorporated into another product. Other aspects of the invention are the cured resulting product, the core structure, methods of making the core structure, the curable composite precursor and a packaged curable composite.

BACKGROUND OF THE INVENTION

Various types of custom-made products including custom-made orthoses are known. Those products are custom made to fit a patient and other products that are custom made to match an existing shape are often made conventionally by making a female cast around the relevant portion of a body having an existing shape. For a custom-made orthotic device, that may take place in an orthotist's office or lab. A male cast is then made of the female cast to provide a duplication of the original body portion. The male cast is then used to make the rigid orthosis or custom product, such as by overlaying a curable material such as a curable carbon fiber reinforced prepreg composite. The curable material must be compressed during the curing process for best results, so the mold and the curable material overlaying the mold are placed in a costly vacuum oven or autoclave for curing and a vacuum or pressure is applied during the curing. The above method is labor intensive, very costly and time consuming. In addition, the method may take several separate appointments and fittings, weeks apart, to complete during which time a patient or customer is deprived of the use of the orthosis or product.

A need exists for a method of custom making rigid orthoses and other products that match an existing shape, which method utilizes a fiber reinforced composite and is less labor intensive, faster, more efficient and more economical. In particular, a method of making a custom orthosis in a single day or single patient office visit would be very desirable.

A need also exists for methods and components that can be employed efficiently and reliably to produce rigid, custom orthoses and other products that are custom made to match an existing or a desired shape from a fiber reinforced composite.

SUMMARY OF THE INVENTION

The present invention in one aspect relates to a curable, conformable composite precursor having a conformable support or core structure in an initial shape or configuration. The curable composite is particularly suited to conforming, bending or shaping it to a desired shape or fit from the initial shape, retaining the desired shape and thereafter curing the conformed or shaped composite while in the desired shape to form a rigid form in the desired shape. The resulting cured structure in the desired shape can be used in a wide variety of applications and is particularly suited for orthotic and prosthetic devices. In another aspect, a conformable support or core structure is provided that can be conformed to and retain a desired shape and which core supports the curable composite material in that desired shape and cured to a rigid state while in the desired shape. The composite material may be a curable carbon fiber composite. The curable conformable composite can be readily manipulated manually, i.e., bent by hand, to a desired shape, cured while in the desired shape to a final product or otherwise be incorporated into another product. The precursor is typically packaged in a vacuum sealed bag or other suitable bag that is suitable for heat or UV curing and that does not lose vacuum during the full curing cycle. Other aspects of the invention are the cured resulting product, the conformable support or core structure, methods of making the support or core structure and the curable composite precursor and a packaged curable composite.

In accordance with one aspect of the invention, a curable, conformable composite precursor is provided that can be shaped, typically by hand, from an initial shape into a desired shape before being cured. The conformable support structure retains the desired shape during curing and the fabric follows the shape of the support. The precursor product is curable while in the desired shape, such as by heating or application of UV radiation, into a final product having that desired shape. The precursor product can be cured in the absence of an external vacuum or pressure above ambient pressure. In one embodiment, the precursor comprises a conformable fabric impregnated with an uncured resin, thermoset or UV-curable, in which a conformable support structure supports that impregnated fabric. The conformable support structure is plastically deformable or bendable from an initial shape in at least one or more locations in at least one direction. Such bending or deformation typically can be accomplished by applying a force such as that which is readily achieved by a person's hand. The curable, conformable composite precursor product further includes a compressor for compressing the fabric so that the fabric remains impregnated with the thermosetting resin during heating sufficient to fully thermoset the resin. The compressor contains or envelops the fabric and the conformable support structure and may provide a seal for those components from the atmosphere or surrounding environment for long-term storage. The precursor elements can be vacuum packaged to provide the compression.

In another embodiment, the conformable fabric is in the shape of a braided sleeve and the braided sleeve surrounds at least part of the conformable support structure. The braided sleeve typically will be sized or otherwise configured so that the braided sleeve can be readily placed over the conformable support structure as desired.

In one embodiment, the curable, conformable composite precursor may have an initial shape, generally in the form of a bar, a sheet or a more fully formed product, which may be, for example, an orthotic device assembly for a lower extremity, upper extremity or spine, for example.

When the composite precursor is cured, the impregnated fabric becomes the structurally supportive element of the cured precursor.

The conformable support or core structure, which may be present as an internal or central portion of the composite precursor or located externally thereof, allows the composite precursor to be formed into a desired shape prior to curing that is retained during curing. By use of the term core, it is not intended to imply or require that the core element be located interiorly or at a central location of the curable, conformable composite precursor. Indeed, it is contemplated that the "core" support structure could be used exteriorly of and for supporting the curable composite material, and in some embodiments could also be removed from the curable composite after curing. Various shapes and configurations for the support structure can be utilized. The conformable support structure may be a wire. The wire can be substantially straight, helical or can take the form of a waveform.

Alternatively, the conformable support structure can be in the form of a thin layer or a sheet of material, and the thin layer or sheet may be in a desired shape or configuration, and may contain various voids, perforations and/or raised areas to facilitate and/or restrict bending and/or shaping in a particular direction as desired. In one embodiment, the conformable support structure may be in the shape of an elongated rod or wire of material, typically metal that can be plastically deformed into a desired shape. Such plastic deformation occurs when the composite precursor is manually manipulated into a desired shape, which sometimes may be to conform or generally conform to the surface one wants to mimic or conform to. In the orthotic field, the composite precursor can be shaped to conform to a particular surface of a patient as desired, for example. Thus, the conformable support structure may be considered to be a malleable shaping core or skeletal structure although it need not reside interiorly of the impregnated fabric. Typically, the conformable support structure in one embodiment should be easily formed or shaped by hand into a shape suitable to form the desired device. The shaping operation thus may not require special molds or other forms but typically can be easily shaped directly over the surface to be mimicked. The conformable support structure should provide enough support or stiffness to resist undesired deformation during conforming the precursor including the impregnated fiber or fabric to the desired surface and to maintain the conformed shape after shaping is completed and during curing of the composite precursor after shaping. The shape of the conformable support structure may include geometries to encourage a specific bend radius or radii or directions of bending more easily than others as appropriate for the intended application of the composite precursor.

In addition, the conformable support structure may intrinsically include shapes to increase the size of the cross-section of the conformable support structure to increase strength and stiffness after the impregnated fabric is cured and also to facilitate plastic deformation as desired.

Alternatively, or in addition, a filler material may be added to the conformable support structure to increase the cross-sectional dimensions of the conformable support structure particularly when the conformable support structure is present as a core, that is, located interiorly of the conformable and uncured impregnated fabric.

To further increase the strength and stiffness of the composite precursor, the cross-sectional shape of the conformable support structure may be dimensionally increased such as by stamping. The stamped geometry can be configured such that the structural material bridges between the stamped features, thus increasing the cross-sectional dimensions when the impregnated fabric has been cured. This configuration can minimize cost, weight and complexity of the cured product.

Alternatively, a flexible material, such as polyurethane or a Nomex® honeycomb may be added over the conformable support structure to increase the cross-sectional dimensions.

The conformable support structure may also include an aesthetic pattern to improve the cosmesis of the final cured product and mechanical features to facilitate attachment of ancillary structures to the cured structure such as straps, padding, connectors, hinges, etc.

When the curable, conformable composite precursor is cured, the cured composite material is the primary structural material for the finished product providing its strength and stiffness. When in an uncured state, the structural material needs to be plastically deformable to permit desired shaping or conformance to a desired surface or other shape and to retain that desired shaping of itself and of the composite material after shaping and during curing to form the finished product or structural element in the desired shape. The resulting strength and stiffness of the cured product is determined by the strength and stiffness of the structural material in combination with its cross-sectional shape.

One material that is particularly suited for the curable composite material of the curable composite precursor is a fabric material having one or more plies which is pre-impregnated with a resin system. The fabric material may include a braided sleeve material. The braided sleeve material is advantageously a carbon fiber, aramid fiber, glass fiber or graphite fiber sleeve material that is pre-impregnated with a resin system. The resin system can be any suitable resin, e.g., one that suitably adheres to the fabric material when cured, including, for example, an epoxy that includes the proper curing agent. As a result, it is ready to be formed into a desired shape and retained in that shape by the conformable structural member and then cured while in that shape without the addition of a resin or curing agent. The pre-impregnated fabric material remains flexible at room temperature and may be stored, or cured for many months at room temperature. This material is hardened or cured by chemical activation through heating or by application of ultraviolet radiation in some cases. The cured composite precursor has high strength and stiffness.

To produce a cured high-strength composite precursor in accordance with the invention that has optimal strength and stiffness using a pre-impregnated fiber material, the curable conformable composite precursor should be compressed during the curing process. Any suitable structure for compressing the pre-impregnated curable conformable composite precursor can be utilized. Typical compressor structures for this purpose include shrink sleeves, tapes and vacuum bags to compress the pre-impregnated materials during curing.

Advantageously, the product package for the curable conformable composite precursor is also the compressor structure. The package/compressor may take the form of an elastic sleeve that applies compression to the pre-impregnated material and can be a shrink sleeve that operates to compress the pre-impregnated material when heated during oven curing at atmospheric or ambient pressure. Alternatively, a hermetically sealed (evacuated) bag or enclosing material can be utilized that is gas impermeable or substantially gas impermeable to maintain sufficient vacuum during curing to apply the desired pressure to the curable conformable composite material from the atmosphere during curing at atmospheric or ambient pressure. The hermetically sealed evacuated bag also serves as packaging for the curable conformable composite precursor. The bag may be made of any suitable material, particularly a film material, for holding a vacuum for long-term storage including, for example, polyurethane, polyethylene, nylon, Mylar and multiple layer films as desired. The hermetic seal and vacuum packaging may be created by any suitable vacuum and heat sealer such as an impulse sealer, direct or constant heat sealers, or band sealers. A second gas impermeable bagging film can be utilized over the vacuum bag to further enhance shelf life of the curable conformable composite. The package/compressor allows the curing to be done inside an oven at ambient (e.g., atmospheric) pressure instead of being at a vacuum or elevated pressure, which requires a vacuum oven or autoclave. The packaged curable conformable composite precursor can be formed into the desired shape, for example, such as to conform to a particular surface, which can be a person's leg, arm, back or other surface, while the curable conformable composite precursor is packaged. Thus, whatever the form of the packaging material, it should be sufficiently flexible so that it permits the curable conformable composite precursor to be shaped in a desired way, while maintaining compression to facilitate appropriate curing to a rigid form that corresponds to the form or desired shape.

The curable conformable composite precursor may be in the form of a simple bar or rod of material or may be a more complicated form as desired, such as a complete pre-fabricated device, which may be an orthotic device or component. If configured as a rod or bar of material, the curable conformable composite precursor can be shaped to conform to a surface or other shape as desired and thereafter attached, typically after curing, to other members to build an orthosis or other device. If an orthotic device is contemplated, the curable conformable composite precursor would typically be configured to conform or otherwise suit a particular part of the body, such as the leg, arm or spine, for example. In accordance with this aspect of the invention, the curable conformable composite precursor, which typically would be packaged as previously described, would be directly formed on the body part for which it is intended. Adjustments to its shape can be easily accomplished by virtue of the conformable nature of the curable conformable composite precursor so that its shape can be optimized as desired prior to curing into a fixed shape. Thus, when the shape of the curable conformable composite precursor is deemed appropriate, it retains that shape and can then be cured to a rigid product and incorporated into the desired orthotic or other device.

In accordance with one aspect of the invention, the curable, conformable composite precursor is provided that is manually manipulable into a desired shape before being cured and then curable by heating without a vacuum while retained in that shape by the conformable support structure and into a final product having the desired shape. The precursor includes a conformable fabric that is impregnated with an uncured thermosetting resin that typically will also include a proper curing agent. A conformable support structure for supporting the impregnated fabric forms part of the curable conformable composite precursor, the support structure being plastically deformable at one or more locations in at least one direction by hand, which in turn also deforms the impregnated fabric and retains the fabric in that desired position. In addition, a compressor is provided for compressing the fabric so that the fabric remains impregnated with the resin during heat curing sufficient to fully thermoset the resin, the compressor typically containing the fabric in a conformable support structure, although it is contemplated that the support structure could reside exteriorly of the compressor with the pre-impregnated fabric being contained within the compressor. In such an embodiment, the conformable support structure could be removed from the cured impregnated fabric.

In one embodiment, the compressor is vacuum packaging that encloses the other elements (the conformable support structure and the resin-impregnated fabric) of the precursor is a vacuum-shrink wrap configuration.

During curing, atmospheric or ambient pressure is automatically utilized to maintain the prepreg fibers under a suitable curing pressure of about 15 pounds per square inch. Alternatively, the compression may be provided by an elastic material or sleeve that envelops the other components of the precursor.

In one embodiment, the fabric can be in the form of a braided sleeve of suitable material, which may be carbon fiber and the sleeve may surround all or part of the conformable support structure. The fabric may also be utilized as a strip of material that can be wound along or around the conformable support structure.

Various types of support structures can be utilized. The support structure should be plastically deformable by hand at one or more locations in at least one direction to provide a desired conformance of the curable conformable composite precursor. The conformable support structure can be a wire, a rod, a relatively thin metal layer or sheet and combinations thereof. The wire can be substantially straight, substantially helical or in a waveform pattern. The conformable support structure can have an initial shape as desired which can be straight, curved, planar or any other desired suitable shape. When the support structure comprises a sheet of material, which may be a suitable type of metal, typically it can be plastically conformed by hand. In that regard, to facilitate such plastic deformation by hand, the thin layer or sheet may include one or more elongated voids for facilitating plastic deformation. The sheet or thin layer may also include open-ended voids to facilitate such plastic deformation. In one embodiment, the open-ended voids form a zig-zag pattern in the plane of the sheet or a serpentine pattern in the plane of the sheet. A plurality of substantially parallel elongated voids or a pair of opposed elongated voids may be present in the sheet to facilitate the desired plastic deformation by hand. In addition, the sheet may comprise one or more ridges for resisting plastic deformation in one or more directions. The ridges may also increase the rigidity of the finished product. A plurality of substantially parallel elongated voids may be provided across the ridge or ridges. The plastically deformed support structure, which may be a thin layer or sheet, needs to have sufficient stiffness to retain itself and the impregnated fiber in the deformed or conformed position both after plastic deformation and during curing of the impregnated fiber.

In accordance with another aspect of the invention, the fiber material that is utilized in the pre-impregnated fiber may be any fiber suitable for making a cloth for making a composite including, for example, glass fiber, carbon fiber, graphite fiber, aramid fiber, silicon carbide fiber, cellulose fiber, ductile metal fiber and mixtures or combinations thereof.

Typically, but not necessarily, the curable conformable composite precursor is plastically deformed to match part of a body of a person prior to curing. However, it is to be understood that the initial shape of the curable conformable composite precursor may be the final desired shape, in which case no further shaping may be required prior to curing to a rigid member.

In accordance with another aspect of the invention, the curable, conformable composite precursor may include first and second release forms, wherein the fabric is in the form of a fabric layer, the first release form or layer being located between the conformable support structure in the fabric layer and the second release form or layer located opposite the first release form or sheet across the fabric layer. The release forms or sheets are optional because the compressor can have inherent release properties or because it is desirable for the compressor to be part of the final product as a cosmetic covering.

In accordance with another aspect of the invention, the curable, conformable composite precursor that is curable to a rigid product having a desired shape is provided. The precursor includes a conformable fabric that is impregnated with an uncured liquid or fluid resin, thermoset or UV-curable, a conformable core structure supporting fabric, the core structure being plastically deformable at one or more locations in at least one direction and a packaging material enclosing the fabric from the atmosphere. This permits the fabric to remain impregnated with the resin including during storage, shaping and curing. The packaging material that encloses the pre-impregnated fabric permits the fabric to be shaped as desired prior to curing without the resin making unwanted contact with a person's skin or other surface to which the curable, conformable composite precursor is to be conformed. Such a packaging arrangement also allows the curable, conformable composite precursor to cure better while in the desired shape resulting in an improved product compared to a product that has not been so packaged if the packaging arrangement provides compression to the rest of the precursor. If the packaging arrangement is a hermetically sealed vacuum package, the shelf life of the resin is longest. Typically, the conformable core structure that supports the fabric is located within the fabric but the conformable core structure in some embodiments may be located exteriorly of the conformable impregnated fabric and in some embodiments can reside outside of the packaging material.

It is to be understood that the packaging material may also function as a compressor.

A filler material may be provided within the conformable impregnated fabric so that the conformable impregnated fabric has a desired cross-sectional shape. The conformable core structure may reside within the fabric or exteriorly of the fabric. The filler material may be a foamed polymer that is flexible so that it is conformed to the remainder of the curable conformable composite precursor. Other types of fillers, including particulates and unfoamed or foamed polymers can also be utilized.

The conformable core structure of the curable composite precursor may comprise an elongated body of substantially uniform cross-section. Alternatively, the core may be a body or an elongated body of a non-uniform cross-sectional shape. Such a variation in the cross-sectional shape can be used to facilitate or to restrict bending and plastic deformation in certain regions as desired as well as to facilitate bending and plastic deformation in other regions. Such an arrangement can be useful when it is known in advance the nature of the conformance that is desired from the initial shape.

In accordance with another aspect of the invention, a curable, conformable bar stock member having an initial shape and curable into a rigid product having a desired shape different from the initial shape is provided. The curable, conformable bar stock includes a conformable fabric that is impregnated with the uncured thermosetting resin which also typically includes a proper curing agent. The curable, conformable bar stock member also includes a conformable support structure for supporting the impregnated fabric, the support structure being plastically deformable at one or more locations in at least one direction by hand and a packaging material enclosing the impregnated fabric. In one embodiment, the packaging material encloses the impregnated fabric and the conformable support structure whereas in another embodiment the packaging material encloses only the impregnated fabric with the conformable support structure located exteriorly of the packaging material. In another embodiment, the packaging material for the bar stock member is a compressor for compressing the fabric so that the fabric remains impregnated with the resin. The packaging material of the bar stock member may be the compressor for compressing the fabric so that the fabric remains impregnated with the resin including during curing, for example. In accordance with another aspect of this embodiment, the packaging material of the bar stock member encloses the conformable support structure.

In accordance with another aspect of the invention, a curable, conformable sheet stock member having an initial shape and being curable into a rigid product having a desired shape, different from the initial shape is provided. The curable, conformable sheet stock is composed of a conformable fabric impregnated with an uncured thermosetting resin, a conformable support structure for supporting the impregnated fabric, the support structure being plastically deformable at one or more locations in at least one direction by hand and packaging material that encloses the fabric. The deformed support structure retains itself, the impregnated fabric and the packaging material in the desired shape including during curing of the impregnated fabric. In accordance with another aspect of this embodiment, the packaging material is a compressor for compressing the fabric so that the fabric remains impregnated with the resin. Typically, the compressor will also compress the fabric during heating to facilitate proper thermosetting of the resin in the fabric, with the compressor containing the fabric and the conformable support structure. It is to be understood that in an alternative embodiment, the compressor may only contain the fabric impregnated with the thermosetting resin and typically the curing agent with the conformable support structure being on the exterior of the compressor and/or packaging material. In accordance with another embodiment, the packaging material encloses the conformable support structure of the curable, conformable sheet stock member. In accordance with another aspect of the invention, a conformable support structure is provided that includes a plurality of connected elongated members, the members partially enclosing the void and being plastically deformable at one or more locations in at least one direction by hand, the support structure being substantially planar. The conformable support structure may further include a ridge extending along at least part of the length of one of the elongated members. A plurality of elongated voids may be provided across the ridge. In accordance with another aspect of this embodiment, the support structure further includes the furrow substantially parallel to the ridge in the same member in which the ridge is located.

In accordance with another aspect of the support structure, at least one of the members has a plurality of open-ended voids at or adjacent the extremity of the member for facilitating plastic deformation of the member at the extremity rotationally around an axis perpendicular to the plane of the conformable support structure.

In accordance with another aspect of the conformable support structure, one of the members has a serpentine portion remote from the two extremities of one of the members for facilitating plastic deformation of that member in a lengthwise direction.

In accordance with another embodiment, the conformable support structure includes a ridge at a connection of members for resisting plastic deformation across the ridge.

In accordance with another aspect of the conformable support structure, two opposed voids are provided at a connection of members for encouraging plastic deformation at the connection.

In accordance with another aspect of the support structure, the support structure has the desired overall shape, which may be trapezoidal, rectangular, circular, triangular, an isosceles trapezoid and a right trapezoid, for example.

In accordance with another aspect of the invention, a method of making a custom-shaped product from a precursor that includes the conformable fabric impregnated with an uncured thermosetting resin, a conformable support structure for supporting the impregnated fabric, the support structure being plastically deformable at one or more locations in at least one direction by hand and a compressor for compressing the fabric so that the fabric remains impregnated with the resin during curing, the compressor containing the fabric and the conformable support structure, the method includes deforming the precursor including plastically deforming the conformable support structure to conform the curable conformable composite precursor to a desired shape and curing the precursor while in the desired shape to form a rigid product in the desired shape. The plastic deformation of the conformable support structure may be performed to conform the curable, conformable composite precursor to at least part of the surface of an object, which may be, for example, a person's limb, spine or other body part.

Depending on the type of resin, the curing may comprise either thermal or ultraviolet curing.

The method of making a custom-shaped product may further include adding a strap to the cured precursor and/or in the deforming of the precursor to conform to a desired shape comprises deforming the precursor to conform to a surface of a mammal, which may be a person.

In accordance with one aspect of this invention, the deforming the precursor may comprise deforming the precursor by an orthotist and curing the precursor includes thermally curing in an oven without an externally-applied vacuum or elevated pressure, which may occur in the orthotist's office or other location, as the compressor element of the precursor supplies the desired pressure during curing, either from atmospheric pressure in the case of a vacuum packaged precursor or elastic pressure in the case of an elastic sleeve containing precursor.

In accordance with another aspect of this embodiment of the invention, the conformable support structure includes a substantially planar, zig-zag portion and the plastic deforming of the precursor to conform to the desired shape includes bending the zig-zag portion rotationally around an axis perpendicular to the plane of the zig-zag portion. The conformable support structure may include a serpentine portion and the deforming of the precursor to conform to a desired shape or an object includes elongating the serpentine portion.

In accordance with another aspect of this embodiment, the conformable support structure comprises a plurality of substantially parallel slots and the deforming the precursor to conform to the desired shape includes bending the conformable support structure around an axis parallel to the plurality of slots.

In accordance with another aspect of this embodiment of the invention, the conformable support structure may include one or more non-straight wires and the deforming the precursor to conform to the desired shape or to an object includes extending or shortening the conformable support structure by extending or compressing the non-straight wires. The non-straight wires may be three-dimensional such as helical or be substantially planar in a waveform pattern such as sinusoidal, square wave, triangle wave, serpentine, alternating chained semicircles or substantially similar shapes.

In accordance with another aspect of this embodiment, the conformable support structure comprises a wire and the deforming the precursor to conform to the desired shape comprises bending the wire.

In accordance with another aspect of the invention, a custom-shaped product having a desired shape is provided, the product comprising a fabric, which may be a fabric sleeve, impregnated with a cured resin and a conformable core structure adjacent the fabric and which may be located inside or outside of the sleeve, the conformable core structure having been plastically deformed from an initial shape to conform to the desired shape. In accordance with another aspect of this embodiment, the custom-shaped product further includes a polymer filler at least partially surrounded by the fabric, wherein the conformable core structure is composed of a wire at least partially surrounded by the polymer filler. In accordance with another aspect of this embodiment, the conformable core structure is a wire and the wire may be substantially helical. Alternatively, the conformable core structure may comprise a sheet of plastically deformable material which material may be a metal. The sheet may comprise an elongated void for facilitating plastic deformation as well as a plurality of open-ended elongated voids that form a zig-zag pattern in the plane of the sheet or in a serpentine pattern in the plane of the sheet. The voids may be a plurality of substantially parallel elongated voids or a pair of opposed elongated voids in the plastically deformable sheet. In accordance with another aspect of this embodiment, the sheet may include a ridge for resisting plastic deformation and the sheet may further include a plurality of substantially parallel elongated voids across the ridge.

In accordance with another aspect of this embodiment, the fabric may be any suitable fabric for making a composite including, for example, glass fiber, carbon fiber, graphite fiber, aramid fiber, silicon carbide fiber, cellulose fiber, ductile metal fiber and mixtures or combinations thereof.

In accordance with another aspect of this embodiment, the custom-shaped product may further include one or more straps and the product may be an orthosis.

BRIEF DESCRIPTION OF THE DRAWINGS

FIGS. 10-13 illustrate a conformable support structure or core member having a specially configured cross-sectional shape.

FIG. 10 is a side elevation view of the core member in position to be bent to conform to a body surface.

FIG. 11 is a top plan view of the core member of FIG. 10.

FIG. 12 is a sectional view along line I-I of FIG. 11.

FIG. 12A is a sectional view of a curable and conformable composite precursor incorporating the core member of FIG. 12.

FIG. 13 is a perspective view of the conformable core member of FIG. 10.

FIG. 14 is a side elevation view of the conformable core member.

FIG. 15 is a top plan view of the conformable core member of FIG. 14.

FIG. 16 is a sectional view along line II-II of FIG. 15.

FIG. 17 is a perspective view of the conformable core member of FIG. 14.

FIG. 18 is a side elevation view of the conformable core member.

FIG. 19 is a top plan view of the conformable core member of FIG. 18.

FIG. 20 is a sectional view along line III-III of FIG. 19.

FIG. 21 is a perspective view of the conformable core member of FIG. 18.

FIG. 22C shows in perspective the alignment of male and female connectors for attaching the two precursor portions of FIG. 22B.

FIG. 22D is an elevation view of the male and female connectors of FIG. 22C in mating relationship.

FIG. 22E is an elevation view of alternative male and female connectors in mating relationship.

FIGS. 25-35 illustrate two linear frames, a composite precursor, customized composite precursors and finished structures.

FIG. 25 is a top plan view of a linear conformable support structure or core member.

FIG. 26 is a top plan view of another embodiment of a conformable linear support structure or core member.

FIG. 27 is a top plan view of a packaged conformable and curable composite precursor having incorporated therein the conformable linear core member of either FIG. 25 or FIG. 26.

FIGS. 28-31 illustrate in perspective view the curable conformable composite precursor of FIG. 27 conformed to different shapes.

FIGS. 32-35 each illustrate in perspective view a different finished, custom structure based on the conformed precursor shape of FIGS. 28-31, respectively.

DETAILED DESCRIPTION OF THE INVENTION

The invention is capable of almost unlimited types of products and uses in innumerable applications. The inventions disclosed herein are particularly suited for use in custom or form-fitted devices where rigid and strong structural components thereof are needed. One important advantage of the present inventions is that low-cost, custom-fitted or conformed rigid structural components can be easily, quickly, accurately and economically made. Such structural components can be useful in a wide variety of products. The curable composite precursor devices of the invention can be made in a wide variety of shapes, including as non-limiting examples, bar stock, sheet, specific forms, shapes as desired, and custom formed or conformed shapes. The inventions described herein are particularly suited for making custom orthotic devices but are also suited for making custom formed or shaped devices for a wide variety of uses and products. Other specific applications of the invention include custom seating and positioning systems, including for radiation, oncology and other medical positioning systems, custom or prefabricated sports equipment, including hockey sticks, ball bats and other equipment, for example.

While the inventions and embodiments described below are primarily directed to orthotics and orthotic components, it is to be understood that the inventions disclosed herein are useful in a wide variety of devices and for structural device components.

Single-Upright Ankle-Foot Orthosis

Figures 1, 1A:
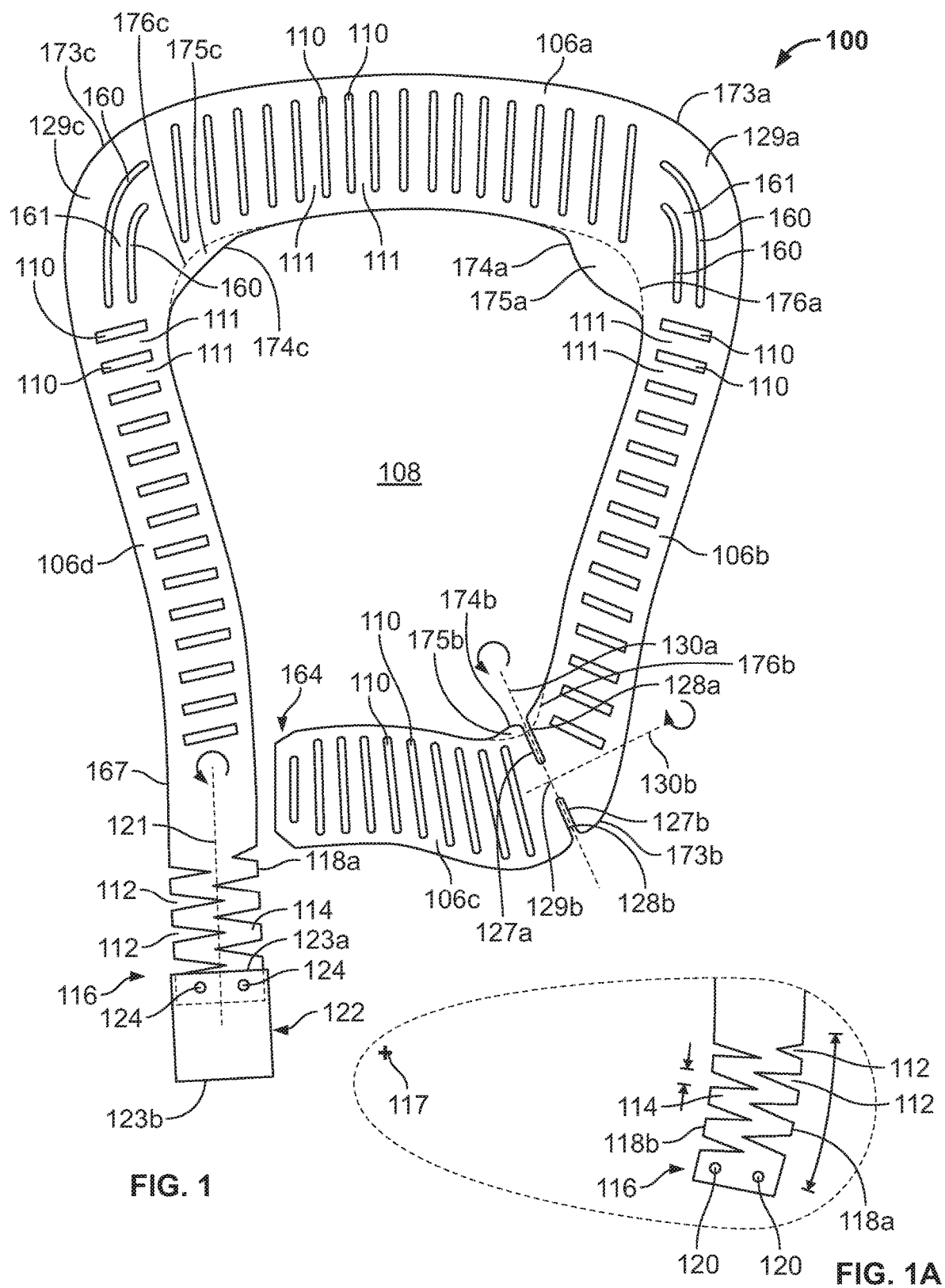
FIG. 1 is a front elevation view of a conformable support structure or core that can be used in making a single upright ankle-foot orthosis.
FIG. 1A is a fragmentary view of a zig-zag portion of the conformable core of FIG. 1.

Referring to FIGS. 1-4 generally, in one embodiment of the invention, a conformable support member or core 100, a curable conformable composite precursor 102, and an ankle-foot orthosis 104 with a single upright are illustrated. Conformable core 100 is illustrated in FIG. 1. Conformable core 100 has four lateral portions 106a-d laid out in a substantially trapezoidal arrangement. Portions 106 may be straight, substantially straight or may be curved. Conformable core 100, which is a conformable support structure, almost completely or fully encloses a void 108. Conformable core 100 is plastically deformable by hand, can be made from any suitable plastically deformable material such as malleable metals, polymeric materials, fiber materials. Core 100 may be made from a plurality of materials including materials that are not plastically deformable as long as one or more of the materials are plastically deformable. Most preferably, core 100 is made from sheet metal, typically as a unitary frame stamped or cut from a single metal sheet. Alternatively, separate members may be used and joined together. The sheet metal can be any suitable malleable or ductile metal such as copper, aluminum or steel, particularly mild steel. Conformable core 100 is substantially planar.

Each of lateral portions 106a-d of conformable core 100 may include voids for promoting or more readily permitting and directing plastic deformation of the portion. Here, lateral portions 106a-d each has elongated voids 110 in the shape of slots within the members. Within one portion 106, elongated voids 110 are separated by lands 111 and are substantially parallel to the width of the member where the void is located. In addition, elongated voids 110 are substantially parallel to each other within one portion 106 with some deviation possible from perfect parallelism due to curvature of the member, particularly portion 106c. Elongated voids 110 may be present along substantially the entire length of a portion as in portion 106c, may be confined to a middle section as in portions 106a and 106d, or may extend almost to one end, but not to the other as in portion 106b. Voids 110 promote plastic deformation by manual manipulation of lateral portions 106 in a direction perpendicular to portion 106 (as illustrated in FIG. 10 for member 131) around an axis parallel to the length of voids 110. Typically, the manual manipulation readily can be accomplished by a person's hands. As will be discussed later, lateral portions 106 may have a profile to control or prevent deformation in other directions.

Another example of voids is open-ended voids 112, frequently elongated that are not fully enclosed by portion 106d. Voids 112 are typically triangular and may be arranged in an alternating pattern so that portion 106d has a zig-zag 114 at extremity 116 of portion 106d. Zig-zag 114 promotes plastic bending around an axis 117 perpendicular to the plane of extremity 116 (and generally of portion 106d and conformable core 100). Such bending generally causes side 118a to extend and opposed side 118b to contract as illustrated in FIG. 1A. Additionally because there is generally less material in zig-zag 114, plastic bending around an axis parallel to the plane of extremity 116 is also possible as well as plastic twisting around an axis 121 extending through zig-zag 114, substantially perpendicular to the width of extremity 116. Zig-zag 114 is particularly useful in extremity 116 because extremity 116 also has attachment apertures 120. Zig-zag 114 may be located elsewhere or at additional locations in conformable core 100 where allowing the two or three kinds of plastic bending is desirable.

Figure 4:
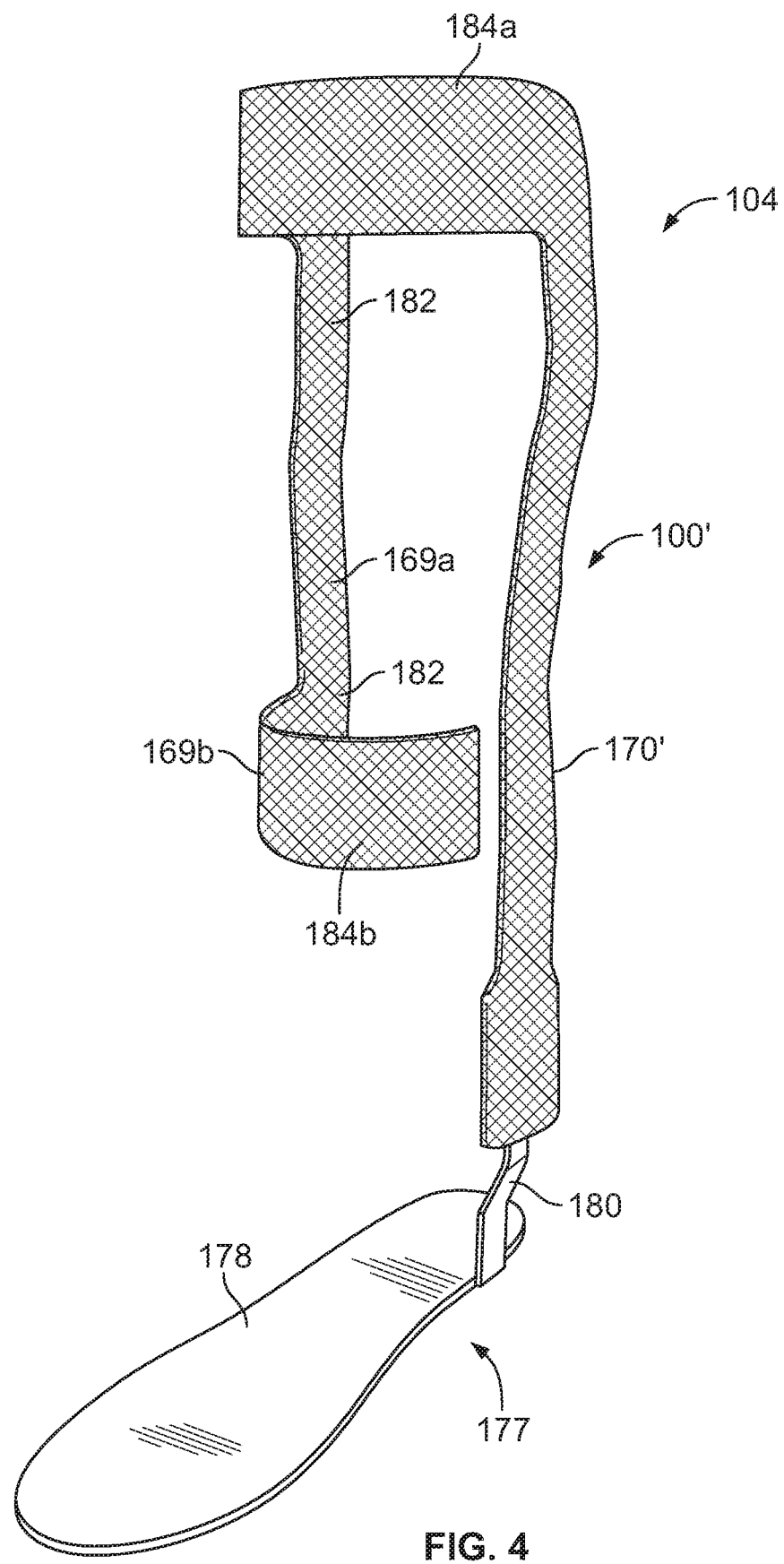
FIG. 4 is a perspective view of a cured, custom single-upright ankle-foot orthosis based on the precursor of FIG. 3.

Attachment apertures 120 (shown in FIG. 1A) are used to attach a hollow upper bar acceptor 122 with fasteners such as screws (not shown). Bar acceptor 122 is used to connect conformable core 100 to a footplate or ankle component. Bar acceptor 122 may be of any suitable structure. Preferably, bar acceptor 122 has a cavity and has open ends 123a and 123b for receiving extremity 116 and a riser for the footplate (as seen in FIG. 4) or an ankle component. Alternatively, either or both ends 123a and 123b could be male rather than female. Bar acceptor 122 may have two or more apertures 124 as shown in FIG. 1. Two of apertures 124 may be threaded for screw attachment of bar acceptor 122 to conformable core 100. Bar acceptor 122 may be made of any suitable material. Bar acceptor 122 is shown as being rectangular cubic, but it can have any suitable shape such as rectangular cubic with rounded corners or truncated corners.

Referring to FIG. 1, a third type of void for promoting or more readily permitting plastic deformation are voids 127a,b in the shape of slots having open ends 128a,b. Voids 127 are located at connection 129b of portions 106b and 106c. Unlike voids 112, voids 127a and 127b are opposed. Voids 127 allowing plastic bending around an axis 130a parallel to voids 127 similar to voids 110, axis 130a being in the plane of flat portions 106b and 106c, but need not be. Voids 127 also allow limited bending around a second axis perpendicular to the plane of portions 106b and 106c (similar to bending of zig-zag 114 around axis 117) and around an axis 130b substantially perpendicular to the length of voids 127 and within the plane of connection 129b similar to zig-zag 114 (similar to bending of zig-zag 114 around axis 121).

The profile of lateral portions 106 may be flat with flat lands 111 as indicated by FIGS. 1-4. Alternatively, lateral portions 106, voids 110 and lands 111 may have the shape of lateral members 131, 132 and 134 illustrated in FIGS. 10-13, 14-17, and 18-21, respectively. Lateral member 131 has a substantially central ridge 136 extending along the length of the member having elongated voids 110a. While voids 110a promote plastic bending of member 131 around an axis 138 parallel to the length of voids 110a, ridge 136 resists bending around an axis perpendicular to the length of voids 110a. The combination of ridge 136 and voids 110a thus serve to selectively provide and limit the readily deformable portions of member 131 to deformation (i.e., bending) around axes perpendicular to the length of voids 110 such as axis 138. As illustrated in FIG. 10, member 131 is being bent to match the shape of a body B with arrows F illustrating the bending forces on member 131. Axis 138 is located at the center of curvature of body B where it is contacted by member 131. As member 131 (or portions 106) is bent around body B there can be different axes or centers of curvature for different parts of the member. Ridge 136 may be stamped into member 131. Ridge 136 includes lands 111a having a raised portion 140a.

In the illustrated embodiment, lateral member 131 has a width 142a of 0.900", void 110a has a length 144a of 0.620" and a width 146a of 0.125" and voids 110a are spaced at a distance 148a center on center of 0.375".

Lateral member 132 has a ridge 136 and a valley 154, both extending along the length of the member having elongated voids 110b. Lands 111b between voids 110b of lateral member 132 have a raised portion 140b and a depressed portion 156. Lands 111b, voids 110b, and lateral member 132 can have the same dimensions as those of lateral member 131. In other words, dimensions 142b, 144b, 146b and 148b can be the same as dimensions 142a, 144a, 146a and 148a, respectively.

Lateral member 134 has opposed ridges 136 and 158, both extending along the length of the member having elongated voids 110c. Lands 111c between voids 110c of lateral member 134 have a raised portion 140c. Lateral member 134 is illustrated with a single type of land 111c, but they are alternately raised in opposed directions. However, it is not necessary that they have this alternation pattern and ridges 136 and 158 need not be raised the same amount. In this illustrated embodiment, lateral member 134 has a width 142c of 0.900", void 110c has a length 144c of 0.620" and a width 146c of 0.025" and voids 110c are spaced at a distance 148c center on center of 0.125". Generally, lateral members 131, 132, and 134 can have any suitable length or width needed for a given application. Typically, the width of members 131, 132 and 134 will be within a range of about 0.125" to about 3" (about 3 mm to about 76 mm) and preferably within a range of about 0.5" to about 2" (about 12 mm to about 51 mm).

As a general matter, finer spacing of slots and voids facilitate finer shaping, fitting or conforming of conformable core 100. The shape, orientation and arrangement of slots, voids and other features guide the shaping of the frame for smoothness in certain areas, small or large bend radii in other areas, directionality of contouring, etc. The shape of these slots, voids and other features may also be designed to add cosmesis to the final construct after curing.

Conformable core 100 has connections 129a and 129c connecting portions 106a and 106b and portions 106a and 106d, respectively. Connections 129a and 129c have curved voids 160 on either side of land 161. Land 161 may have ridges or valleys to stiffen connections 129a and 129c to decrease the likelihood of plastic bending at connections 129a and 129c.

Lateral portions 106 collectively have two unconnected ends, extremities 116 and 164.

Figure 2:
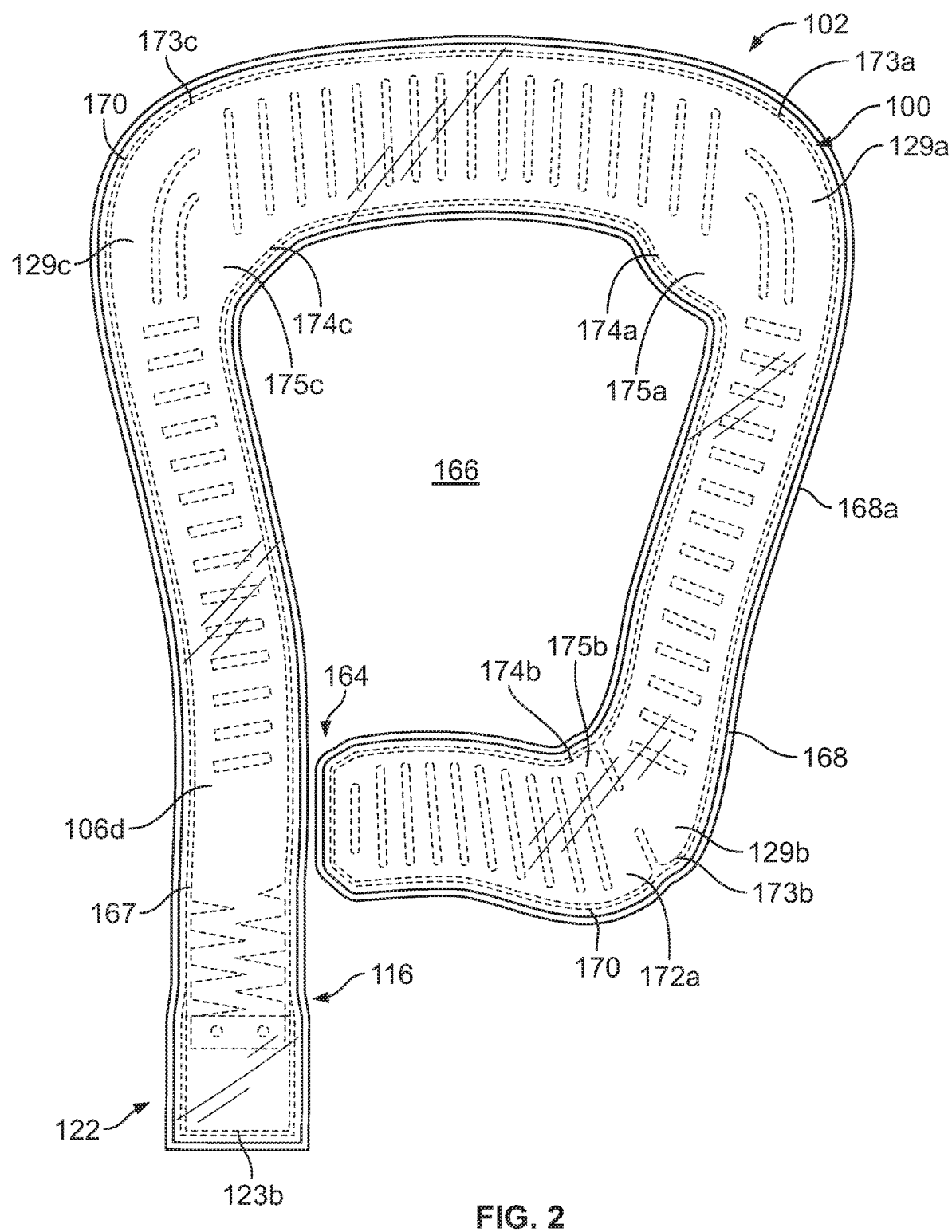
FIG. 2 is a front elevation view of a curable conformable composite precursor including having the conformable core of FIG. 1 incorporated therein.

FIG. 2 illustrates a precursor 102 based on conformable support member or core 100, which is shown in phantom. Precursor 102 has a compressor, which is illustrated as a sealed vacuum bag 168. Generally, the compressor may be any suitable compressor including a shrink tape, shrink tubing, an elastic storage sleeve or a vacuum bag. The compressor may have release properties such as a silicone or other suitable coating or being made from silicone allowing the compressor to be removed from the cured product. The compressor allows curing of the prepreg fibers in a non-vacuum or atmospheric pressure oven, i.e., a normal inexpensive oven.

Figure 3:
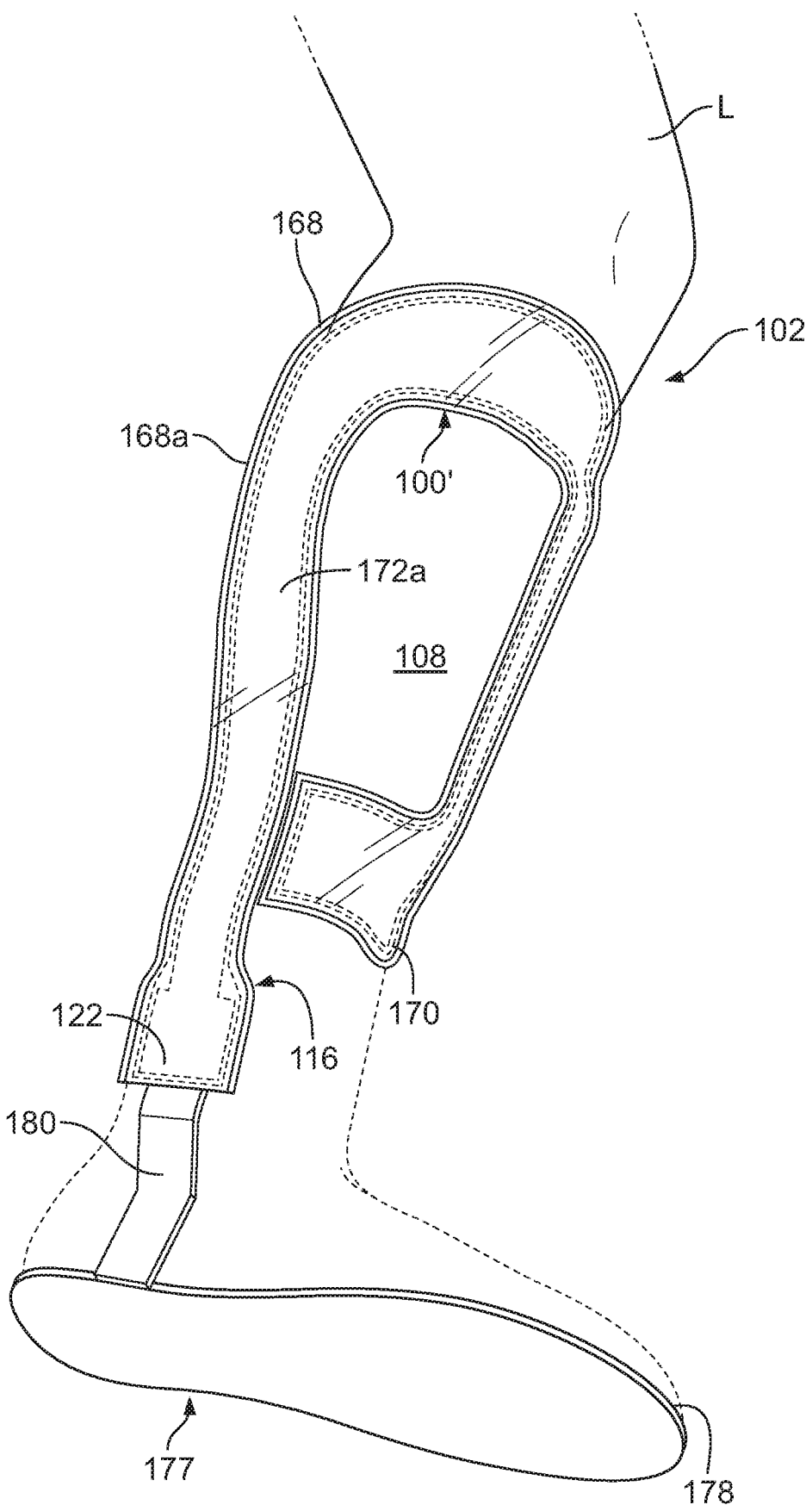
FIG. 3 is a perspective view of the curable conformable composite precursor of FIG. 2 having been conformed to fit around a leg of a patient.
Figure 22A:
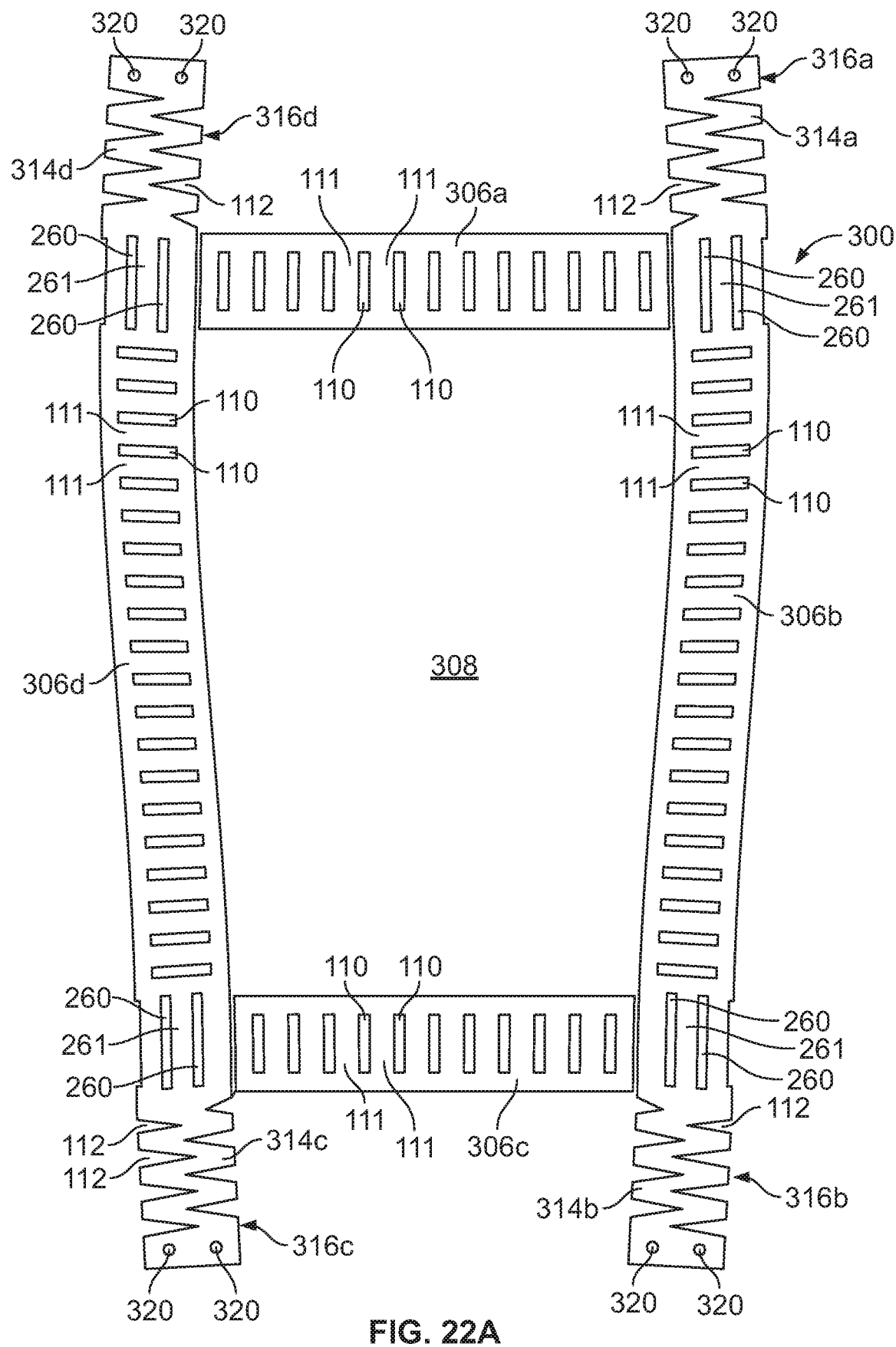
FIG. 22A is a front elevation view of a conformable support structure or core lower leg portion for a knee-ankle-foot orthosis of FIG. 22F.

Alternatively, the compressor can serve as a cosmetic layer in the finished product and it bonds to fiber layers 169 during curing. Vacuum bag 168 may be of any suitable material particularly one that holds a vacuum and can be hermetically sealed with seal 168a as illustrated or double seals 168a. The bag may be made of any suitable material, particularly a film material, for holding a vacuum for long-term storage including, for example, polyurethane, polyethylene, and Mylar and is preferably thermobondable. Preferably, the material is Stretchlon®. Preferably the material of bag 168 has a thickness of about 0.003" to about 0.010". Hermetic seals 168a may be created by any suitable sealer, particularly a heat sealer such as an impulse sealer, a direct or constant heat sealer, or a band sealer. Vacuum bag 168 may tightly fit precursor 102 as shown in FIG. 2 and have a void 166 corresponding to void 108 in core 100. Alternatively, it may loosely fit around precursor 102 and not have void 166. Bag 168 extends into bar acceptor 122 through open end 123b so that bar acceptor 122 can receive, for example, a riser 180 as shown in FIG. 3. Vacuum bag 168 may contain a port (not shown) typically of the same material as bag 168 for applying a vacuum to bag 168. In one embodiment, the port may simply extend beyond acceptor 122, sealed in the same way as bag seal 168a, and is pushed into acceptor 122 once the bag is evacuated of air for receiving riser 180. An alternative method of connecting precursors to objects outside to a vacuum bag or compressor is discussed later with reference to FIGS. 22B-D; this alternative method could be used with core 100. FIG. 12A illustrates a typical cross-section of a precursor 102a including two flexible fiber layers 169, preferably from a sleeve 170 of the fiber material. Alternatively, a prepreg fiber cloth may be wrapped around the members of the frame.

Referring to FIG. 2, in making precursor 102 from conformable core 100, a pre-impregnated braided fiber sleeve 170 (shown in phantom) is pulled over bar acceptor 122, end 116 of conformable core 100, around conformable core 100, and over the other end 164 or vice-versa. In an alternative to FIG. 2 (not shown), the end 164 of the sleeve 170 may extend further so that it extends over all or part of portion 106d, thereby fully enclosing void 166, which generally may be in the plane of conformable core 100 or the plane of precursor 102. It may also be folded over edge portion 167 of portion 106d. Conformable core 100 and bar acceptor 122 are therefore enveloped by sleeve 170. As shown in FIG. 12A, sleeve 170 is adhered to the underside of ridge 136 at location 171, but this is not necessarily the case.

Figure 54:
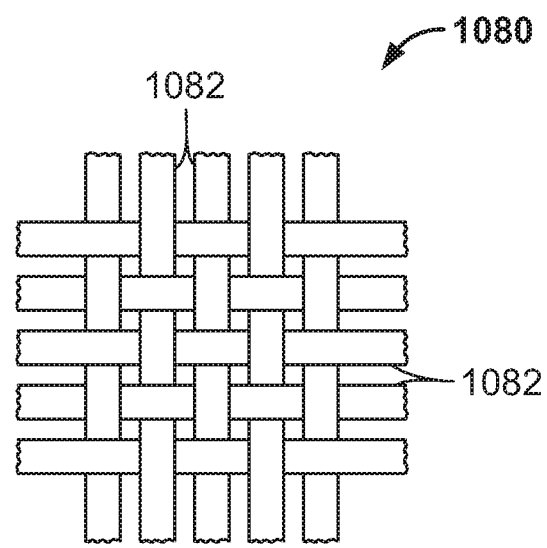
FIG. 54 is a schematic view of a mesh that is a useful material for conformable support structures and frames.

Sleeve 170 includes a braid of three or more yarns of a suitable fiber for reinforcing the cured composite material. Suitable reinforcing fibers include glass fiber, carbon fiber, graphite fiber, aramid fiber, silicon carbide fiber, cellulose fiber, silicon carbide fiber and mixtures thereof. Aramid may include meta-aramid such as Nomex®, para-aramid such as Kevlar®, and mixtures thereof. Sleeve 170 may include additional fibers such as elastic fibers to provide elastic properties to sleeve 170 and a ductile fiber discussed with reference to FIG. 54; exemplary elastic fibers include elastane and elastic urethane fibers. The sleeve may be preimpregnated ("prepreg") with a resin. The resin is preferably of a thermoset type, but UV curable or light-activated resins may also be used. The resin system can be any suitable resin, e.g., one that suitably adheres to the fabric of sleeve 170 when cured, including, for example, an epoxy that includes the proper curing agent. Generally, the prepreg sleeve is partially cured to reduce tackiness before its application over conformable core 100. For purposes of the invention, uncured resin is resin that has not been cured or has been partially cured, but the impregnated fabric remains plastically conformable by hand. In contrast, cured resin for purposes of the invention means that the resin has been partially or fully cured such that the resin impregnated fabric is not plastically deformable. Alternatively, sleeve 170 may be applied over conformable core 100 and then impregnated with the resin. Preferably, sleeve 170 does not shrink or does not substantially shrink when cured over conformable core 100, particularly thermal curing. Because of the braiding, the circumference of sleeve 170 can be varied by changing the braid angle. Specifically, the circumference can be increased by pushing lengthwise on sleeve 170 and decreased by pulling lengthwise on sleeve 170. The variable circumference of sleeve 170 allows the width and profile of conformable core 100 to vary.

The principal purpose of the compressor is to increase the strength of the finished composite by forcing out excessive resin from between the fibers, consolidating the fibers and maintaining the fibers in close proximity to bond them together with cured resin.

Referring to FIGS. 1 and 2, connections 129 are designed to guide a sleeve 170, which is pulled over conformable core 100 around the core. Connections 129 have an outside perimeter 173 and an inside perimeter 174. Connections 129 could have an inside perimeter 176 (shown in phantom) that is parallel or similar in shape to outside perimeter 173. Instead it is preferred that they have inside perimeter 174 having an inwardly protruding protuberance 175. If inside perimeter 174 was parallel or similar in shape to the outside perimeter 173, braided sleeve 170 would tend to bunch up on inside perimeter 174 particularly on sharper curves. Protuberances 175a-c have a shape designed to prevent bunching of the braided sleeve 170 resulting in braided sleeve 170 being smooth around the inside perimeter, including around the inside corners at protuberances 175a-c. Protuberances 175a-c are particularly useful when the angle between adjacent lateral members is greater than about 60°, about 90°, or about 110°. The protuberances can be convex like protuberances 175a and 175b, straight like protuberance 175c, or less concave (not shown) than theoretical perimeter 176. Protuberance 175 makes the width of connections 129 wider in the corners and can make the curve of inside perimeter 174 less sharp than outside perimeter 173.

Precursor 102 also has optional first and second release layers 172a and 172b on opposite sides of precursor 102 over sleeve 170. Any suitable release layer may be used including epoxy release film, silicone coated paper, siliconized fiber/cardboard carrier or other release material. No release layer is typically present between conformable core 100 and sleeve 170 because conformable core 100 is not removed from sleeve 170 after sleeve 170 is cured. The release layer can be smooth or textured. If textured, the texture may have an aesthetic.

Ridges 136 and 158 and valley 154 increase the thickness of conformable core 100 thereby increasing the thickness, stiffness and strength of the finished device. The shape of ridges 136 and 158 and valley 154 are arranged to influence the compression of sleeve 170, to decrease gaps and enhance the quality of the cured material.

In FIG. 3, a fitted or conformed precursor 102 attached to a foot brace 177 has been fitted to or bent to conform to the shape over which it was placed, here leg L. The fitted or formed conformable core outlined in phantom is denoted by reference numeral 100'. Foot brace 177 has a foot bed 178, which may be full length as illustrated or partial length, and a connector 180, here an upright or riser. Foot bed 178 may include a heel cup, an arch support and other suitable structures that are found in foot orthoses. Foot brace 177 may be any suitable foot brace and may include one or more straps to hold a person's foot. Riser 180 is inserted into bar acceptor 122 and may be secured using any suitable method or structure including an epoxy adhesive or mechanical fasteners. Foot brace 177 may also have a bar acceptor 122 (partly shown in phantom in FIG. 3) allowing different connectors 180 to be used such as connectors of different lengths or geometries or hinged. It is even contemplated that connector 180 could be changed over the course of treatment of a patient. Suitable padding, such as closed-cell, foam neoprene based padding, may be placed over the leg L and frame 100' fitted to the padding-covered leg to accommodate the use of padding in the finished orthosis.

Figure 51:
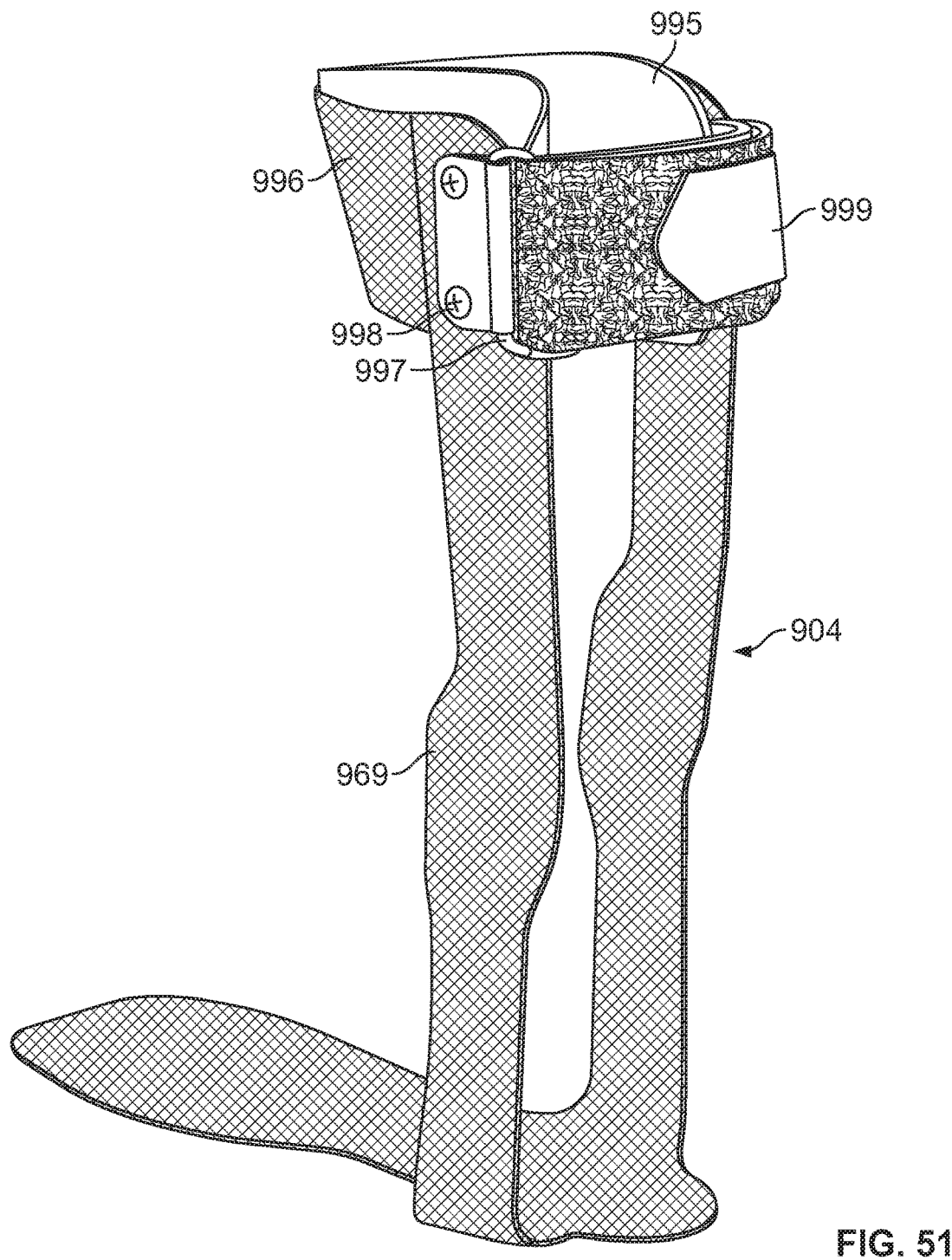
FIG. 51 is a perspective view of a custom ankle-foot orthosis based on the composite precursor of FIG. 50.

Fitting precursor 102 also involves appropriately plastically deforming zig-zag 114 to fit the connection of foot brace 177. The precursor can then be cured in an oven, typically without being attached to foot brace 177, in accordance with the specifications of the prepreg sleeve manufacturer. Generally, curing involves heating precursor 102 while remaining contained and sealed in vacuum bag 168 to a suitable elevated temperature or temperatures, such as, for example, temperatures in excess of about 212° F. or 100° C. The rate of heating and cooling during the curing process of a thermally-cured composite resin can impact the quality of the final composite. Consequently, fitted precursor 102 may be placed in an insulating bag and the insulating bag is subsequently placed in an oven that is held at constant temperature. The rate of heating of the composite within the insulating bag will be decreased by the insulating quality of the bag, improving the quality of the cured composite. After the curing is completed, vacuum bag 168 and release layers 172a, 172b are removed. Foot brace 177 is reattached resulting in a knee-ankle-foot orthosis 104 illustrated in FIG. 4. Foot brace 177 could include an ankle hinge (not shown). Padding may be attached to various inside surfaces 182 of the orthosis. The use of padding is more fully discussed relative to FIG. 51. Straps may be attached to outside surfaces 184 of orthosis 104 in any suitable manner. In particular, straps may be removably attached to and around surfaces 184a and 184b corresponding to lateral portions 106a and 106c, such as with hook fasteners that are adhered to surfaces 184a and 184b and which removably hook onto the fabric of the strap. A strap may include its own hook and loop fasteners and may be folded over a portion 106 such that the hook and loop fasteners engage. Other steps and attachments that are well known in the orthosis art may be employed to finish orthosis 104. Orthosis 104 includes fitted frame 100', a cured sleeve 170' (corresponding to prepreg sleeve 170), foot brace 177, and one or more bar acceptors 122 with corresponding connector 180 for connecting the fitted precursor to foot brace 177.

Double-Upright Ankle-Foot Orthosis

In another embodiment of the invention, two conformable core or support structures 200a and 200b, a fitted frame 200', a composite precursor 202, and an ankle-foot orthosis 204 with a double upright are provided as illustrated in FIGS. 5-9. The second embodiment is very similar to the first embodiment such that the discussion of the second embodiment is generally limited to the differences between the first and second embodiments. Where parts are the same or similar between the first and second embodiments, the same reference numerals may be used or the reference numerals may differ by 100.

Figure 5:
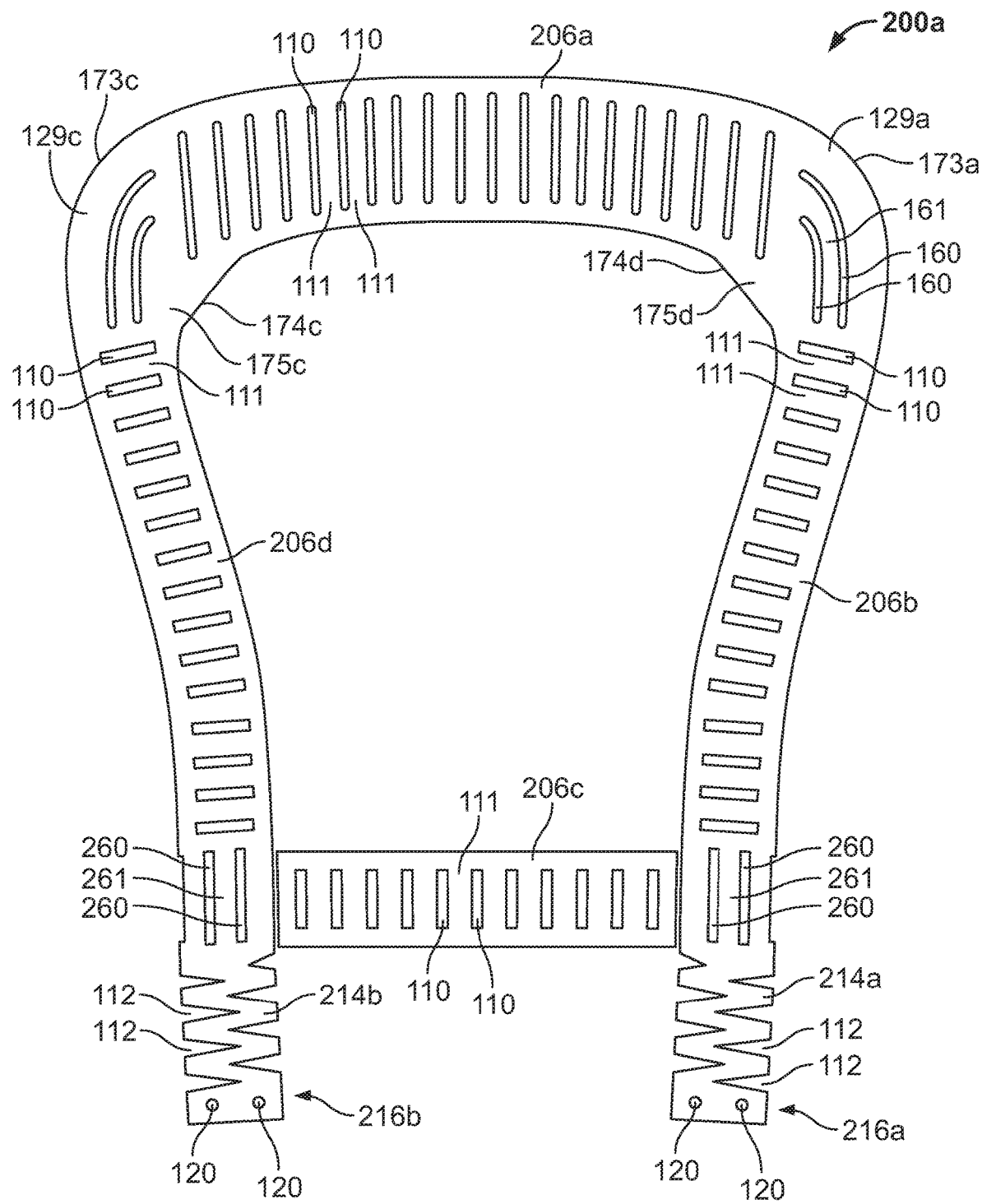
FIG. 5 is a front elevation view of one embodiment of a conformable support structure or core that can be used to make a double-upright ankle-foot orthosis.
Figure 6:
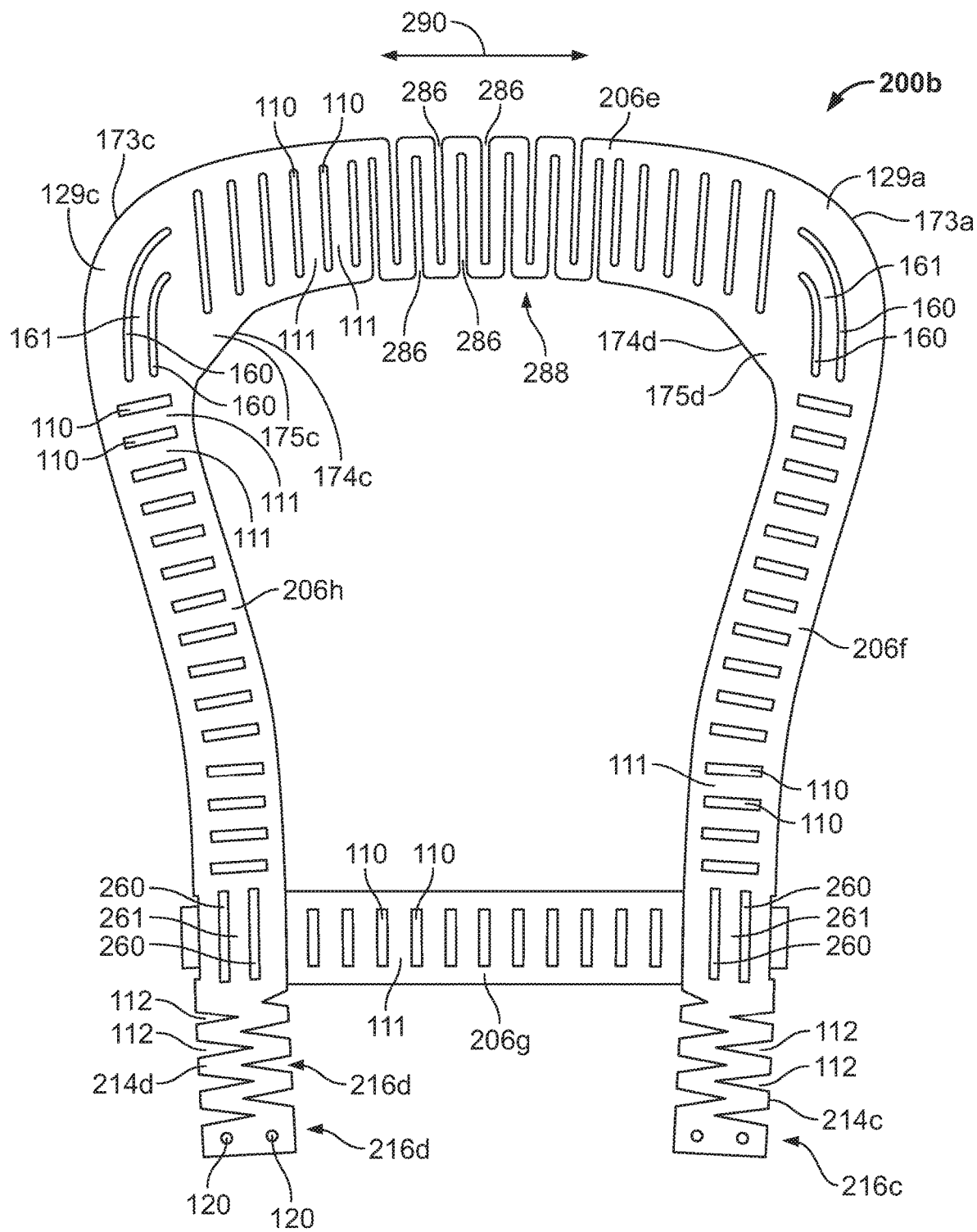
FIG. 6 is a front elevation view of another embodiment of a conformable core that can be used in a double-upright ankle-foot orthosis.

Conformable support members or cores 200a and 200b are illustrated in FIGS. 5 and 6, respectively. Conformable cores 200a and 200b have four lateral members 206a-d and 206e-h laid out in a substantially trapezoidal arrangement. Lateral members 206a, 206b and 206d, and 206e, 206f, and 206h are preferably unitary. Lateral members 206b, 206d, 206f, and 206h have a free extremity 216a, 216b, 216c and 216d, respectively, at which there is a zig-zag 214a, 214b, 214c and 214d. Extremities 216a-216d are similar to extremity 116 in that they are used to attach to another orthotic attachment, typically via bar acceptors 122. Typically, lateral members 206c and 206g are not connected to conformable cores 200a and 200b. The main difference between lateral members 206c and 206g is length. Conformable cores 200a and 200b also have two pairs of voids or slots 260 and a land 261 between pairs of slots 260. Like land 161, lands 261 may be raised or lowered to stiffen the core. Conformable core 200b has a type of void not previously discussed, which can be part of conformable core 100 or 200a. Conformable core 200b has alternating, parallel rectangular voids 286 resulting in member 206e having a serpentine or expandable section 288 which permits member 206e to be lengthened as indicated by double arrow 290 or shortened. Cores 200a and 200b have connectors 129a and 129c having inside perimeters 174c and 174d and inwardly protruding protuberances 175c and 175d.

Figure 7:
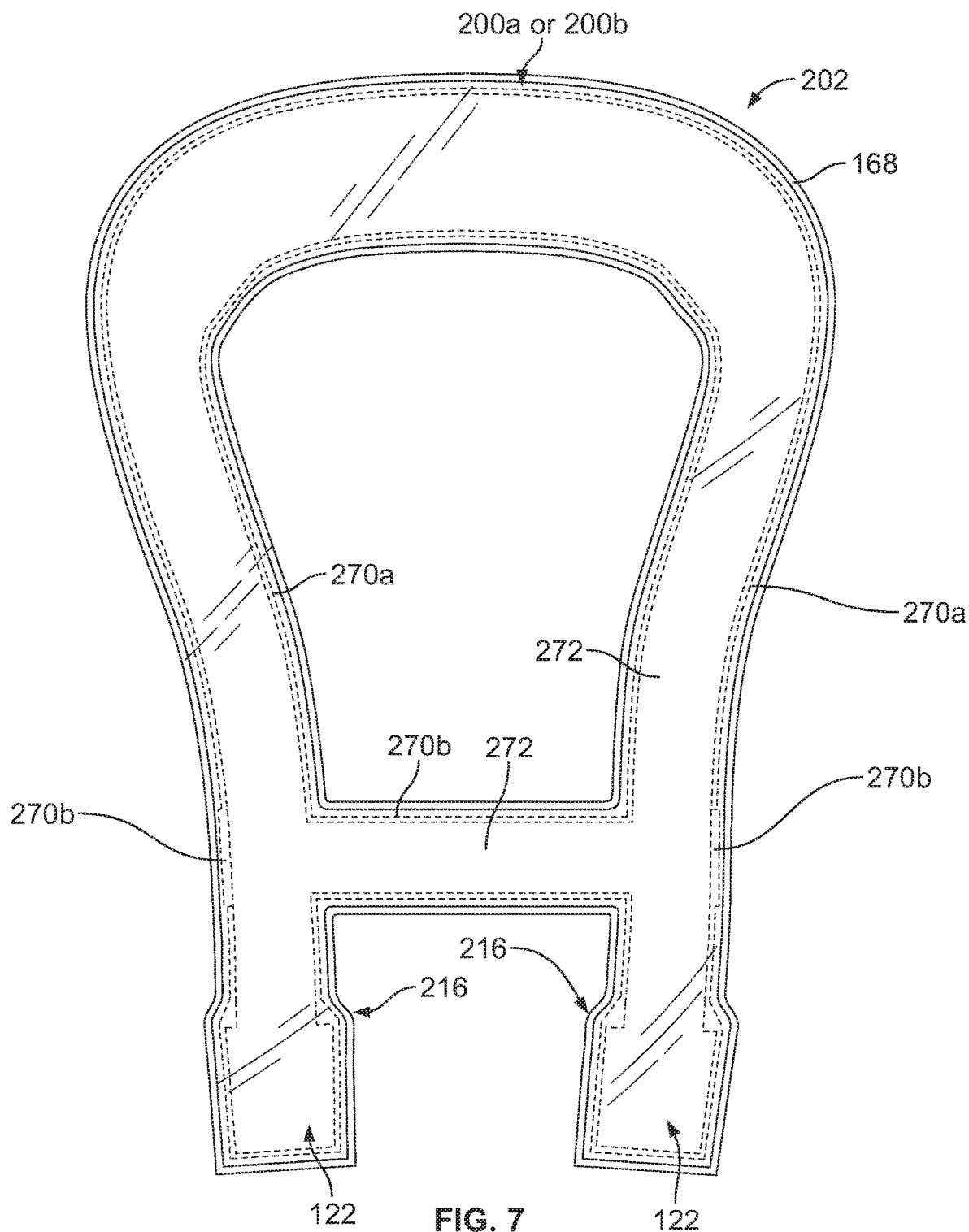
FIG. 7 is a front elevation view of a curable conformable composite precursor having the frame of either FIG. 5 or FIG. 6 incorporated therein.

FIG. 7 illustrates precursor 202, which may include conformable core 200a or 200b, the outline of which is shown in phantom. Precursor 202 includes two braided sleeves 270, the combination of which is shown in outline in phantom, and release layer 272. One braided sleeve 270a covers members 206a, 206b and 206d, or 206e, 206f and 206h. The second sleeve 270b covers member 206c or 206g. Sleeve 270b is longer than member 206c and may be longer than member 206g. Sleeve 270b is long enough to overlap with members 206b and 206d, or 206f and 206h, or may be long enough to be folded over members 206b and 206d, or 206f and 206h, as illustrated in FIG. 7. Precursor 202 is illustrated as having bar acceptors 122 under braided sleeve 270.

Figures 7A, 7B:
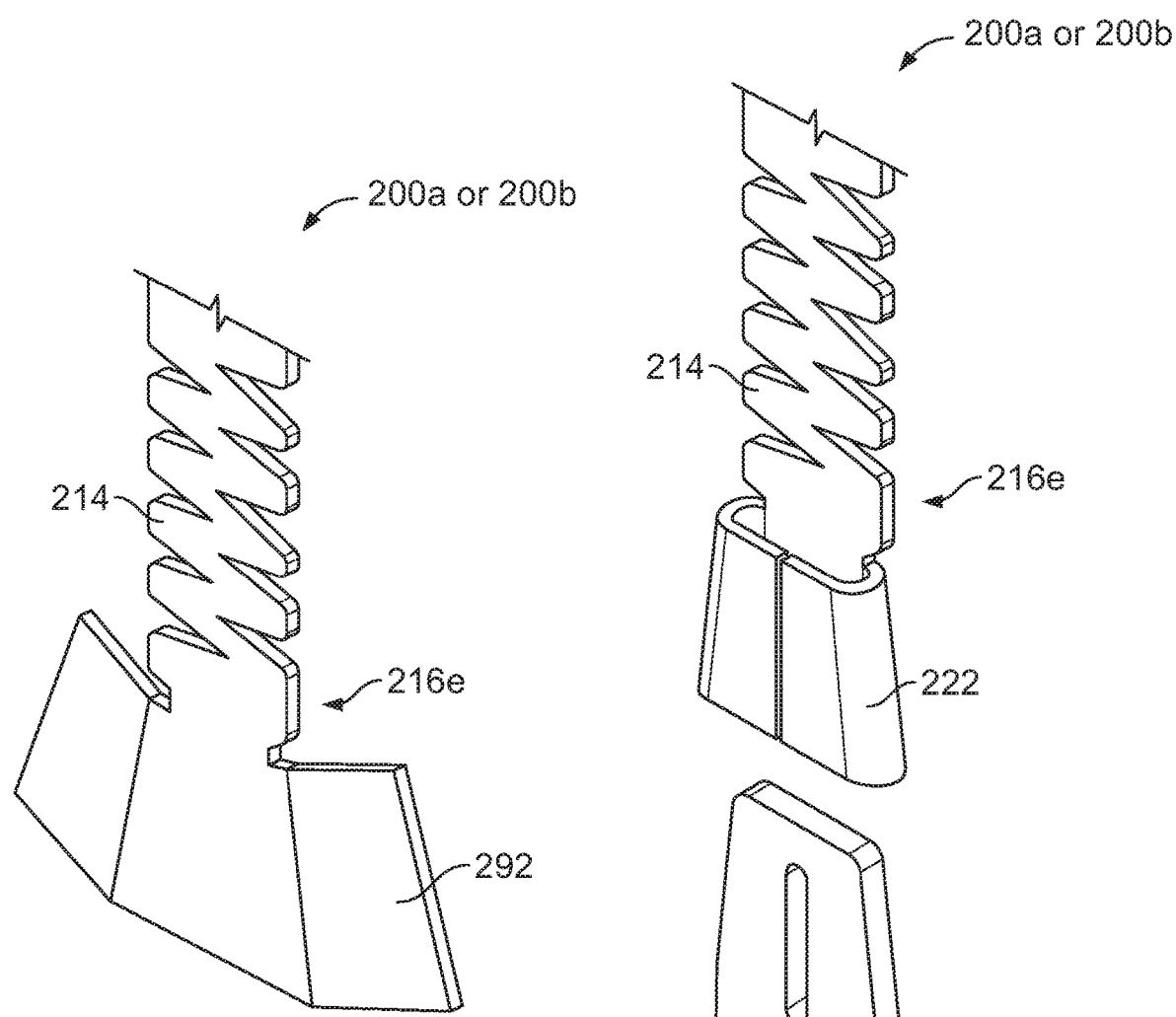
FIG. 7A is a perspective view of an alternative free extremity for the conformable cores of FIGS. 5 and 6.
FIG. 7B is a perspective view of the free extremity of FIG. 7A formed into an integral acceptor with an adaptor.

FIGS. 7A and 7B illustrate a variation of free extremities 216 for cores 200 indicated by reference numeral 216e. In FIG. 7A, free extremity 216e is shown as having opposed wings 292, but can have a larger, single wing. In FIG. 7B, free extremity 216e is shown with opposed wings folded over to form an integral bar acceptor 222 having an internal cavity. Bar acceptor 222 can be rectangular like bar acceptor 122 or trapezoidal as shown and the internal cavity can be rectangular or trapezoidal. Bar acceptor 222 may be used with a male or female connector 394 during customization or fitting of precursor 202 as discussed in greater detail with respect to a knee-ankle-foot-orthosis (KAFO). Connector 394 may be replaced in the finished orthosis with any suitable connector or adaptor for connecting to a foot brace 277. One such suitable adaptor is adaptor 293 (shown in FIG. 7B) for use with a triple action orthotic ankle joint as disclosed in U.S. application Ser. No. 14/738,212 (adaptor 293 serves as upper bar 16 in the referenced application), which is incorporated herein by reference.

Figure 8:
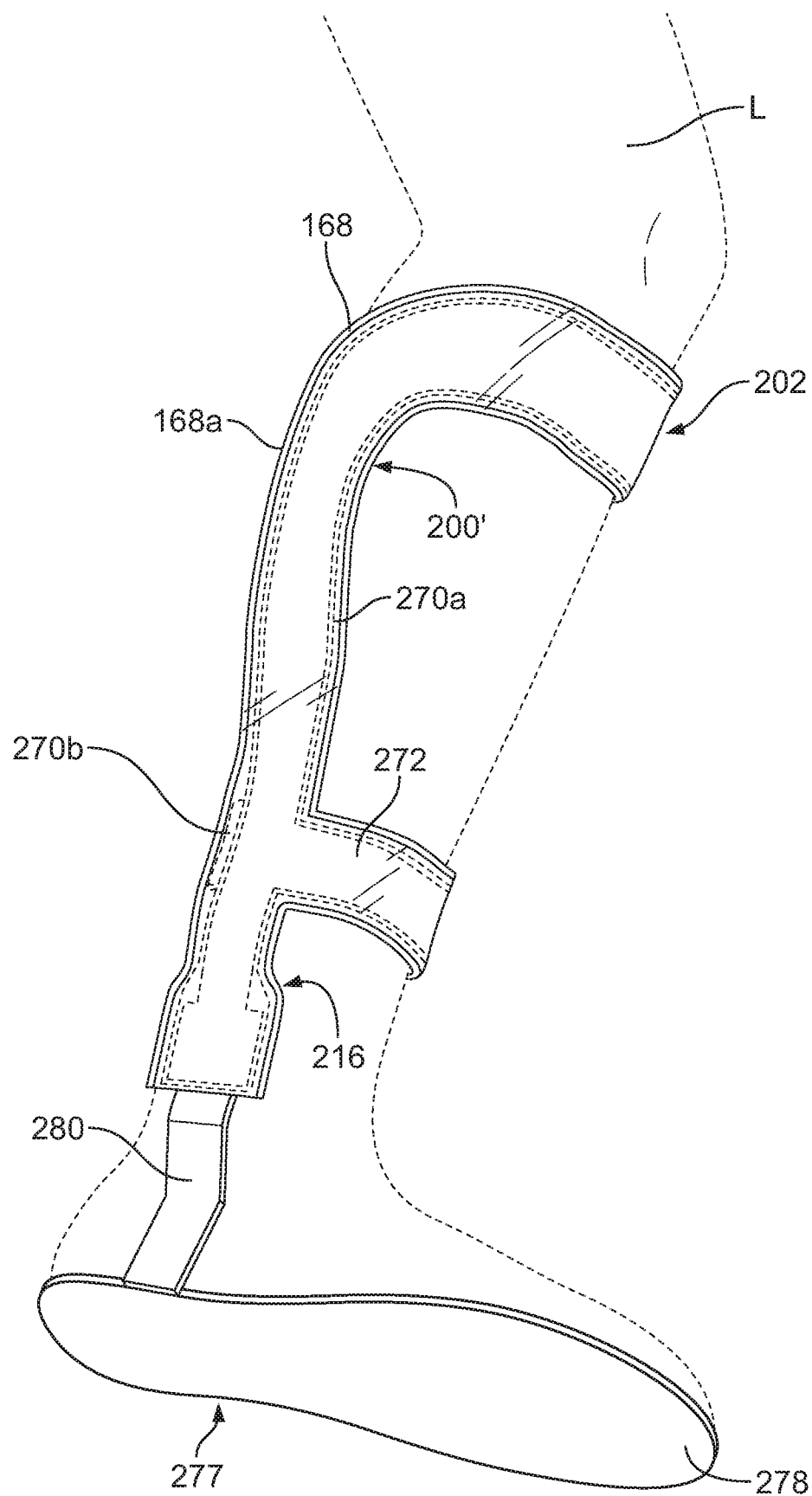
FIG. 8 is a perspective view of the curable conformable composite precursor of FIG. 7 having been conformed to fit around a leg of a patient.

FIG. 8 illustrates precursor 202 customized, fitted, contoured or shaped to match leg L and to attach to foot brace 277 having footbed 278 by uprights 280. The custom fitted frame is denoted by numeral 200'. If precursor 202 includes conformable core 200b, then member 206e can be lengthened or shortened to better match leg L.

Figure 9:
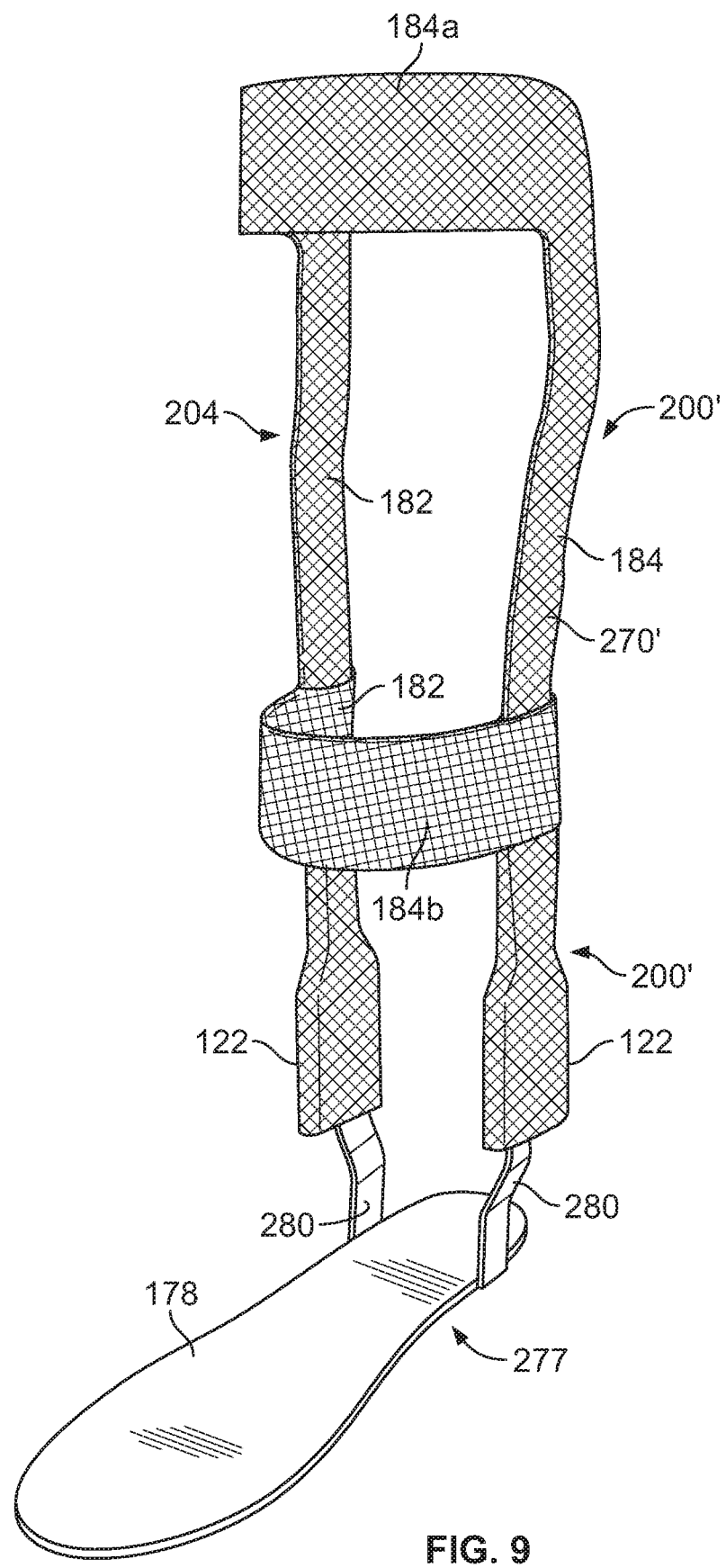
FIG. 9 is a perspective view of a cured, custom double-upright ankle-foot orthosis based on the precursor of FIG. 8.
Figure 14:
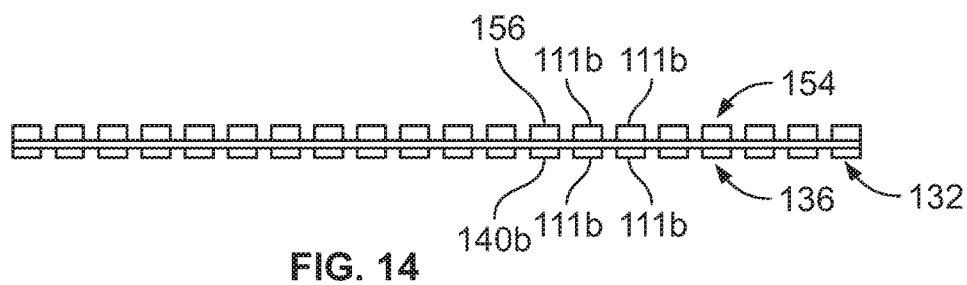
FIGS. 14-17 illustrate another embodiment of a conformable core member having another specially configured cross-sectional shape.
Figure 15:
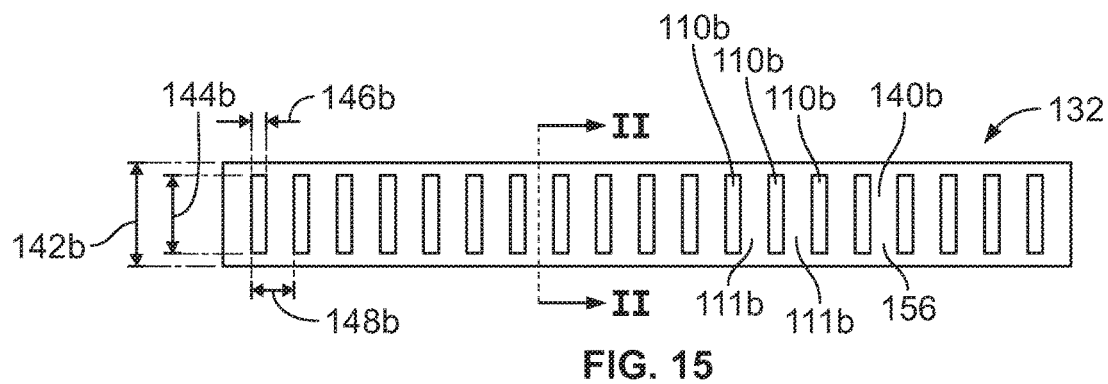
Figure 16:
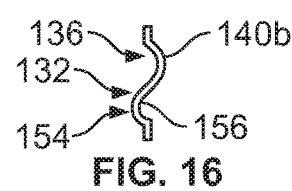
Figure 17:
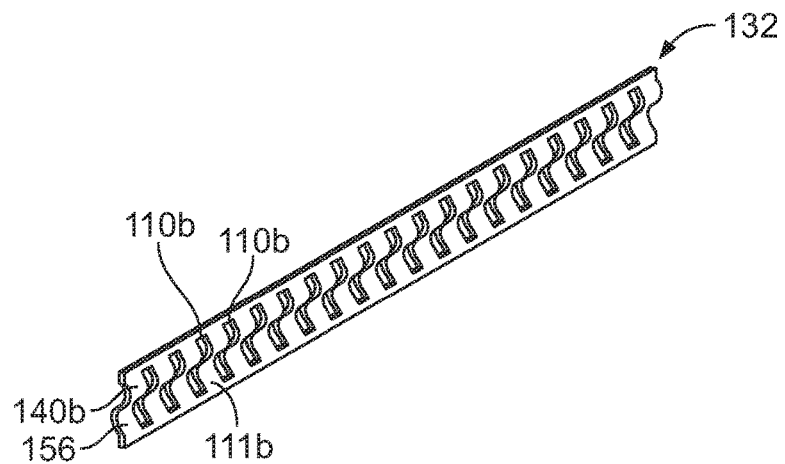
Figure 18:
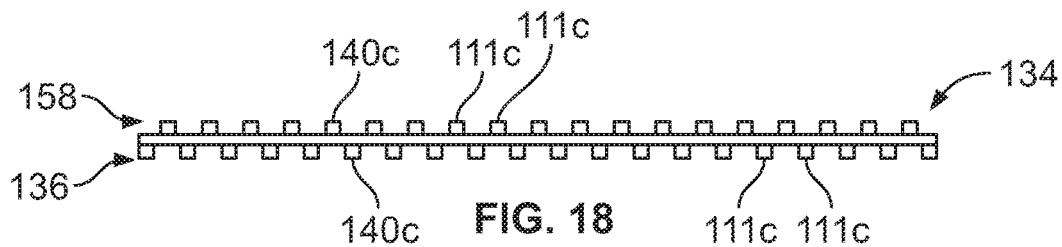
FIGS. 18-21 illustrate another embodiment of a conformable core member having another specially configured cross-sectional shape.
Figure 19:
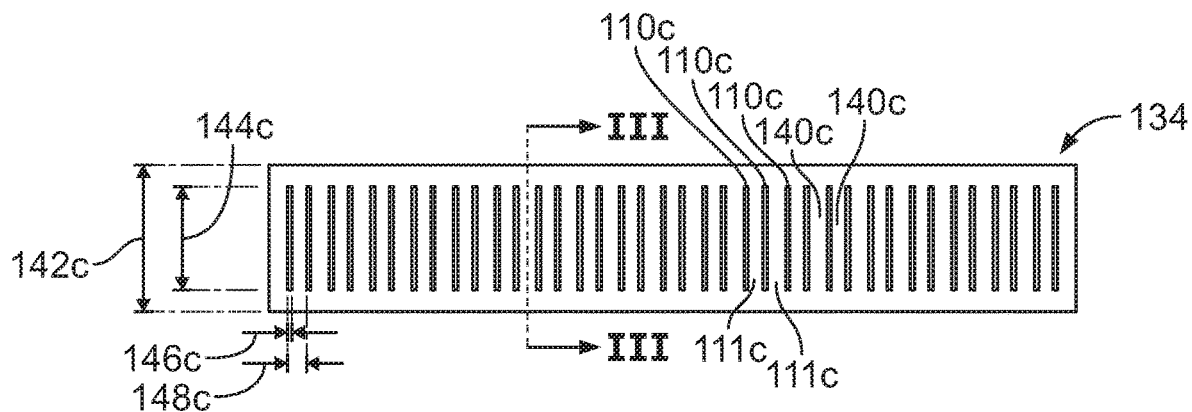
Figure 20:
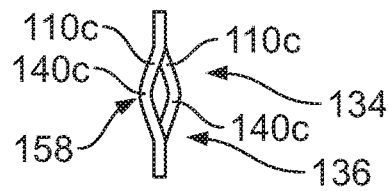
Figure 21:
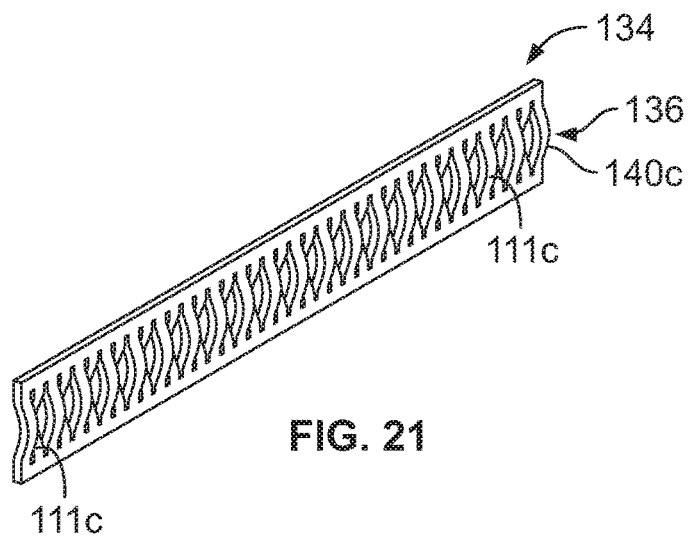

FIG. 9 illustrates ankle foot orthosis 204 having a cured fiber sleeve 270' and a foot brace 277 with two uprights 280. Uprights 280 are inserted into bar acceptors 122 attached to frame 200' at ends 216a-d.

Knee-Ankle-Foot Orthosis

In still another embodiment of the invention, a conformable core or support structure 300, two composite precursor portions 302a, 302b, and a knee-ankle-foot orthosis 304 are provided as illustrated in FIGS. 22A-22F. The third embodiment is very similar to the first and second embodiments such that the discussion of the third embodiment is generally limited to its differences from the first and second embodiments. Where parts are the same or similar to parts of the first and second embodiments, the same reference numerals may be used or the reference numerals may differ by 100 or 200.

Figure 22B:
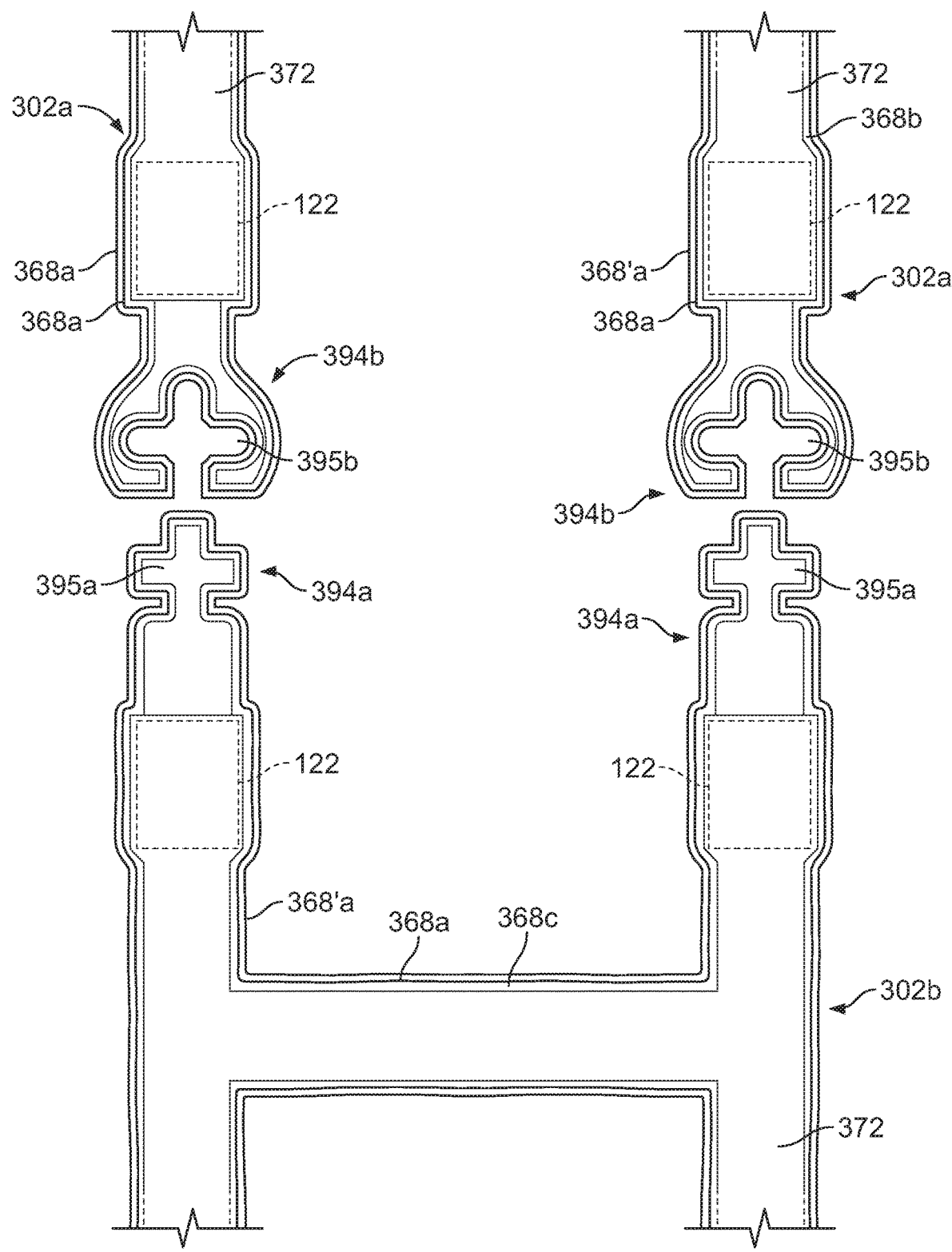
FIG. 22B is an elevation view illustrating the attachment of two precursor portions for the knee-ankle-foot orthosis of FIG. 22F.
Figure 22F:
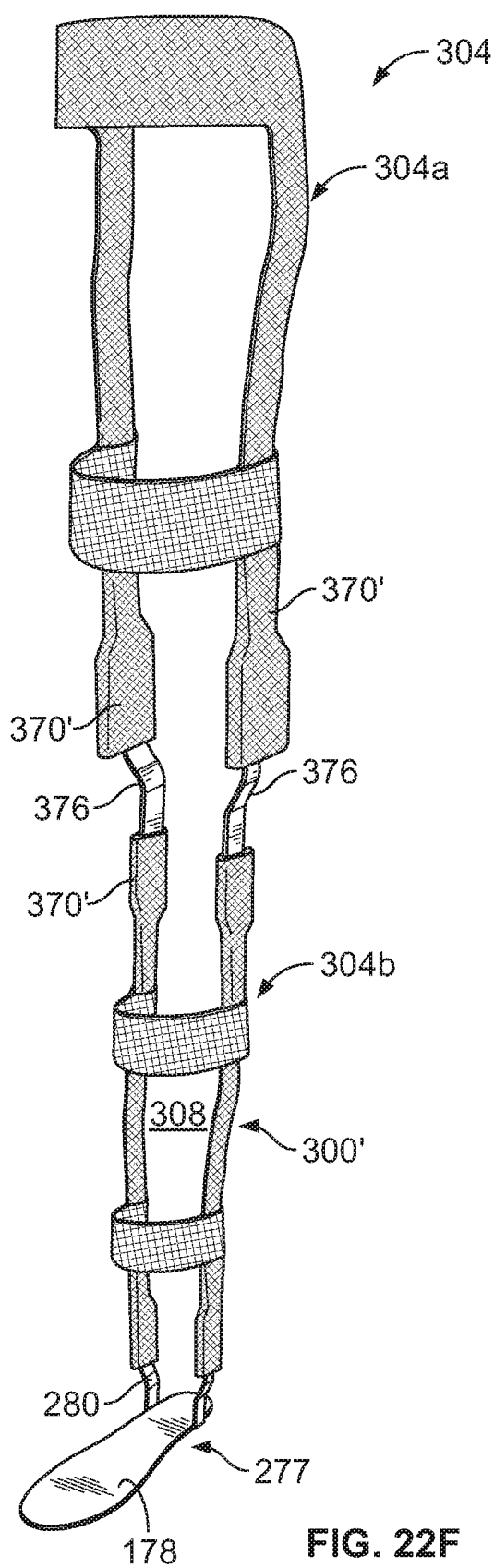
FIG. 22F is a perspective view of a knee-ankle-foot orthosis incorporating the conformable core of FIG. 22A.

FIG. 22F illustrates a knee-ankle-foot orthosis (KAFO) 304 having a top half 304a and a bottom half 304b both including cured fiber sleeves 370'. The top half 304a is based on a conformable support member that can be or is very similar to conformable cores 200a or 200b, except that it has a size appropriate for the thigh portion of a KAFO. The bottom half 304b has a fitted frame 300', which is illustrated as unfitted conformable core 300 in FIG. 22A.

Conformable core 300 generally has four separate lateral members 306a-306d enclosing a void 308. Top and bottom members 306a and 306c are very similar differing primarily by length. Members 306a and 306c as illustrated are similar to member 206c, but they can be longer like member 206g so as to overlap with members 306b and 306d. Side members 306b and 306d are similar and may even be identical prior to any customization. Members 306b and 306d are similar to portion 106d except that they each have two free extremities 316 rather than one free extremity 116 and one connection 129c. Each extremity 316 has a zig-zag 314 and attachment apertures 320 for attaching a bar acceptor 122 to extremity 316.

FIG. 22B illustrates another embodiment of attaching a precursor to another orthotic portion during the fitting, shaping, contouring and/or customizing of the precursor. This manner of attachment may be used in conjunction with precursors 102, 202, 302a and 302b and other conformable precursors. In particular, FIG. 22B illustrates the attachment of precursor portions 302a and 302b, corresponding to portions 304a and 304b of FIG. 22F, to each other. Precursor portion 302a has vacuum bag 368a or other suitable compressor around it while precursor portion 302b has vacuum bag 368b around precursor 302b, both illustrated with seals 368'a. Precursors 302a and 302b have bar acceptors 122 (shown in phantom), braided sleeves (not shown), and release layer 372. Attached to precursors 302a and 302b via bar acceptors 122 are male and female connectors 394a and 394b. Male and female connectors 394a and 394b are contained within the vacuum bag 368 for their precursor portion 302a and 302b. Vacuum bags 368a and 368b fit tightly over connectors 394 such that male and female connectors 394 can securely attach to each other. Alternatively, connectors 394 may be located outside their vacuum bag 368 if vacuum bag 368 extends into bar acceptor 122 as discussed with respect to bag 168. It is generally preferred to have connectors 394 inside vacuum bag 368 so that the acceptor does not collapse due to the vacuum in vacuum bag 368.

With reference to FIGS. 22B-22E, male and female connectors 394 will now be described. For clarity of illustration, FIGS. 22C-22E show connectors 394 as not being contained in a vacuum bag 368. Male connector 394a has a male mating portion 395a while female connector 394b has a female mating portion 395b. Similarly, male connector 394c has a male mating portion 395c and female connector 394d has a female mating portion 395d. Male mating portion 395a is in the form of a cross, but any other suitable shape may be used. Female mating portion 395b is a void in the shape of a cross. Mating portions 395 are sized relative to each other so that they can securely mate. If mating portions 395 are intended to be used within compressors or bags 368 then the sizing of the female portion is designed to accommodate the thickness of one or two compressors or vacuum bags 368 and seals 368a as necessary. Female mating portions 395b and 395d are shown as traversing the entire thickness of connectors 394b and 394d, but need not do so. Mating portions 395 have chamfered or rounded edges to facilitate their mating. Connectors 394 may have a suitable structure for holding the connector within the cavities of bar acceptor 122 or 222 such as rectangular spade 396a or trapezoidal or tapering spade 396b, respectively. Spade 396 may be covered by a release agent or film to assist with decoupling connector 394 from the orthosis. Any suitable release agent or film may be used including silicone lubricants and wax, either of which may be sprayed, brushed or dipped on. Additionally or alternatively, the cavities of acceptors 122 or 222 may have a release film or coating. Preferably, bags 368 are sufficiently stretchable under vacuum that they conform to the shape of connectors 394 without having to create bags having geometries matching connectors 394.

Generally, the purpose of the male and female connectors 394 is to connect a precursor to another orthotic portion during the fitting of the precursor. Male and female connectors 394 may be clamped to each other during fitting. Generally, connector 394 is not removed until the precursor has been cured. Connector 394 may be removed before curing if it is not contained within a compressor or vacuum bag 368. The male and female connectors 394 may be disconnected from each other at any suitable time after the fitting, such as before or after curing. Connector 394 may be made of any suitable materials including the same materials as conformable core 100. Connectors 394 may be stamped or laser cut from sheet metal. Other materials may be used including materials that have some flexibility such that the female mating portion 395b flexes open when portions 395a and 395b are matingly engaged and disengaged. Generally, the materials are selected so that the connectors 394 do not deform during curing. Connectors 394 are typically disposable in that they usually do not become part of the finished orthosis, but they could be part of the finished orthosis in some embodiments.

With reference to FIG. 22F, knee-ankle-foot orthosis 304 includes a foot brace 277 and knee brace portions 376, which connect to halves 304a and 304b by bar acceptors 122. Knee brace portions 376 may be rigid along their length as illustrated to prevent bending at the knee or may be articulating to allow bending at the knee. Knee brace portions 376 replace male and female connectors 394 in knee-ankle-foot orthosis 304. Knee brace portions 376 may attach to bar acceptors 122 by adhesives or by mechanical fasteners.

Lumbosacral Orthosis

Figure 23:
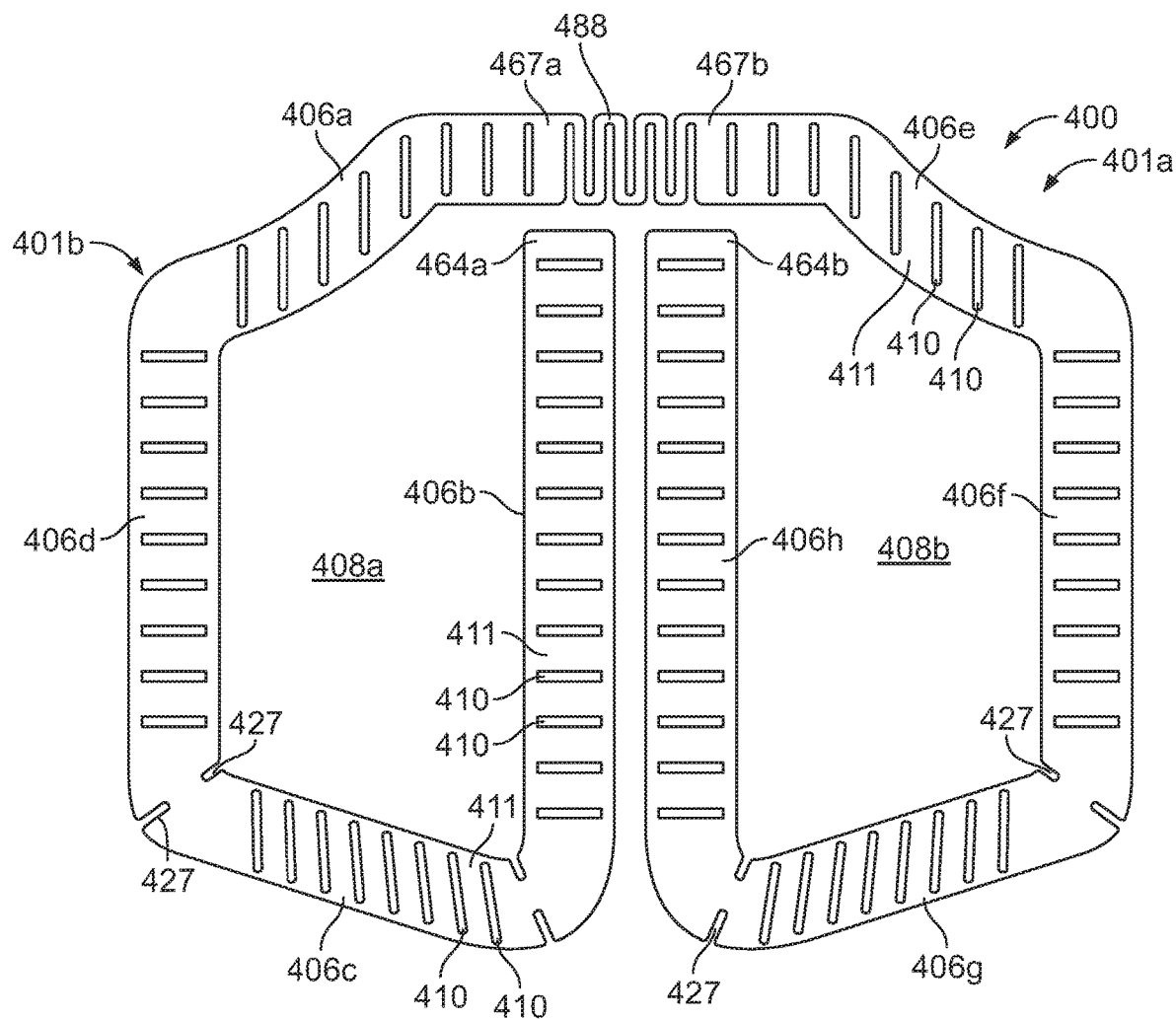
FIG. 23 is a front elevation view of a conformable support structure or core for a lumbar sacral orthosis.
Figure 24:
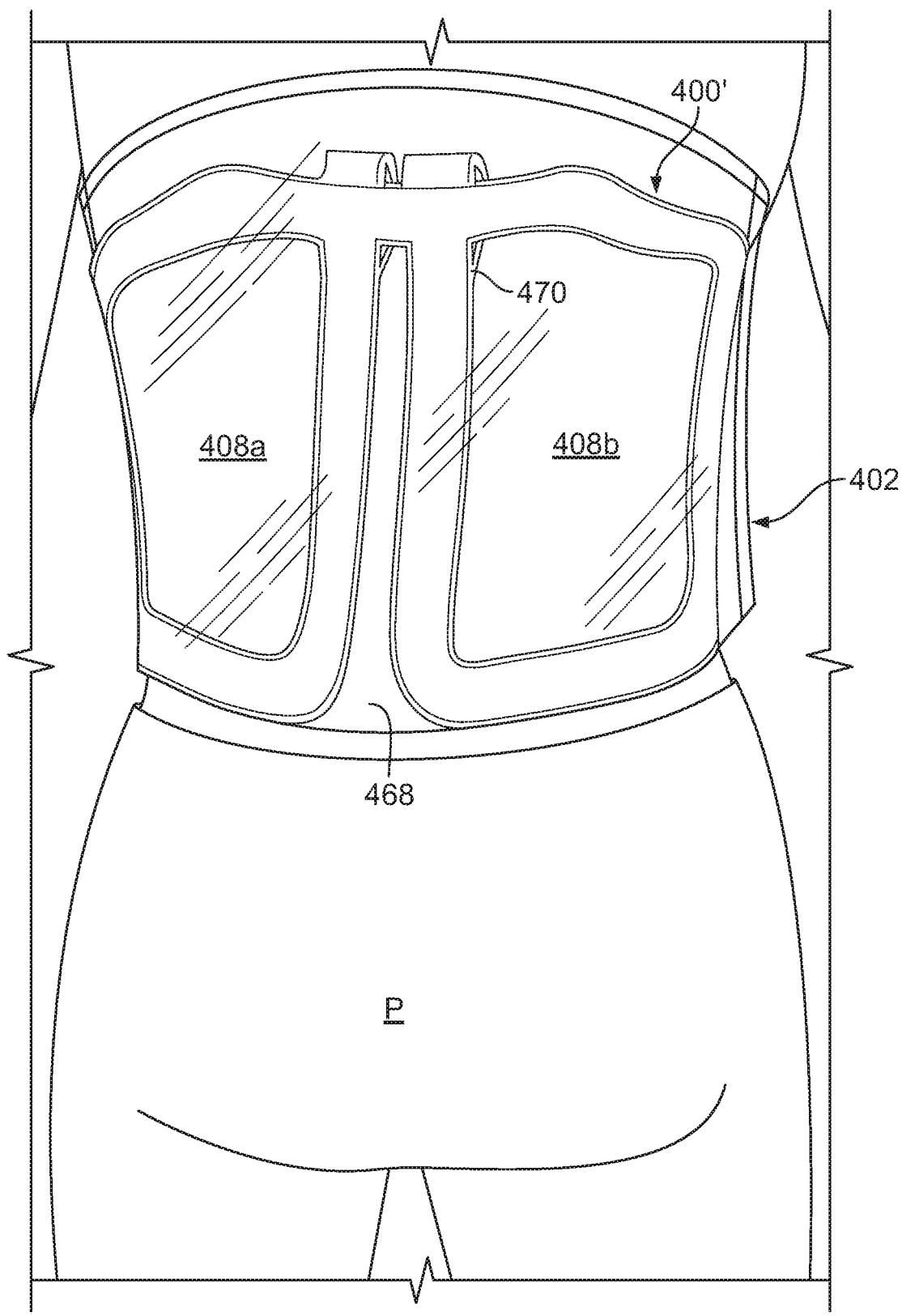
FIG. 24 is a perspective view of the lumbar sacral orthosis customized to fit a person's back having the conformable core of FIG. 23 incorporated therein.

In yet another embodiment of the invention, a conformable support member or frame 400, a composite precursor 402, and a lumbosacral orthosis are provided as illustrated in FIGS. 23 and 24. This fourth embodiment is similar to the prior three embodiments and the discussion of this embodiment is generally limited to differences from those embodiments. Where parts are the same or similar between the fourth and first three embodiments, the same reference numerals may be used or the reference numerals may differ by multiples of 100. Frame 400 partially encloses two voids 408a and 408b. Frame 400 has two halves 401a and 401b, one around each void, which are substantially symmetrical. Each half is substantially trapezoidal. Frame 400 has side members 406a-h. Members 406b and 406h are spine-flanking members. Each of the members has elongated slots 410 and lands 411, which are substantially parallel within the same member 406. Frame 400 also has four opposed pairs of open-ended voids or slots 427 and serpentine section 488. Slots 427 permit tilting of members 406c and 406g, which in use are located closest to the pelvis, to conform better to a patient's body shape. Frame 400 has two free ends 464a and 464b for feeding braided sleeve 470 around frame 400. Sleeve 470 may be looped over edges 467a and 467b as shown in FIG. 24. Frame 400 can have more of the same or different structures for making frame 400 more easily deformable such as zig-zags 114. Frame 400 is shown without protuberances 175, but could have them.

In FIG. 24, precursor 402 based on fitted frame or conformable core 400', which is not directly visible in FIG. 24, is illustrated as having been plastically deformed to fit the lower back of a person P. After curing, straps can be suitably attached to finish the orthosis. Precursor 402 has a vacuum bag 468. Vacuum bag 468 as illustrated does not have voids corresponding to voids 408a and 408b of conformable core 400.

Linear Precursor with Frame

Figure 25:
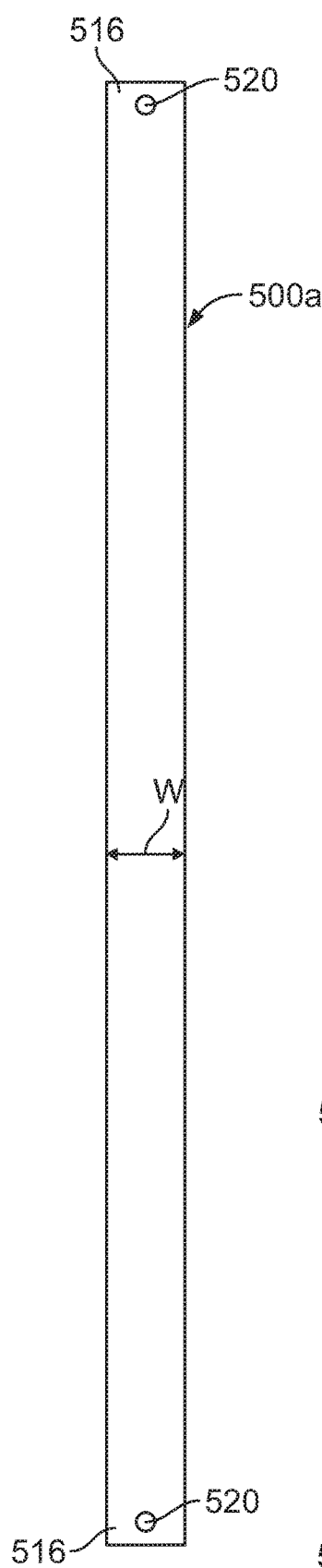
Figure 26:
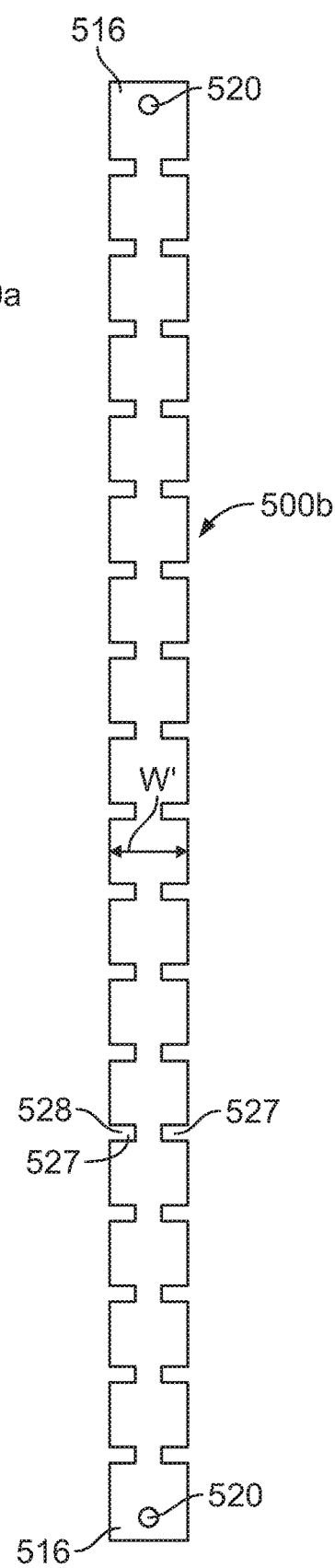

In another embodiment of the invention, two frames or conformable cores 500a, 500b, a composite precursor 502 and finished structures 504a-d, are illustrated in FIGS. 25-35. These embodiments are similar to the prior embodiments and like reference numerals (or multiples of 100) denote like or similar elements FIGS. 25 and 26 illustrate frames 500a and 500b. Conformable support structures, sometimes denominated as cores or frames, 500a and 500b, may be made from flat bar stock or other suitable source. Typically, such cores are thin in one dimension to permit easy bending along that dimension and generally parallel to the width dimension W and W' as shown in FIGS. 25 and 26, for example, to conform the precursor to a desired shape or form. Cores 500a and 500b have attachment apertures 520 at extremities 516. The number of apertures 520 may be varied at each extremity 516 from zero to any suitable number depending on the application. Cores 500a and 500b may be used with bar acceptors 122 or they may be attached to another core or structure by conventional fasteners. Core 500a may be flat and without voids except for attachment apertures 520 as illustrated. Alternatively, it can have parallel slots, valleys and/or ridges like members 131, 132, and 134. Core 500b is illustrated with regularly spaced opposed voids 527 having an open end 528. Core 500*b* may also have parallel slots, valleys and/or ridges, as in members 131, 132, and 134.

Figure 27:
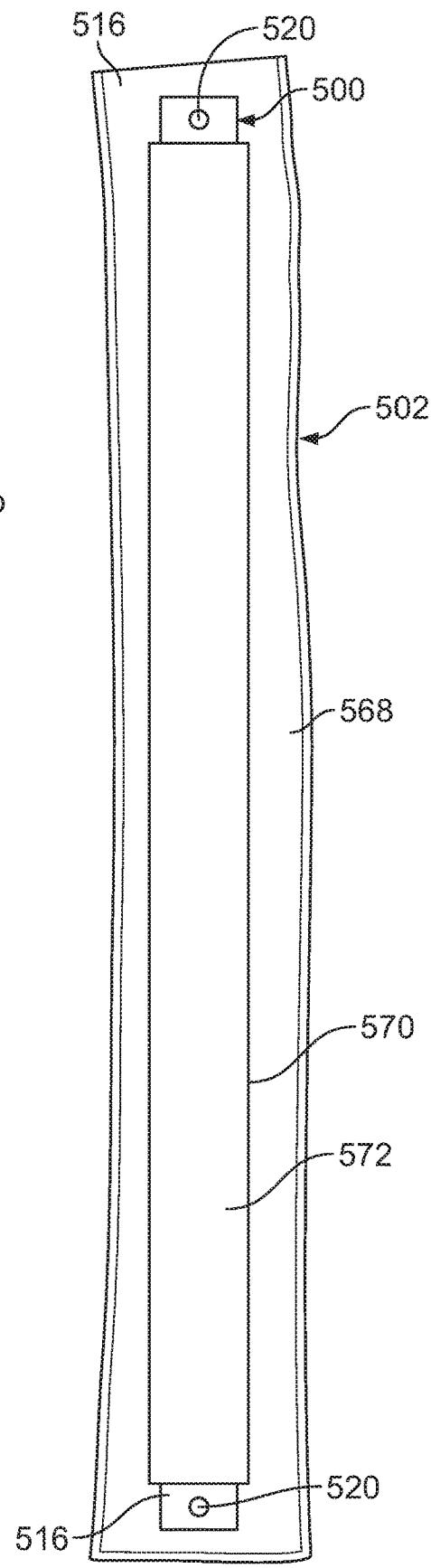
Figure 36:
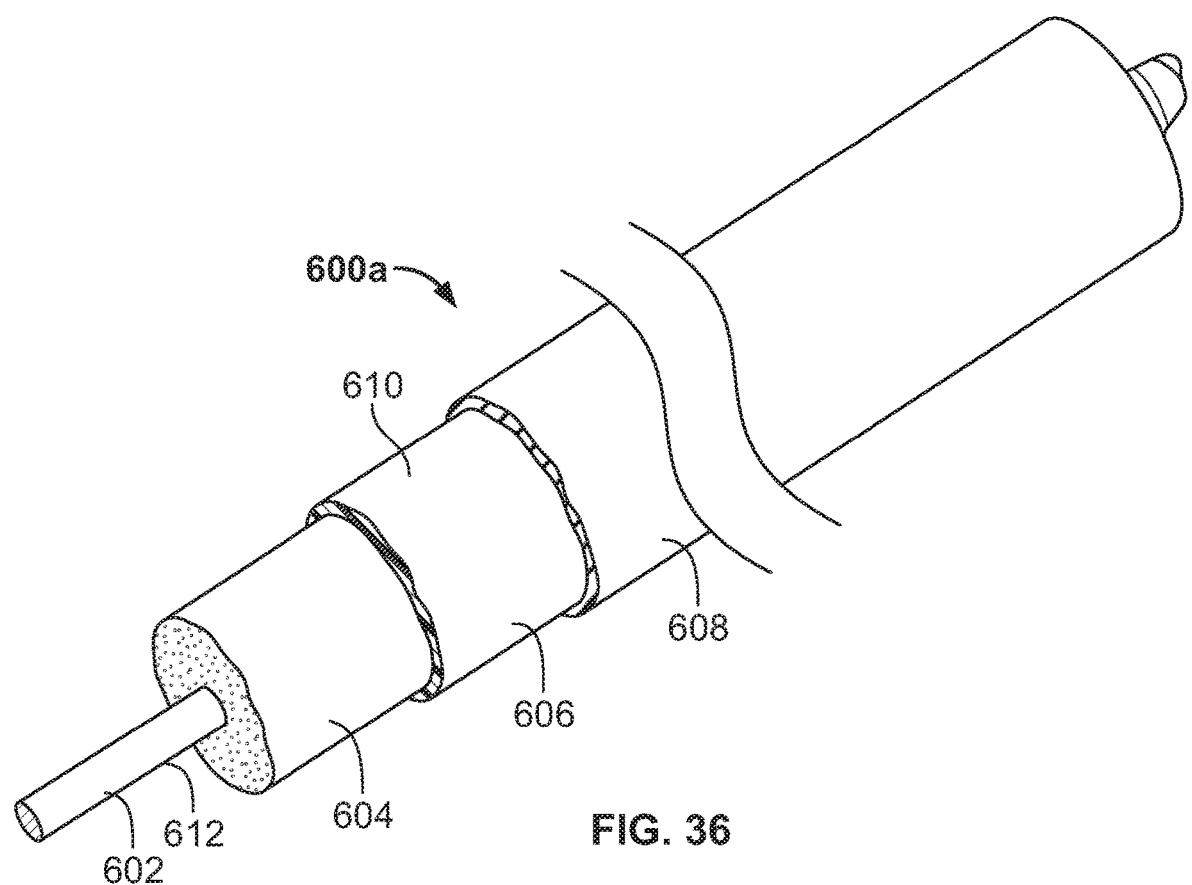
FIG. 36 is a perspective, partial sectional view of a cylindrical curable conformable composite precursor having a conformable solid wire core.

In FIG. 27 is illustrated a linear or bar stock precursor 502 with a case or frame 500, based on either of cores or frames 500*a* or 500*b*. Linear precursor 502 has a fiber prepreg braided sleeve 570 or fiber prepreg cloth around it with a release layer 572 covering the fiber prepreg on both of its principal sides. As illustrated, the fiber prepreg does not cover attachment apertures 520 and extremities 516, but the fiber prepreg may cover apertures 520 or extremities 516 like the other precursors disclosed herein. Similarly, the fiber prepreg of the other precursors may not cover their attachment apertures, if any, or their free extremities. Precursor 502 is illustrated with a vacuum bag 568 around precursor 502, but may have a wrap or compressor instead or in addition. Bag 568 may be tight or loose around precursor 502. Precursors 502 may be joined together with conventional fasteners or with bar acceptor 122 before final curing of the prepreg in which case multiple precursors 502 may be contained in a single vacuum bag 568 or individual precursors 502 may have individual wrappers or compressors.

Precursor 502 may be bent into any suitable shape primarily along the longitudinal axis of core 500*a* or 500*b* and parallel to the width W dimension (as opposed to the height dimension which is thin) of core 500*a* or 500*b*. Voids 527 of core 500*b* also permit some bending normal to the width dimension W. FIGS. 28-31 show precursors 502*a-d* after having been bent by hand pressure into desired exemplary shapes of an S-shape, an L-shape, a V-shape, and an O-shape, respectively. Obviously, precursor 502 could be bent into numerous other shapes by hand as desired. FIGS. 32-35 show finished rigid structures 504*a-d* having cured fiber sleeves 570' based on precursors 502*a-d*, respectively, with the release layers 572 and vacuum bag 568 having been removed.

Linear Precursors with Conformable Core or Support Structure

Figure 37:
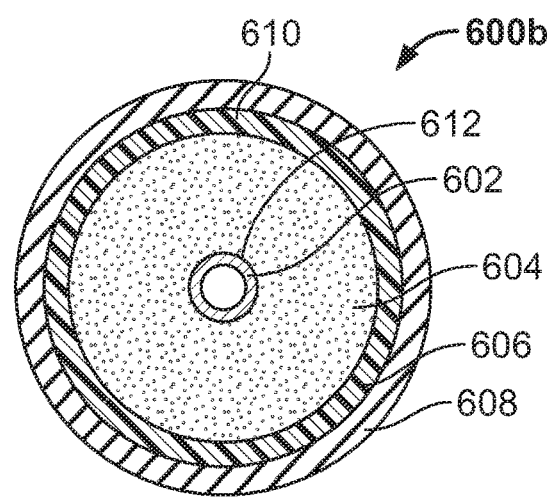
FIG. 37 is a cross-sectional view of a cylindrical curable conformable composite precursor having a hollow wire conformable core.
Figure 38:
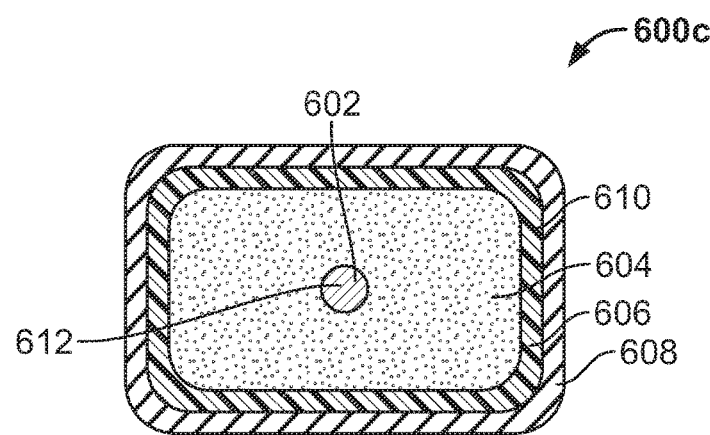
FIG. 38 is a cross-sectional view of a curable conformable composite precursor having a solid wire conformable core, the composite precursor having a generally rectangular cross-sectional shape.

In another embodiment, a linear or bar or cylindrical precursor 600 is provided having variants as illustrated in FIGS. 36-39. In a principal variant, precursors 600*a* and 600*b* are cylindrical, having a desired cross-sectional shape which may be a circular cross section as illustrated in FIG. 37. However, any suitable cross-section is possible including a rectangular shape as in precursor 600*c* or an elliptical or oval shape as in precursor 600*d*. Precursor 600 has a core 602, a fiber layer 606 and an outer compressor or vacuum packaging layer 608.

Figure 39:
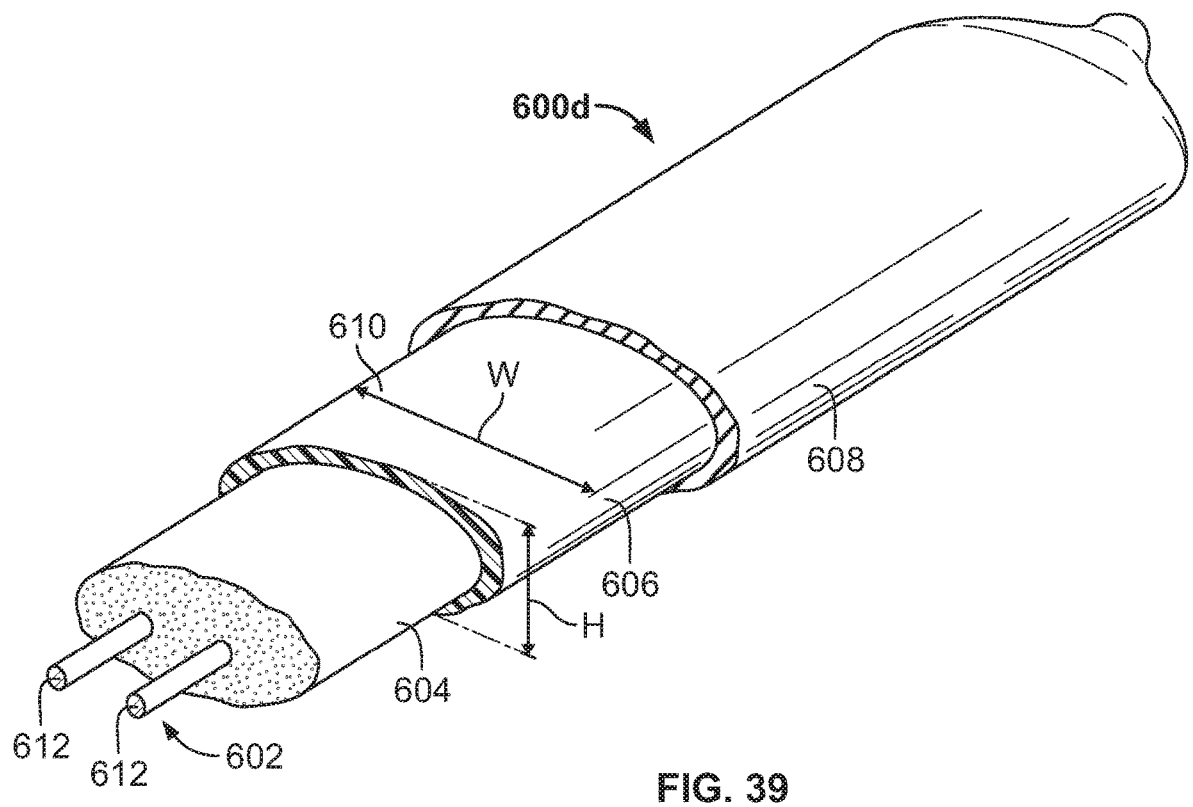
FIG. 39 is a perspective, partial sectional view of an elongated composite precursor having two parallel, conformable solid wires and an overall oval cross-sectional shape.
Figure 40:
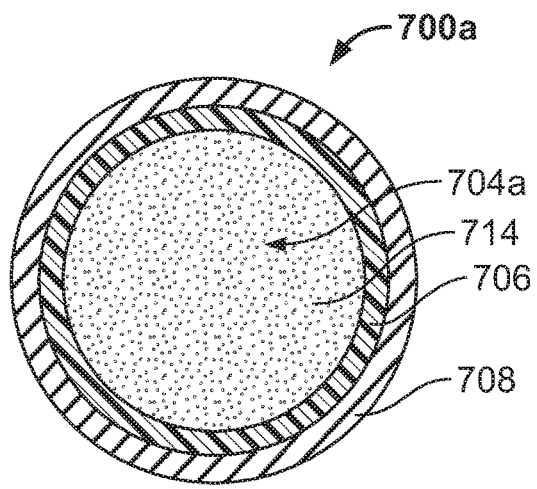
FIG. 40 is a cross-sectional view of a curable conformable composite precursor having a conformable core including a packing material.
Figure 41:
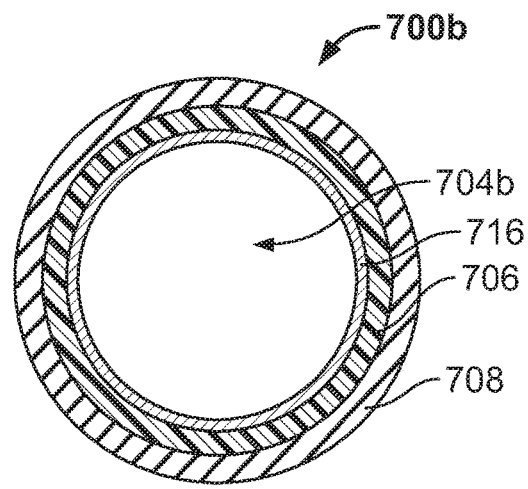
FIG. 41 is a cross-sectional view of a curable conformable composite precursor having a hollow tubular conformable core.
Figure 42:
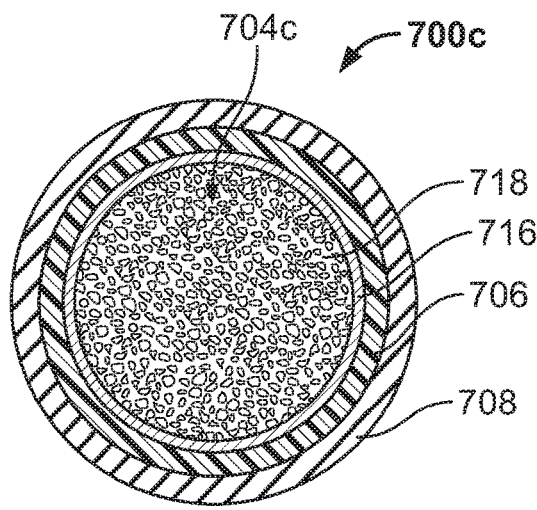
FIG. 42 is a cross-sectional view of a curable conformable composite precursor having a hollow tubular conformable core filled with a packing material.
Figure 43:
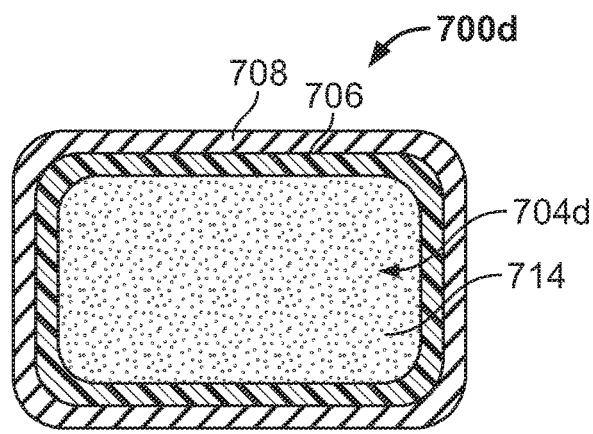
FIG. 43 is a cross-sectional view of a curable conformable composite precursor having a conformable core including a packing material and a generally rectangular cross-section.

Core 602 can be composed of one or more wires or elongated rods 612 contained within a packing or filler material 604. Precursors 600*a*, 600*b*, and 600*c* have a single central wire or rod 612 while precursor 600*d* has two non-central wires or rods 612, which makes precursor 600*d* more difficult to bend in the width dimension W than the height dimension H as illustrated in FIG. 39. Wire 612 generally has a single solid conductor, but it can be hollow as in precursor 600*b*. Wire 612 preferably has a round cross-section, but any suitable shape may be used. Wire 612 may be made from metal (or any plastically deformable material) that is suitable to be bent into a desired shape and to retain the desired shape. Due to their availability and desirable properties, copper, aluminum, stainless steel and combinations thereof are preferred as materials for wire 612. The material of wire or rod 612 should have a relatively low yield strength so that it can be plastically-deformed or conformed by hand, but otherwise hold its shape before and during curing. In contrast, springs have a high yield strength and even if plastically deformed will bounce back. Wire 612 preferably has a diameter ranging from about 1 mm to about 15 mm, more preferably between about 2 mm and 10 mm, and most preferably between about 3 mm and about 8 mm. Packing or filler 604 is made from a suitable lightweight, void-containing material such as a polymer material or cured or solidified foamed polymer or other cellular materials such as a honeycomb type material to provide a desired cross-section to the precursor during shaping and curing into the cured product. The material for filler 604 preferably maintains its shape under compression of compressor layer 608, is flexible to permit contouring or fitting without recoiling during curing and is compatible with the prepreg resin. One suitable material is foamed polyurethane. Typically, packing 604 is unitary and bendable, but it can also be made from a plurality of discrete pieces. Packing 604 can also be made from a particulate material, which can be agglomerated or sintered together. The material for packing 604 preferably has a density of less than about 10 lbs/cubic foot or about 0.16 g/ml. The material if a foam may be open cell or closed cell. Generally, the purpose of packing 604 is to increase the diameter of core 602 and therefore the diameter of precursor 600 while supporting fiber layer 606, as well as increasing the diameter or cross-section of the cured product.

Fiber layer 606 contains a fiber containing cloth around core 602. Suitable fibers include glass fiber, carbon fiber, graphite fiber, aramid fiber, cellulose fiber, silicon carbide fiber, and mixtures thereof. Aramid may include meta-aramid such as Nomex®, para-aramid such as Kevlar®, and mixtures thereof. The cloth may be wrapped around core 602 in a convolute with the cloth being as wide as precursor 600 is long or it may be wrapped many times on a bias to the length of precursor 600 in an overlapping spiral. Preferably the cloth is a braided sleeve 610 impregnated with a resin similar to sleeve 170. Generally, fiber layer 606 is in direct contact with core 602, i.e., there is no release layer or film between fiber layer 606 and core 602 to provide for the removal of core 602 after curing of fiber layer 606.

The outer compressor layer 608 can comprise a vacuum bag, a vacuum storage sleeve, shrink tape, shrink tubing or an elastic storage sleeve. The vacuum storage sleeve may be comprised of polyurethane film, polyethylene film, Mylar, latex, PVC or other materials. The material for a vacuum storage sleeve is preferably thermo-bondable to reliably hold a vacuum seal and have low permeability to maintain a vacuum for the storage life of precursor 600 without leaking or releasing its vacuum compression upon precursor 600. The material is preferably highly flexible to permit shaping of precursor 600. Stretchlon bagging film is suitable.

Precursor 600, for orthosis purposes, typically has a diameter less than or equal to about 1 inch or about 25 mm or a circumference less than or equal to about 3 inches or about 76 mm. Precursor 600 may be made by any suitable method known in the art.

In another embodiment, a linear precursor 700 is provided having variants 700*a*, 700*b*, 700*c* and 700*d* as illustrated in FIGS. 40-43, respectively. Linear precursors 600 and 700 are similar such that the discussion of precursor 700 is generally limited to the differences with precursor 600. Where parts are the same or similar between precursors 600 and 700, the same reference numerals may be used or the reference numerals may differ by 100. Precursor 700 has a core 704, a fiber layer 706 and an outer compressor layer 708. Cores 704*a* and 704*d* include a packing 714 like packing 604 typically without a wire. Cores 704*a* and 704*d* differ by cross-sectional shape—circular vs. rectangular. Cores 704*b* and 704*c* include a tube 716. Tube 716 can be made from copper or aluminum, for example. Tube 716 can have various suitable voids to promote controlled bending of the tube. Suitable voids include a plurality of regularly spaced rectangular voids (like slots) substantially parallel to the circumference of tube 716 assuming that tube 716 has a circular cross-section. Regular spacing here refers to regular spacing along the length of the tube 716. Adjacent rectangular voids or slots may occupy different angular locations to facilitate bending in different directions. Core 704*b* is illustrated as being otherwise hollow while core 704*c* has a packing 718. Packing 718 can be removable from the cured precursor. Packing 718 can be the same or similar as packing 604. Packing 718 can be selected so that it is easily removable from the cured precursor 700*c* and to smooth bends in tube 716, i.e., prevent kinking of tube 716 during bending. Similar packing material includes, for example, various aggregates, which may be sand, finely divided limestone or glass beads.

Figure 44:
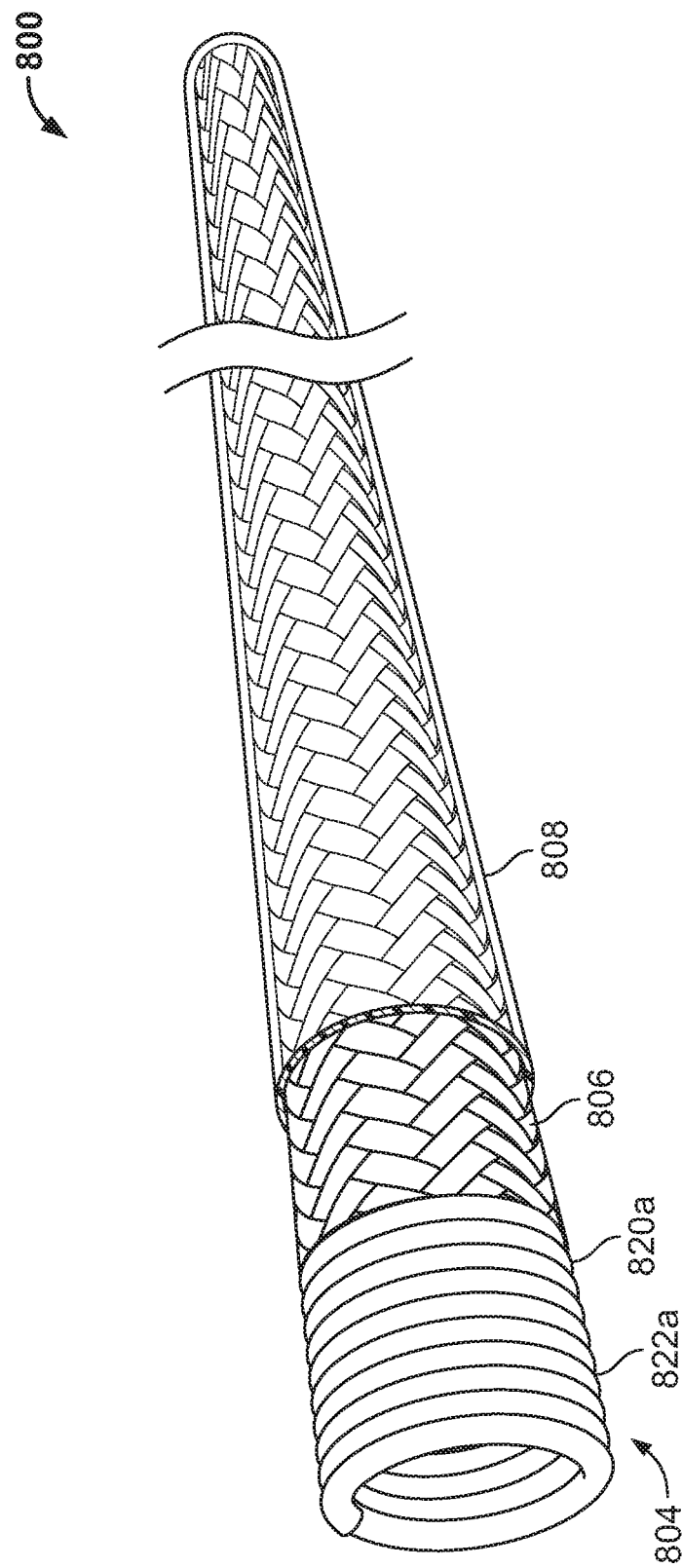
FIG. 44 is a perspective, partial sectional view of a curable conformable cylindrical composite precursor having a conformable coiled-wire support structure or core.

In another embodiment, a linear curable, conformable precursor 800 is provided as illustrated in FIG. 44. Linear precursors 600, 700 and 800 are similar such that the discussion of precursor 800 is generally limited to the differences from precursors 600 and 700. Where parts are the same or similar between precursors 600, 700 and 800, the same reference numerals may be used or the reference numerals may differ by 100. Precursor 800 has a core 804, a fiber layer 806 and an outer compressor and packaging layer 808. The principal structural difference between precursor 600 and 800 is that core 804 has a wire with a plurality of repeating bends substantially along its entire length such as wire coil 820 or wire waveform 821. Core 804 provides shape to the precursor like void-containing core 602 and serves to hold the shape of precursor 800 after shaping. The principal functional difference between precursor 600 and 800 is that the length of precursor 800 may be adjusted by a user because core 804 and coil 820 can be elongated or shortened.

Figure 45:
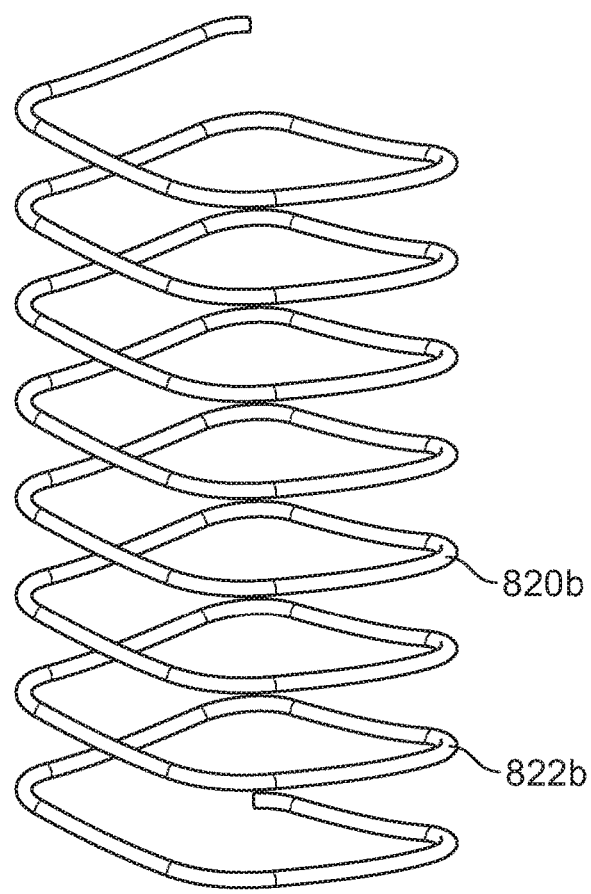
FIGS. 45, 46 and 46A-C illustrate alternate embodiments of a conformable support structure, which may be a metal or wire core.
Figure 46:
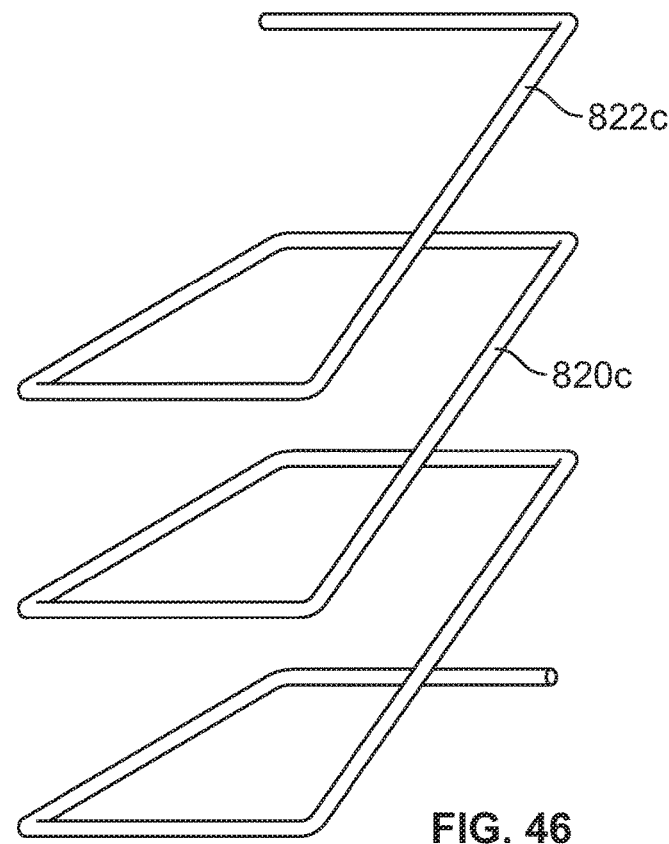

The cross section of linear precursor 800 may have any suitable shape by using different coils 820. For example, linear precursor 800 may include coils 820*a*, 820*b*, or 820*c* as illustrated in FIGS. 44-46 or any other suitable coil. Coil 820*a* is circular. The individual coils of coil 820*a* are closely spaced and the coils are substantially uniform including having a substantially uniform pitch. Coil 820*b* is rectangular or squarish with a substantially uniform pitch and spaced coils allowing the length of coil 820*b* to be manually shortened or lengthened. Coil 820*c* is rectangular with a varying pitch and spaced coils allowing the length of coil 820*c* to be manually shortened or lengthened. Coil 820 may have different sections of different spacings, pitch or other characteristics to provide precursor 800 with suitable variable bending characteristics. Coil 820 can include or be a coiled wire 822. Core 804 can be hollow within coil 820 as illustrated or it can have a packing like packing 604. A particular packing may be desirable if the coil 820 has spaced coils.

Figure 46A:
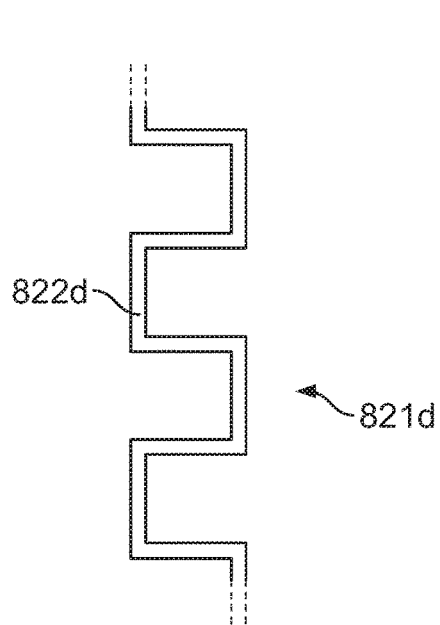
Figure 46B:
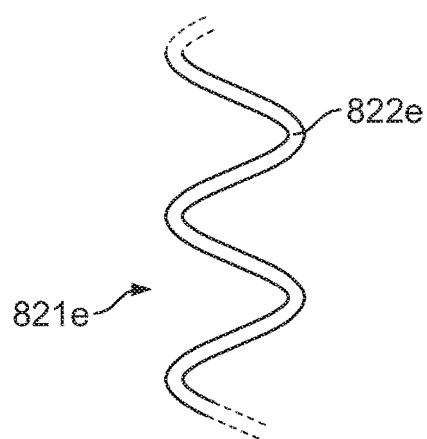
Figure 46C:
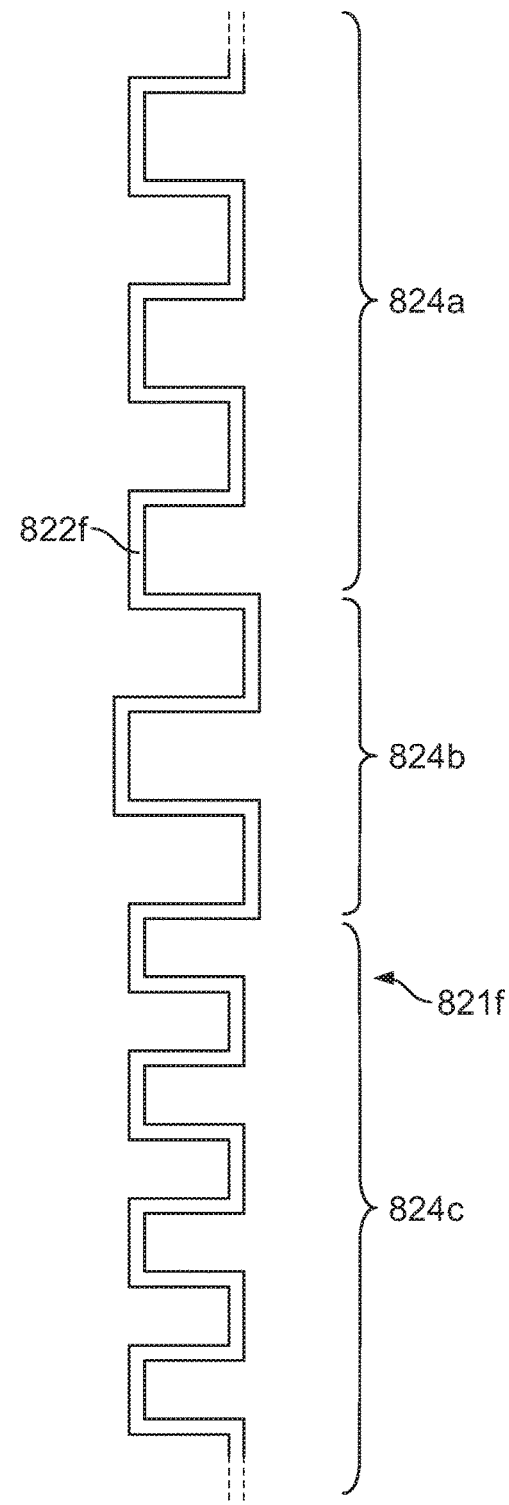

Alternatively, core 804 may include one or more waveforms 821 as illustrated in FIGS. 46A-46C. If core 804 has two waveforms 821, the waves of each waveform 821 can be opposed across the width of core 804. Wire 822*d* is bent in the form of a square wave. Wire 822*e* is bent in the form of a sinusoidal wave. The spacing and height of the "peaks" and "valleys" may vary to provide preferred bending characteristics and to vary the width of the precursor. For example, wire 822*f* shown in FIG. 46C has three sections, 824*a*, 824*b* and 824*c*. Section 824*a* has a square wave. Section 824*b* has a wave with the same spacing as section 824*a* but higher peaks and lower valleys. Section 824*c* has peaks and valleys of the same "elevation" as section 824*a* but the spacing has varied. Waveform 821 may be sinusoidal, square wave, triangle wave, serpentine, alternating chained semicircles or any other suitable shape and is generally substantially planar, but it can rotate out of the plane depending on the application.

Wire 822 should have a relatively low yield strength so that it can be plastically deformed or conformed by hand, but otherwise hold its shape before and during curing. In contrast, springs have a high yield strength and even if plastically deformed will bounce back and thus do not hold a shape to which they are conformed. Also wires like those used for holding tension such as structural cables, suspension cables, and brake cables do not hold their shape and do not plastically-deform by hand.

Figure 47:
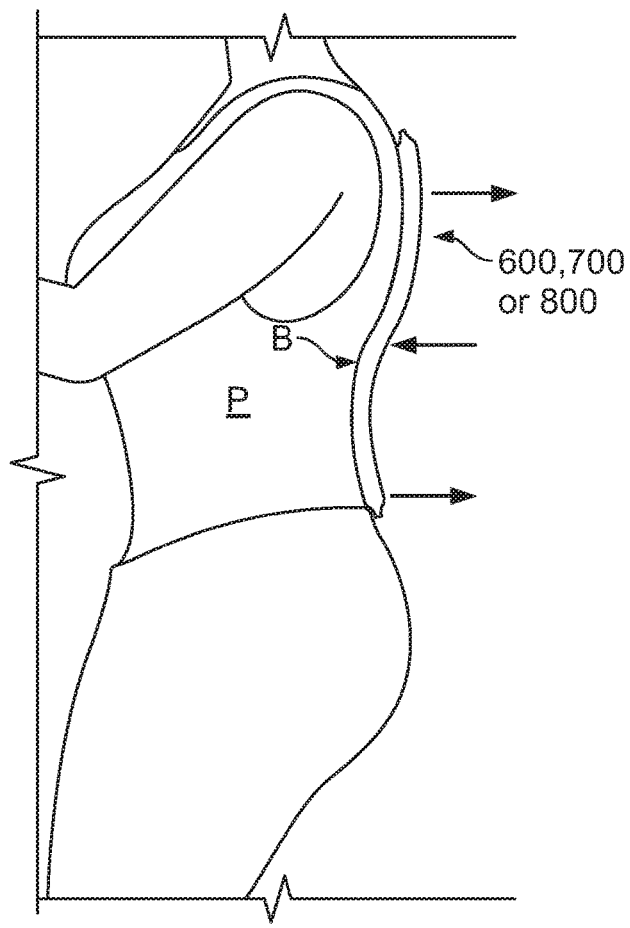
FIG. 47 is a side elevation view illustrating the customizing of a curable, conformable cylindrical composite precursor to match a person's back.
Figure 48:
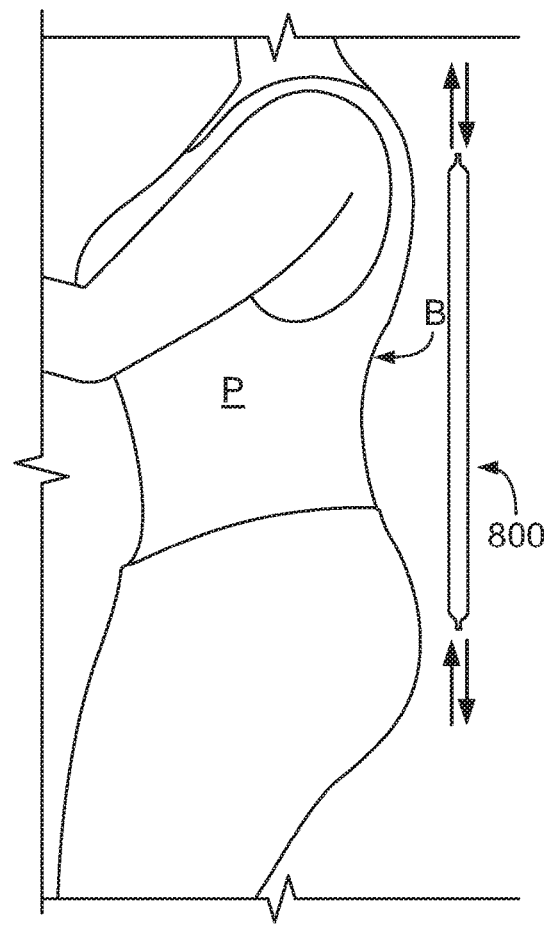
FIG. 48 is a side elevation view illustrating the extending or shortening of a conformable cylindrical composite precursor to conform to the length of a person's back.

As shown in FIGS. 47-48, precursor 600, 700 or 800 is bent (plastically deformed) to match or conform to a certain shape such as the body of a patient P, particularly the patient's back B. As shown in FIG. 48, precursor 800 can also be lengthened or shortened as necessary depending on coil 820. The lengthening and shortening is typically performed before the conforming shown in FIG. 47 although it can be done during the conforming particularly if the amount of shortening or lengthening is relatively small.

Once precursor 600, 700, or 800 is in the desired shape, it can then be cured in an oven in accordance with the specifications of the prepreg sleeve manufacturer. Generally, curing involves heating precursor 102 to a suitable temperature, generally, in excess of 212° F. or 100° C. Curing of precursors 600, 700 and 800 is similar to curing of precursor 102, previously discussed. After the cure is complete, compressor layer 608, 708 or 808 may or may not be removed depending on the application and possibly the desired appearance. Like orthosis 104 straps and clamps may be attached to the cured precursor 600, 700 or 800 to make a finished device.

External Frame Orthosis

Figure 49:
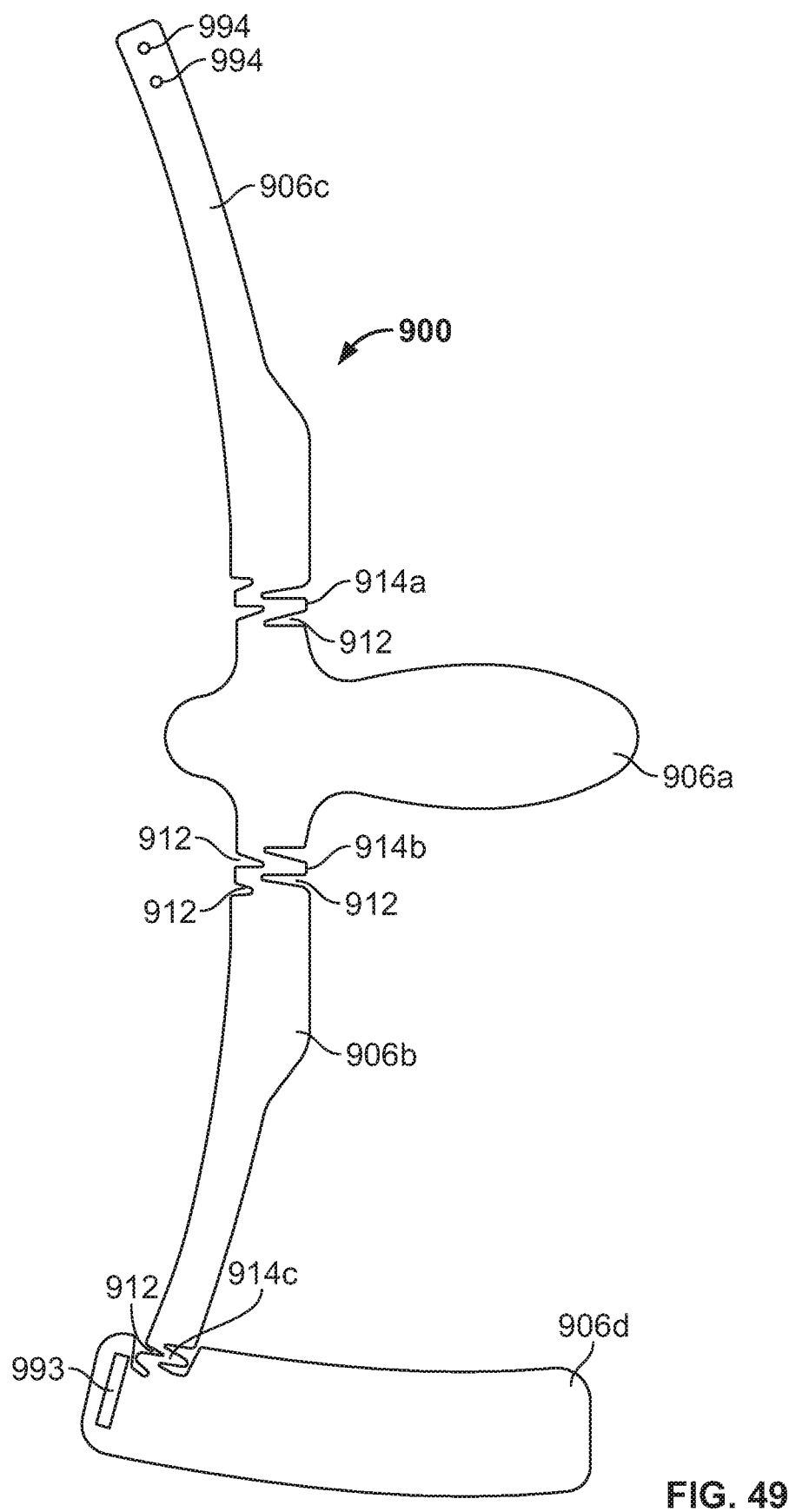
FIG. 49 is a front elevation view of an initially flat conformable core suitable for use in making an ankle-foot orthosis.

In another embodiment of the invention, a conformable supporting structure or core 900, a composite precursor 902, and an ankle-foot orthosis 904 are provided as illustrated in FIGS. 49-52. Conformable core 900 is illustrated in FIG. 49. Conformable core 900 can be very similar to conformable cores 100, 200, 300, 400 and where parts are the same or similar between these supporting structures, the same reference numerals may be used or the reference numerals may differ by multiples of 100. In particular, it can have any of the voids for promoting plastic deformation previously discussed including slots 110, triangular voids 112 for zig-zag 114 (illustrated as voids 912 and zig-zags 914), and opened-ended voids 127. Conformable core 900 here has zig-zags 914*a* and 914*b* for dorsiflexion and zig-zag 914*c* for calf band tilt. However, it may also have voids that are intended to appear in the finished product, orthosis 904, such as a rectangular slot 993 for a strap and fastener holes 994. Typically, conformable core 900 is unitary from a single sheet of metal, but not necessarily so. Generally, conformable core 900 does not have ridges 136 or valleys 154 for providing strength to the finished product. Conformable core 900 has a foot member 906*a*, calf upright member 906*b* and 906*c*, and calf band member 906*d*.

Figure 50:
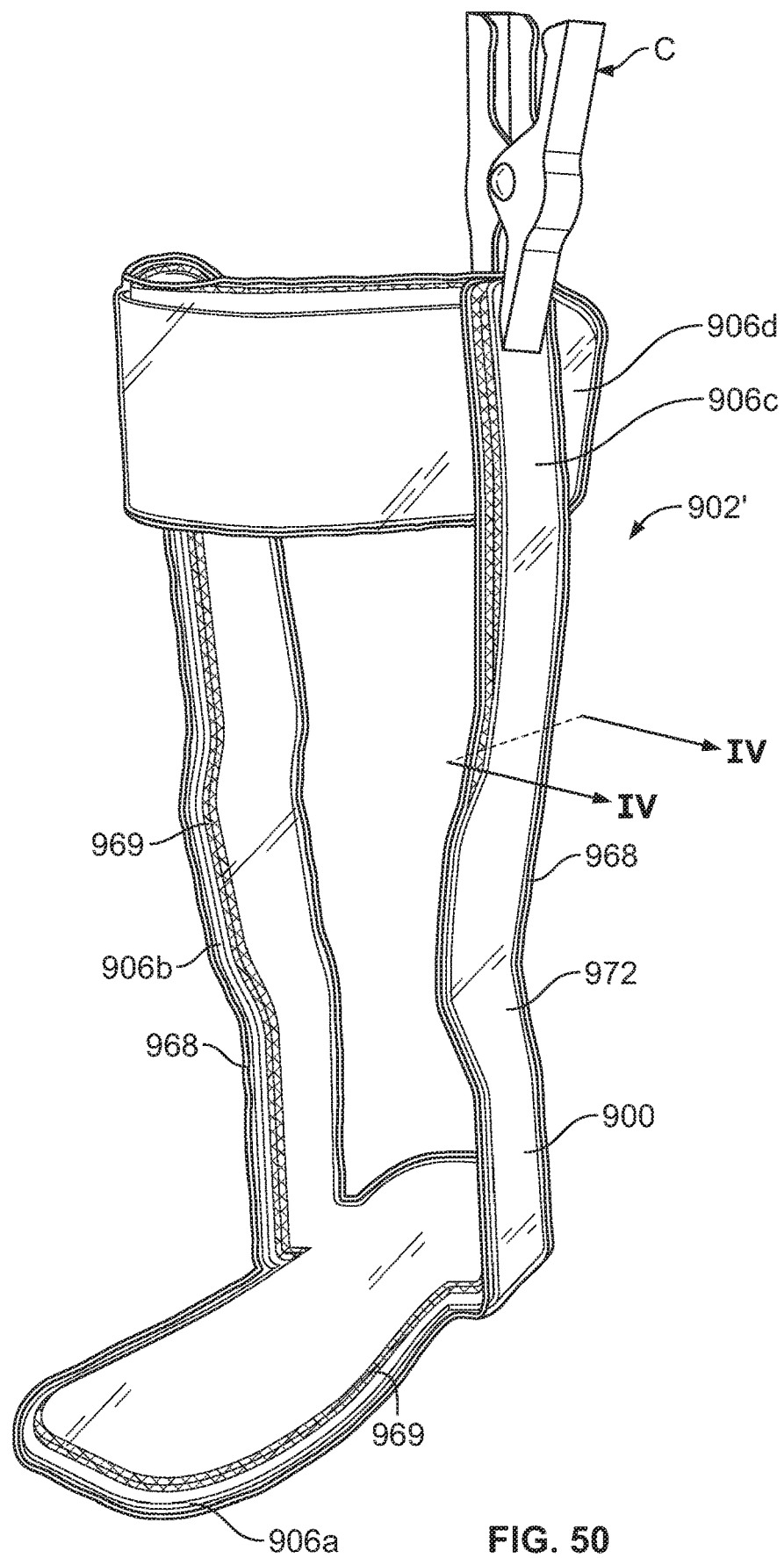
FIG. 50 is a perspective view of a curable composite precursor incorporating the conformable core of FIG. 49 after having been conformed to a patient's leg (not shown).
Figure 52:
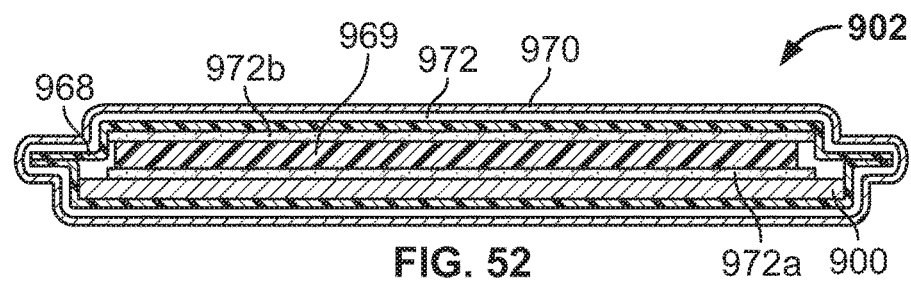
FIG. 52 is a cross-sectional view of the curable composite precursor of FIG. 50 taken along line IV-IV in FIG. 50.

As can be best seen in FIGS. 50 and 52, precursor 902 has conformable core 900, a release layer 972*a*, a fiber layer 969, and a second release layer 972*b*. In addition, precursor 902 is contained in a vacuum bag 968 containing precursor 902, in an evacuated environment thereby enabling fiber layer 969 to be properly cured in a non-vacuum oven, as previously described. Vacuum bag 968 acts as a compressor during the curing process in a non-vacuum or atmospheric oven. Vacuum bag 968, as other vacuum bags described herein should be able to maintain or substantially maintain a vacuum during the oven curing process, resulting in compression of the resin impregnated carbon fiber material contained therein, which facilitates proper formation of the cured carbon fiber composite. One advantage of the present invention is that the uncured precursors, such as precursor 902, for example, can be produced, packaged and stored for long periods of time, such as 3 months, 6 months, a year or longer, until use, such as by an orthotist in the case of orthotic precursors, for example. To further facilitate such long-term storage, the precursor optionally can be double bagged as shown in FIG. 52, in which external gas impermeable storage bag 970 (not shown in FIG. 50) contains vacuum bag 968 and precursor 902 in a gas impermeable environment. Storage bag 970 can be vacuum sealed when enclosing vacuum bag 969 if desired, and there can be a space 972 between bag 969 and storage bag 970, typically when storage bag 970 is not vacuum sealed around vacuum bag 969. Suitable films for vacuum bagging allows about 15 psi of pressure (atmospheric pressure) to be applied to the prepreg during curing. Suitable vacuum bagging films can be selected from polyurethane, and nylon film, for example. Release films are also well known in the art and can be a fluorocarbon and nylon film, for example. The release film can be permeable or perforated allowing excess epoxy resin to be removed. Fiber layer 969 generally is not part of a braided fiber sleeve. Fiber layer 969 may have a plurality of plies and the plies have different fiber orientations. Not using a fiber sleeve allows greater control over the "layup" and thickness of fiber layer 969 including number of layers, fiber weight, resin type, and fiber orientation optimized for the finished product. Fiber layer 969 is impregnated with a resin like sleeve 170 as discussed earlier. Precursor 902 may have additional holes and features for attaching additional orthotic elements. Preferably, release layers 972 comprise a siliconized fiber/cardboard carrier to reduce cost, provide some structure for assembly of the prepreg layup and improve the surface finish of the cured precursor.

Precursor 902 can be customized by appropriately bending or otherwise shaping precursor 902 to conform to a desired shape such as the leg of a patient where precursor 902 is intended to overlay. Specifically, precursor 902 can be bent upwards with a patient's foot on foot member 906*a* at zig-zags 914*a* and 914*b* and then calf upright 906*b* and 906*c* can be rotated backwards and forwards at zig-zags 914*a* and 914*b* to achieve a desired dorsiflexion. Calf member 906*d* is bent around the front of a patient's calf and is tilted at zig-zag 914*c* to match the patient's leg. The calf member 906*d* is then clamped with clamp C to upright member 906*c*.

The customized precursor 902' is cured at temperatures in excess of 212° F. or 100° C. as discussed earlier. After curing, vacuum bag 968, conformable core 900, and release films or sheets 972 are removed leaving an unfinished but cured orthosis 904. The unfinished orthosis is lightly buffed on the edges with a buffing cone to make the edges smooth. A pad 995 is added to the calf band 996. A chafe 997 is fastened by fasteners 998 through holes corresponding to holes 994. A tibial strap 999 is threaded through the slot corresponding to slot 993 and chafe 997. Tibial strap 999 may include hook and loop fasteners such as Velcro® brand fasteners.

Mesh Frame and Integral Frame Orthoses

Figure 53:
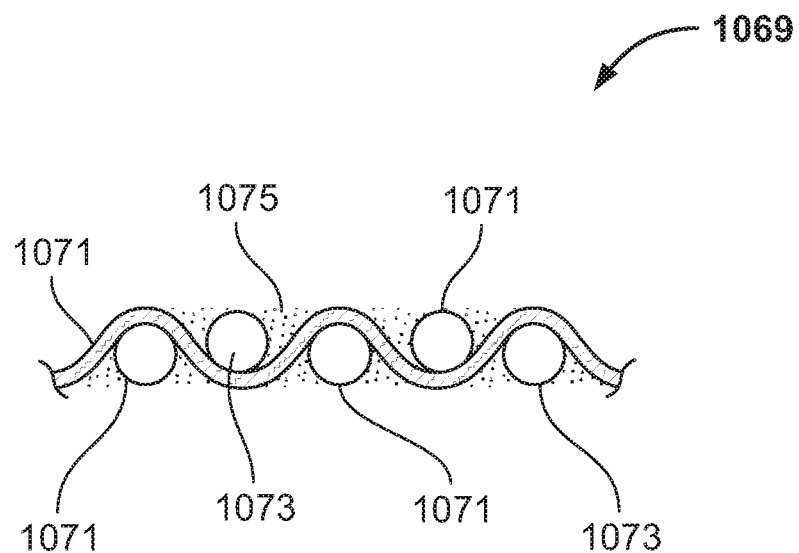
FIG. 53 is a schematic cross-sectional view of a resin-impregnated fabric useful in curable composite precursors.

The various precursors discussed earlier can have fiber layers 169, 606, 706, 806, and 969 and sleeves 570 having ductile properties. It is contemplated that the ductile properties can be provided by ductile fibers interwoven or integral in the fabric of fiber layers. An exemplary resin-impregnated fiber layer 1069 is shown schematically in cross-section in FIG. 53. It has reinforcing fibers 1071 including glass fiber, carbon fiber, graphite fiber, aramid fiber, silicon carbide fiber, cellulose fiber, silicon carbide fiber and mixtures thereof. Aramid may include meta-aramid such as Nomex®, para-aramid such as Kevlar®, and mixtures thereof. Fabric 1069 also has interwoven in it ductile fibers 1073. Ductile fibers 1073 can include any suitable fiber such as ductile wires of copper, aluminum or steel, particularly mild steel and stainless steel. Fabric 1069 also has a suitable resin 1075 represented by stippling in FIG. 53. Resin 1075 may be light-activated, UV-activated or heat-activated. The resin system can be any suitable resin, e.g., one that suitably adheres to the fabric of layer 1069 when cured, including, for example, an epoxy that includes the proper curing agent Fibers 1071 and 1073 are typically used in both the weft and warp yarns, but it is contemplated that ductile fibers could be omitted from the weft or warp yarns. The ratio of fibers 1071 and 1073 can be any suitable ratio in layer 1069. Fiber layer 1069 can be used to make precursors that do not have a frame separate from fiber layer 1069.

The various precursors discussed earlier can have a conformable frame or conformable core based on a ductile mesh 1080 instead of conformable frames or cores 100, 200, 300, 400, 500 or 900 having ductile fibers 1082 like ductile fibers 1073. Ductile mesh 1080 shown schematically in FIG. 54 can also be impregnated with the resin used in the fiber layer.

Method of Making a Custom Shaped Product

In another embodiment, a method of making a custom shaped product is provided. The method typically includes placing a precursor against an object. The precursor has a frame or core that can be conformed to the object and retain the shape of the object once the precursor is no longer against the object. The precursor also has a fiber layer including a thermally curable or light-activated resin, and often an outer compressor layer. The precursor can also have one or more release layers as discussed earlier. The compressor layer may have release properties obviating the need for a release layer. The precursor can be any of the precursors previously described and similar ones. Like those previously discussed, it may be substantially planar, and may have voids in it to promote plastic deformation of the precursor or have raised ridges to increase the strength of the finished product or to limit plastic deformation of the precursor. It may include one or more wires, which may be substantially straight or have a plurality of bends. The conformable frame or core may be located between two fiber layers, within a braided sleeve or be wrapped in a fiber fabric. Alternatively, it may not be so located like precursor 902.

The object can be an object that cannot be placed in a curing oven because it is too big for the oven to be used or is sensitive to curing temperatures. Examples of the object include a live human or mammalian body such as a limb. If a human or mammalian body, the body may be clothed. The precursor may be placed in direct contact with the object or against an intermediate object such as padding of the intermediate object becomes part of the custom shaped product. Generally, the object is not a mold corresponding to another object, but the object may be an anatomical mold of a person's limb, or an external frame that has been adjusted to the shape of a person's limb. The object may be a virtual object, e.g., a computer model that has been created using measurements of a person's body such as a limb.

The next step is to fit the precursor. Fitting involves plastically deforming the precursor to approximately match the shape of the object, which involves plastically deforming the frame or core. If the purpose of the fitting is to match the shape of a body part, the fitting can be done by pressing the fitting against the body part, using an anatomic mold, using an external frame that has been adjusted to the shape of a person's limb or using a virtual object as discussed earlier. Specific deformations include bending the frame around an axis parallel to the plane of the frame particularly in a slotted portion of the frame. Generally, the slotting is substantially parallel to the axis. Another deformation is bending the frame around an axis perpendicular to the frame, particularly in a portion of the frame having open-ended voids such as a zig-zag. A third deformation is bending the frame around an axis within the plane of the frame, i.e, twisting, particularly in a portion of the frame having open ended voids such as a zig-zag. A fourth deformation is elongating or shortening the core or frame, particularly in a serpentine portion of the frame. A fifth deformation is to bend the core around an axis perpendicular to its length. These above deformations are generally performed locally such that different deformations may be applied to different parts of the precursor. Also, the plane of the frame or length of the core can refer to the plane or length axis local to where the deformation is occurring.

Fitting may also involve plastically deforming the precursor so that the precursor and ultimately the cured precursor can be properly attached to other structures or precursors. Examples of such attachments were discussed earlier with respect to footbeds and to male and female retention pieces. Any kind of curable, conformable precursor may be attached to another. Before doing such a fitting it may be necessary to do a coarse, preliminary or first fitting such as bending a planar precursor into a partially cylindrical shape before making any attachments and then doing a second fitting to finalize the shape. Attaching may include mating a male and a female connector together. The female connector may be any suitable female connector including bar acceptor 122 or female connector 394b. The male connector may be any suitable male connector including a bar such as upright 180, 280, the precursor itself such as frame 500, or male connector 394a. The connector most directly connected to the precursor may be internal or external to the precursor's outer compressor layer. The most directly connected connector may be located adjacent a zig-zag portion of the conformable core or frame. Once necessary attachments are made, the second fitting or customization (if there was a first) may occur while the precursor is placed against the object. The second fitting can include any portion of the fitting as earlier described and typically includes plastically deforming the zig-zag portion of the frame adjacent the mated connectors so that the precursor conforms to the object.

After the fitting, the connectors may be detached from each other and/or from the precursor. The precursor is removed from the object if it was shaped on the object. The conformable support structure retains the conformed shape of the precursor (including any compressor or packaging) after shaping and during curing of the fiber layer. Next, the fitted precursor is cured. Typically, when a thermoset resin is used in the fiber layer, the cure is done inside an oven operated at ambient pressure. The precursor may be placed inside an insulated bag in the oven to reduce the rate of heating and cooling during the curing process resulting in an improved cured product. The rate of heating and cooling of a heat-curable, conformable composite precursor can be controlled in any suitable manner. In one aspect, this method involves using an insulating bag to control the heating/cooling rate during curing. After shaping, the packaged construct is placed in the insulating bag and the bag is subsequently placed in an oven that is held at constant temperature. The rate of heating of the composite within the insulating bag will be decreased by the insulating quality of the bag, improving the quality of the cured composite. It is thus possible to use an oven programmed for a constant temperature to cure the precursor. When the fiber layer includes a light-activated resin, the resin is cured by exposing the fiber layer to radiation including radiation of the appropriate wavelength.

The cured precursor may then undergo various finishing steps. The compressor layer and any release films or sheets may be removed if so desired. The compressor layer can also serve as a cosmetic layer that bonds to the fabric during the curing and is therefore not removed. Connectors may be removed. The cured precursor may be attached to other braces such as a foot brace or knee brace. For precursors having a packing or an external frame, the packing or external frame may be removed. Padding and straps may be attached to the cured precursor.

The invention may be used in numerous applications, such as wherever use of conformable bar or sheet stock finished into a desired rigid shape would be desired or useful. More specific applications include orthoses, including but not limited to orthoses for leg, arm, finger, back, and neck, prosthetics, seating and positioning systems. Additional applications include sports equipment, custom pads for contact sports like football and hockey.

While the invention has been described with respect to certain embodiments, as will be appreciated by those skilled in the art, it is to be understood that the invention is capable of widespread applicability, numerous changes, modifications and rearrangements, and such widespread applicability, changes, modifications and rearrangements are intended to be covered by the following claims.

What is claimed is:

1. A curable, conformable composite precursor having an initial shape that can be manually manipulated into a desired shape different from the initial shape, before being cured, and curable by heating without an externally applied vacuum into a final product having the desired shape, the precursor comprising:
   a conformable fabric impregnated with an uncured resin;
   a conformable support structure for supporting the impregnated fabric, the support structure being plastically deformable at one or more locations in at least one direction by hand so that the conformable support structure can be deformed into a shape and the support structure permanently retains the shape after the deforming; and
   a compressor for compressing the fabric so that the fabric remains impregnated with the resin during curing, the compressor containing the fabric and conformable support structure.

2. The precursor of claim 1 wherein the fabric comprises a braided sleeve, the braided sleeve surrounding at least part of the conformable support structure.

3. The precursor of claim 2 further comprising a polymer foam at least partially surrounded by the sleeve, wherein the conformable support structure comprises a wire at least partially surrounded by the polymer foam.

4. The precursor of claim 2 wherein the conformable support structure comprises a wire, the wire being substantially helical or in a waveform pattern.

5. The precursor of claim 2 wherein the conformable support structure comprises a wire, the compressor completely surrounding and forming a package around the impregnated fabric and support structure.

6. The precursor of claim 5 wherein the compressor is a vacuum-sealed enclosure that conforms to the shape of the impregnated fabric and the support structure.

7. The precursor of claim 2 wherein the conformable support structure comprises a thin substantially planar layer of plastically deformable material.

8. The precursor of claim 7 wherein the thin layer is metal and comprises a plurality of elongated open-ended voids forming a zig-zag pattern in the plane of the layer.

9. The precursor of claim 8 further comprising a connector for connecting the precursor to an external device, the connector being adjacent the zig-zag pattern.

10. The precursor of claim 9 further comprising an acceptor having a cavity in which the connector is received, the acceptor located adjacent the zig-zag pattern and within the compressor.

11. The precursor of claim 10 wherein the cavity or the connector has a release film or coating for facilitating the removal of the connector from the cavity.

12. The precursor of claim 7 wherein the layer comprises a plurality of substantially parallel elongated voids or a pair of opposed elongated voids.

13. The precursor of claim 7 wherein the layer comprises a ridge for resisting plastic deformation.

14. The precursor of claim 13 wherein the layer further comprises a plurality of substantially parallel elongated voids across the ridge.

15. The precursor of claim 7 wherein the compressor comprises a vacuum bag enclosing the conformable support structure and fabric.

16. The precursor of claim 7 wherein the support structure has a corner, the corner having a protuberance on its inside for reducing bunching of the braid around the corner.

17. The precursor of claim 7 wherein the layer comprises sheet metal.

18. The precursor of claim 7 wherein the conformable support structure comprises a plurality of connected elongated members.

19. The precursor of claim 18 wherein at least one of the members comprises two extremities and a serpentine portion remote from the two extremities, the serpentine portion for facilitating plastic deformation of the member in a lengthwise direction.

20. The precursor of claim 18 wherein the plurality of connected elongated members at least partially enclose an open area.

21. The precursor of claim 1 wherein the fabric comprises at least one fiber selected from the group consisting of glass fiber, carbon fiber, graphite fiber, aramid fiber, silicon carbide fiber, cellulose fiber, ductile metal fiber and mixtures thereof.

22. The precursor of claim 1 wherein the precursor is a precursor for an orthosis or part of an orthosis.

23. The precursor of claim 1 wherein the precursor has been plastically deformed to match part of a body of a person.

24. The precursor of claim 23 wherein the compressor comprises a vacuum sleeve enclosing the conformable support structure and fabric.

25. The precursor of claim 1 further comprising a first release layer, wherein the fabric is in the form of a fabric layer, the first release layer located between the conformable support structure and the fabric layer.

26. The precursor of claim 1 wherein the conformable support structure is made of metal.

27. A curable, conformable composite precursor having an initial shape and curable into a rigid product having a desired shape different from the initial shape, the precursor comprising:
a conformable fabric impregnated with an uncured fluid resin;
a conformable core structure supporting the fabric, the core structure being plastically deformable at one or more locations in at least one direction so that the conformable core structure can be deformed into a shape and the core structure permanently retains the shape after the deforming; and
a packaging material enclosing the fabric from the atmosphere.

28. The precursor of claim 27 wherein the fabric comprises a braided sleeve, the braided sleeve surrounding at least part of the conformable core structure.

29. The precursor of claim 28 wherein the conformable core structure comprises a layer of a plastically deformable material.

30. The precursor of claim 29 wherein the layer comprises an elongated void for facilitating plastic deformation.

31. The precursor of claim 29 wherein the layer is substantially planar and comprises a plurality of elongated open-ended voids forming a zig-zag pattern in the plane of the layer.

32. The precursor of claim 31 further comprising a connector for connecting the precursor to an external device, the connector being adjacent the zig-zag pattern.

33. The precursor of claim 29 wherein the layer comprises a plurality of substantially parallel elongated voids or a pair of opposed elongated voids.

34. The precursor of claim 29 wherein the layer comprises a ridge for resisting plastic deformation and for strengthening the rigid product.

35. The precursor of claim 34 wherein the layer further comprises a plurality of substantially parallel elongated voids across the ridge.

36. The precursor of claim 29 wherein the packaging material is a compressor that comprises a vacuum sleeve enclosing the layer and the fabric.

37. The precursor of claim 29 further comprising a first release layer, wherein the fabric is in the form of a fabric layer, the first release layer located between the core structure and the fabric layer.

38. The precursor of claim 37 wherein the packaging material comprises a vacuum sleeve enclosing the core structure and the fabric layer.

39. The precursor of claim 29 wherein the layer comprises sheet metal.

40. The precursor of claim 27 further comprising a filler material between the conformable core structure and the impregnated fabric.

41. The precursor of claim 40 wherein the conformable core structure comprises an elongated body of substantially uniform cross-section.

42. The precursor of claim 27 wherein the conformable core structure comprises a wire, the packaging material completely surrounding the conformable core structure.

43. The precursor of claim 27 wherein the fabric comprises at least one fiber selected from the group consisting of glass fiber, carbon fiber, graphite fiber, aramid fiber, silicon carbide fiber, cellulose fiber, ductile metal fiber and mixtures thereof.

44. The precursor of claim 27 wherein the precursor is a precursor for an orthosis or part of an orthosis.

45. The precursor of claim 27 wherein the precursor has been plastically deformed to match part of a body of a person.

46. The precursor of claim 27 wherein the conformable core structure is plastically deformable at one or more locations in at least one direction by hand.

47. The precursor of claim 27 wherein the conformable core structure comprises a plurality of connected elongated members.

48. The precursor of claim 47 wherein at least one of the members comprises two extremities and a serpentine portion remote from the two extremities, the serpentine portion for facilitating plastic deformation of the member in a lengthwise direction.

49. The precursor of claim 47 wherein the plurality of connected elongated members at least partially enclose an open area.

50. The precursor of claim 27 wherein the conformable core structure is made of metal.

51. A curable, conformable bar stock member having an initial shape and curable into a rigid product having a desired shape different from the initial shape, the curable, conformable bar stock comprising:
    a conformable fabric impregnated with an uncured resin;
    a conformable support structure for supporting the impregnated fabric, the support structure being plastically deformable at one or more locations in at least one direction by hand so that the conformable support structure can be deformed into a shape and the support structure permanently retains the shape after the deforming; and
    a packaging material enclosing the impregnated fabric.

52. The bar stock member of claim 51 wherein the packaging material is a compressor for compressing the fabric so that the fabric remains impregnated with the resin, the compressor containing the fabric and conformable support structure.

53. The bar stock member of claim 51 wherein the packaging material encloses the conformable support structure.

54. The bar stock member of claim 53 wherein the packaging material is vacuum sealed over the impregnated fabric and the support structure.

55. The bar stock member of claim 51 wherein the packaging material is substantially gas impermeable and is vacuum sealed over the conformable impregnated fabric.

56. The bar stock member of claim 51 wherein the conformable support structure is made of metal.

57. The bar stock member of claim 51 wherein the fabric comprises a braided sleeve, the braided sleeve surrounding at least part of the conformable support structure.

58. The bar stock member of claim 57 wherein the packaging material is a compressor for compressing the fabric so that the fabric remains impregnated with the resin, the compressor containing the fabric.

59. The bar stock member of claim 57 wherein a portion of the conformable support structure is located outside the compressor, the portion having one or more apertures for attaching the bar stock member.

60. The precursor of claim 51 wherein the precursor is a precursor for an orthosis or part of an orthosis.

61. The precursor of claim 51 wherein the precursor has been plastically deformed to match part of a body of a person.

\* \* \* \* \*